US008920752B2

(12) United States Patent
Tisone et al.

(10) Patent No.: US 8,920,752 B2
(45) Date of Patent: Dec. 30, 2014

(54) SYSTEMS AND METHODS FOR HIGH SPEED ARRAY PRINTING AND HYBRIDIZATION

(71) Applicant: Biodot, Inc., Irvine, CA (US)

(72) Inventors: Thomas C Tisone, Irvine, CA (US); Holger Eickhoff, Syke (DE)

(73) Assignee: Biodot, Inc., Irvine, CA (US)

( * ) Notice: Subject to any disclaimer, the term of this patent is extended or adjusted under 35 U.S.C. 154(b) by 101 days.

(21) Appl. No.: 13/757,578

(22) Filed: Feb. 1, 2013

(65) Prior Publication Data
US 2013/0150266 A1 Jun. 13, 2013

Related U.S. Application Data

(62) Division of application No. 12/016,961, filed on Jan. 18, 2008, now abandoned.

(60) Provisional application No. 60/881,322, filed on Jan. 19, 2007.

(51) Int. Cl.
B01L 3/02 (2006.01)
G01N 1/10 (2006.01)
G01N 35/10 (2006.01)
C40B 60/14 (2006.01)
C12M 1/34 (2006.01)
B01J 19/00 (2006.01)

(52) U.S. Cl.
CPC ....... C12M 41/00 (2013.01); B01J 2219/00385 (2013.01); B01J 2219/00527 (2013.01);
(Continued)

(58) Field of Classification Search
CPC .............. G01N 35/10; G01N 35/1002; G01N 35/1011; G01N 35/1016; G01N 35/1065; G01N 35/1067; G01N 35/1074; B01L 3/02; B01L 3/0241; C40B 60/14; B01J 19/0046

USPC .......... 422/509, 518, 501, 504, 521, 63–68.1; 436/43–54, 180; 73/863.32, 863.33, 73/864, 864.01, 864.02, 864.11, 864.13, 73/864.14, 864.16, 864.17, 864.21, 73/864.22, 864.25, 864.31; 506/33–40
See application file for complete search history.

(56) References Cited

U.S. PATENT DOCUMENTS 2,264,564 A 12/1941 Connor
2,512,743 A 6/1950 Hansell
(Continued)

FOREIGN PATENT DOCUMENTS

EP 0 810 438 A2 12/1997
EP 0 810 438 A3 9/1998
(Continued)

OTHER PUBLICATIONS

International Preliminary Report on Patentability in corresponding international application No. PCT/US2008/051500 (filed Jan. 18, 2008), issued Jul. 21, 2009, 8 pp.
(Continued)

Primary Examiner — Brian R Gordon
(74) Attorney, Agent, or Firm — Knobbe Martens Olson & Bear LLP

(57) ABSTRACT

Novel and improved systems and methods for high speed arraying, hybridization, quantitative development and/or assaying are provided. Some embodiments provide a web based arraying format. Some other embodiments provide a sheet based arraying format. Some embodiments use a drop on drop assaying or hybridization mode. In some embodiments, a substantially inert substrate is utilized. In some other embodiments, an interactive substrate is utilized.

37 Claims, 39 Drawing Sheets

(52) U.S. Cl.
CPC .... *B01L 2400/065* (2013.01); *B01L 2300/0838* (2013.01); *B01J 2219/0036* (2013.01); *B01L 2400/0478* (2013.01); *B01J 2219/00698* (2013.01); B01L 3/0268 (2013.01); B01J 19/0046 (2013.01); *B01J 2219/00596* (2013.01); *B01J 2219/0072* (2013.01); *B01J 2219/00378* (2013.01); *B01J 2219/00695* (2013.01); *B01J 2219/00722* (2013.01); *B01J 2219/00725* (2013.01)
USPC ........... 422/509; 422/518; 422/501; 422/504; 422/521; 422/63; 422/67; 422/68.1; 436/43; 436/54; 436/180; 436/46; 506/37; 506/40; 73/864.01; 73/864.02; 73/864.24; 73/864.25; 73/864.31

(56) References Cited

U.S. PATENT DOCUMENTS

| | | | |
|---|---|---|---|
| 3,373,437 A | 3/1968 | Sweet et al. | |
| 3,452,360 A | 6/1969 | Williamson | |
| 3,512,173 A | 5/1970 | Damouth | |
| 3,946,398 A | 3/1976 | Kyser et al. | |
| 4,018,383 A | 4/1977 | Paton et al. | |
| 4,121,466 A | 10/1978 | Reichler et al. | |
| 4,199,013 A | 4/1980 | Reich et al. | |
| 4,223,558 A | 9/1980 | Schmider et al. | |
| 4,278,205 A | 7/1981 | Binoche | |
| 4,369,664 A | 1/1983 | Bunce et al. | |
| 4,478,094 A | 10/1984 | Salomaa et al. | |
| 4,492,322 A | 1/1985 | Hieftje et al. | |
| 4,555,957 A | 12/1985 | Frankel et al. | |
| 4,681,742 A | 7/1987 | Johnson et al. | |
| 4,717,049 A | 1/1988 | Green et al. | |
| 4,748,043 A | 5/1988 | Seaver et al. | |
| 4,877,745 A | 10/1989 | Hayes et al. | |
| 4,922,852 A | 5/1990 | Price | |
| 4,926,701 A | 5/1990 | Tompkins | |
| 4,944,922 A | 7/1990 | Hayashi | |
| 5,004,159 A | 4/1991 | Kistner | |
| 5,041,266 A | 8/1991 | Fox | |
| 5,056,462 A | 10/1991 | Perkins et al. | |
| 5,132,097 A | 7/1992 | Van Deusen et al. | |
| H0001099 H | 9/1992 | Sayler | |
| 5,257,657 A | 11/1993 | Gore | |
| 5,320,250 A | 6/1994 | La et al. | |
| 5,324,480 A | 6/1994 | Shumate et al. | |
| 5,334,353 A | 8/1994 | Blattner | |
| 5,338,688 A | 8/1994 | Deeg et al. | |
| 5,486,337 A | 1/1996 | Ohkawa | |
| 5,505,777 A | 4/1996 | Ciardella et al. | |
| 5,509,966 A | 4/1996 | Sykes | |
| 5,525,515 A | 6/1996 | Blattner | |
| 5,529,756 A | 6/1996 | Brennan | |
| 5,542,289 A | 8/1996 | Hool et al. | |
| 5,558,838 A | 9/1996 | Uffenheimer | |
| 5,593,839 A | 1/1997 | Hubbell et al. | |
| 5,593,893 A | 1/1997 | Kobashi et al. | |
| 5,601,980 A | 2/1997 | Gordon et al. | |
| 5,601,982 A | 2/1997 | Sargent et al. | |
| 5,621,443 A | 4/1997 | Buschulte et al. | |
| 5,636,788 A | 6/1997 | Wilson | |
| 5,658,802 A | 8/1997 | Hayes et al. | |
| 5,707,588 A | 1/1998 | Tsukishima | |
| 5,711,989 A | 1/1998 | Ciardella et al. | |
| 5,738,728 A | 4/1998 | Tisone | |
| 5,741,554 A | 4/1998 | Tisone | |
| 5,742,304 A | 4/1998 | Richtsmeier et al. | |
| 5,743,960 A | 4/1998 | Tisone | |
| 5,744,305 A | 4/1998 | Fodor et al. | |
| 5,747,102 A | 5/1998 | Smith et al. | |
| 5,750,881 A | 5/1998 | Dorenkott et al. | |
| 5,756,050 A | 5/1998 | Ershow et al. | |
| 5,763,278 A | 6/1998 | Sickinger et al. | |
| 5,770,151 A | 6/1998 | Roach et al. | |
| 5,770,160 A | 6/1998 | Smith et al. | |
| 5,807,522 A | 9/1998 | Brown et al. | |
| 5,811,306 A | 9/1998 | Komatsu | |
| 5,853,894 A | 12/1998 | Brown | |
| 5,886,716 A | 3/1999 | Heinzl et al. | |
| 5,916,524 A | 6/1999 | Tisone | |
| 5,925,732 A | 7/1999 | Ecker et al. | |
| 5,927,547 A | 7/1999 | Papen et al. | |
| 5,958,342 A | 9/1999 | Gamble et al. | |
| 5,967,202 A | 10/1999 | Mullen et al. | |
| 5,981,733 A | 11/1999 | Gamble | |
| 5,985,214 A | 11/1999 | Stylli et al. | |
| 5,999,949 A | 12/1999 | Crandall | |
| 6,004,617 A | 12/1999 | Schultz et al. | |
| 6,044,212 A | 3/2000 | Flavin et al. | |
| 6,063,339 A | 5/2000 | Tisone et al. | |
| 6,083,762 A | 7/2000 | Papen et al. | |
| 6,100,030 A | 8/2000 | McCasky Feazel et al. | |
| 6,101,946 A * | 8/2000 | Martinsky | 101/494 |
| 6,103,479 A | 8/2000 | Taylor | |
| 6,114,178 A | 9/2000 | Dezael et al. | |
| 6,121,048 A | 9/2000 | Zaffaroni et al. | |
| 6,143,252 A | 11/2000 | Haxo, Jr. et al. | |
| 6,146,594 A * | 11/2000 | De Graaff et al. | 422/501 |
| 6,150,173 A | 11/2000 | Schubert | |
| 6,168,915 B1 | 1/2001 | Scholl et al. | |
| 6,203,759 B1 | 3/2001 | Pelc et al. | |
| 6,220,075 B1 | 4/2001 | Papen et al. | |
| 6,225,061 B1 | 5/2001 | Becker et al. | |
| 6,362,004 B1 * | 3/2002 | Noblett | 436/43 |
| 6,420,180 B1 * | 7/2002 | Bass | 436/43 |
| 6,453,929 B1 | 9/2002 | Johnson et al. | |
| 6,485,690 B1 | 11/2002 | Pfost et al. | |
| 6,521,187 B1 | 2/2003 | Papen | |
| 6,537,505 B1 | 3/2003 | LaBudde et al. | |
| 6,548,263 B1 | 4/2003 | Kapur et al. | |
| 6,551,557 B1 | 4/2003 | Rose et al. | |
| 6,569,687 B2 | 5/2003 | Doktycz et al. | |
| 6,576,295 B2 | 6/2003 | Tisone | |
| 6,585,296 B1 | 7/2003 | Picha et al. | |
| 6,589,791 B1 | 7/2003 | LaBudde et al. | |
| 6,599,479 B1 | 7/2003 | Kietzmann et al. | |
| 6,627,157 B1 | 9/2003 | Doktycz et al. | |
| RE38,281 E | 10/2003 | Tisone | |
| 6,642,054 B2 * | 11/2003 | Schermer et al. | 436/43 |
| 6,669,909 B2 | 12/2003 | Shvets et al. | |
| 6,710,335 B2 | 3/2004 | Ellson et al. | |
| 6,713,021 B1 | 3/2004 | Shvets et al. | |
| 6,767,748 B2 * | 7/2004 | Yokokawa et al. | 436/180 |
| 6,797,945 B2 | 9/2004 | Berggren et al. | |
| 6,816,742 B2 | 11/2004 | Kim et al. | |
| 6,838,051 B2 | 1/2005 | Marquiss et al. | |
| 6,852,291 B1 | 2/2005 | Johnson et al. | |
| 6,864,201 B2 * | 3/2005 | Schultz et al. | 506/12 |
| 6,879,915 B2 * | 4/2005 | Cattell | 702/20 |
| 6,890,485 B1 | 5/2005 | Stylli et al. | |
| 6,890,760 B1 * | 5/2005 | Webb | 436/180 |
| 6,902,703 B2 * | 6/2005 | Marquiss et al. | 422/505 |
| 6,936,474 B2 * | 8/2005 | Chiou et al. | 506/40 |
| 6,943,036 B2 * | 9/2005 | Bass | 436/180 |
| 6,995,024 B2 | 2/2006 | Smith et al. | |
| 7,101,508 B2 * | 9/2006 | Thompson et al. | 422/67 |
| 7,141,368 B2 | 11/2006 | Fisher et al. | |
| 7,179,423 B2 | 2/2007 | Bohm et al. | |
| 7,199,809 B1 | 4/2007 | Lacy et al. | |
| 7,211,223 B2 | 5/2007 | Fouillet et al. | |
| 7,312,068 B2 | 12/2007 | Pinkel et al. | |
| 7,332,347 B2 | 2/2008 | Li et al. | |
| 7,442,665 B2 * | 10/2008 | Schultz et al. | 502/64 |
| 7,470,547 B2 | 12/2008 | Tisone et al. | |
| 7,767,627 B1 * | 8/2010 | Goldwasser et al. | 506/22 |
| 2001/0014477 A1 | 8/2001 | Pelc et al. | |
| 2001/0016177 A1 | 8/2001 | Pelc et al. | |
| 2001/0019845 A1 * | 9/2001 | Bienert et al. | 436/181 |
| 2001/0036424 A1 | 11/2001 | Takahashi et al. | |
| 2001/0048899 A1 * | 12/2001 | Marouiss et al. | 422/100 |
| 2001/0053337 A1 | 12/2001 | Doktycz et al. | |
| 2002/0001544 A1 * | 1/2002 | Hess et al. | 422/100 |
| 2002/0001675 A1 | 1/2002 | Tisone | |

(56) References Cited

U.S. PATENT DOCUMENTS

| | | | |
|---|---|---|---|
| 2002/0009391 A1* | 1/2002 | Marquiss et al. | 422/63 |
| 2002/0064482 A1 | 5/2002 | Tisone et al. | |
| 2002/0092366 A1 | 7/2002 | Brock et al. | |
| 2002/0142483 A1* | 10/2002 | Yao et al. | 436/180 |
| 2002/0151085 A1 | 10/2002 | Zaffaroni et al. | |
| 2002/0158027 A1 | 10/2002 | Moon et al. | |
| 2002/0159919 A1 | 10/2002 | Churchill | |
| 2002/0168297 A1 | 11/2002 | Shvets et al. | |
| 2003/0027342 A1* | 2/2003 | Sheridan et al. | 436/43 |
| 2003/0113233 A1* | 6/2003 | Nanthakumar | 422/100 |
| 2003/0124735 A1* | 7/2003 | Nanthakumar et al. | 436/180 |
| 2003/0143756 A1 | 7/2003 | Fisher et al. | |
| 2003/0148538 A1 | 8/2003 | Ng | |
| 2003/0161761 A1* | 8/2003 | Williams et al. | 422/63 |
| 2003/0167822 A1 | 9/2003 | Johnson et al. | |
| 2003/0170903 A1 | 9/2003 | Johnson et al. | |
| 2003/0175163 A1 | 9/2003 | Shvets et al. | |
| 2003/0207464 A1 | 11/2003 | Lemmo et al. | |
| 2003/0211620 A1 | 11/2003 | LaBudde | |
| 2003/0215957 A1 | 11/2003 | Lemmo et al. | |
| 2003/0228241 A1 | 12/2003 | Legge | |
| 2004/0009611 A1 | 1/2004 | Williams et al. | |
| 2004/0072364 A1 | 4/2004 | Tisone | |
| 2004/0072365 A1 | 4/2004 | Rose | |
| 2004/0091398 A1 | 5/2004 | Gilbert et al. | |
| 2004/0219688 A1 | 11/2004 | Churchill et al. | |
| 2004/0265185 A1 | 12/2004 | Kitagawa | |
| 2005/0003458 A1 | 1/2005 | Moore et al. | |
| 2005/0169808 A1* | 8/2005 | Pinkel et al. | 422/100 |
| 2005/0232823 A1 | 10/2005 | Brock et al. | |
| 2006/0024841 A1* | 2/2006 | Yao et al. | 436/180 |
| 2006/0211132 A1 | 9/2006 | Miledi et al. | |
| 2006/0263264 A1 | 11/2006 | Bohm et al. | |
| 2008/0226498 A1 | 9/2008 | Stylli et al. | |
| 2013/0017128 A1* | 1/2013 | Silbert et al. | 422/509 |

FOREIGN PATENT DOCUMENTS

| | | |
|---|---|---|
| EP | 0 990 528 A2 | 4/2000 |
| EP | 0 990 528 A3 | 6/2000 |
| EP | 1 099 484 A1 | 5/2001 |
| EP | 1 128 310 A2 | 8/2001 |
| EP | 1 128 310 A3 | 8/2001 |
| EP | 1 179 364 A2 | 2/2002 |
| EP | 1 179 368 A2 | 2/2002 |
| EP | 1 179 368 A3 | 10/2002 |
| EP | 1 179 364 A3 | 2/2003 |
| EP | 1 379 332 B1 | 11/2005 |
| EP | 1 485 204 B1 | 2/2006 |
| EP | 1 658 894 A1 | 5/2006 |
| WO | WO 97/44134 A1 | 11/1997 |
| WO | WO 99/30168 A1 | 6/1999 |
| WO | WO 99/42752 A1 | 8/1999 |
| WO | WO 99/42804 A2 | 8/1999 |
| WO | WO 02/076615 A2 | 10/2002 |
| WO | WO 03/072258 A1 | 9/2003 |

OTHER PUBLICATIONS

Deerac Fluidics, New Horizons in Low-Volume Liquid Handling—Technology, printed from the internet on Jan. 17, 2008, 3 pp.
High Precision Non-Contact Dispensing, Innovadyne Technologies, Inc., printed from the internet on Jan. 17, 2008, 5 pp.
Innovadyne Patents—Dispensing Instruments, Innovadyne Technologies, Inc., printed from the internet on Jan. 17, 2008, 4 pp.
International Search Report in corresponding international application No. PCT/US2008/051500, mailed Jun. 26, 2008, 7 pp.
International Search Report and Written Opinion in corresponding international application No. PCT/US2008/051500, mailed Sep. 17, 2008, 15 pp.
The sciFLEXARRAYER Piezo Dispenser, SCIENION AG, printed from the internet on Jan. 9, 2007, www.scienion.de, 2 pp.
Scienion Press Release of Nov. 24, 2004, printed from the internet on Jan. 9, 2007, www.scienion.de, 1 p.
The sciFLEXARRAYER Piezo Dispenser, SCIENION AG, sciFLEXARRAYER S5 / S11, printed from the internet on Jan. 15, 2008, www.scienion.de, 2 pp.
sciFLEXARRAYER Piezo Dispensers, SCIENION AG, The sciFLEXARRAYER S3, printed from the internet on Jan. 15, 2008, www.scienion.de, 2 pp.
sciFLEXARRAYER—ultra-low volume dispensing systems for R&D and manufacturing, printed from the internet on Jan. 15, 2008, www.scienion.de, 2 pp.
sciFLEXARRAYER S100—a top level high throughput production device, printed from the internet on Jan. 15, 2008, www.scienion.de, 2 pp.
Product Guide, TaqMan Gene Expression Assay Products, Applied Biosystems, Sep. 2005, 14 pp.
TaqMan Gene Expression Assays, Applied Biosystems, Dec. 2006, 24 pp.
International Preliminary Report with Written Opinion issued Jul. 21, 2009 for PCT/US2008/051500 filed Jan. 18, 2008.

* cited by examiner

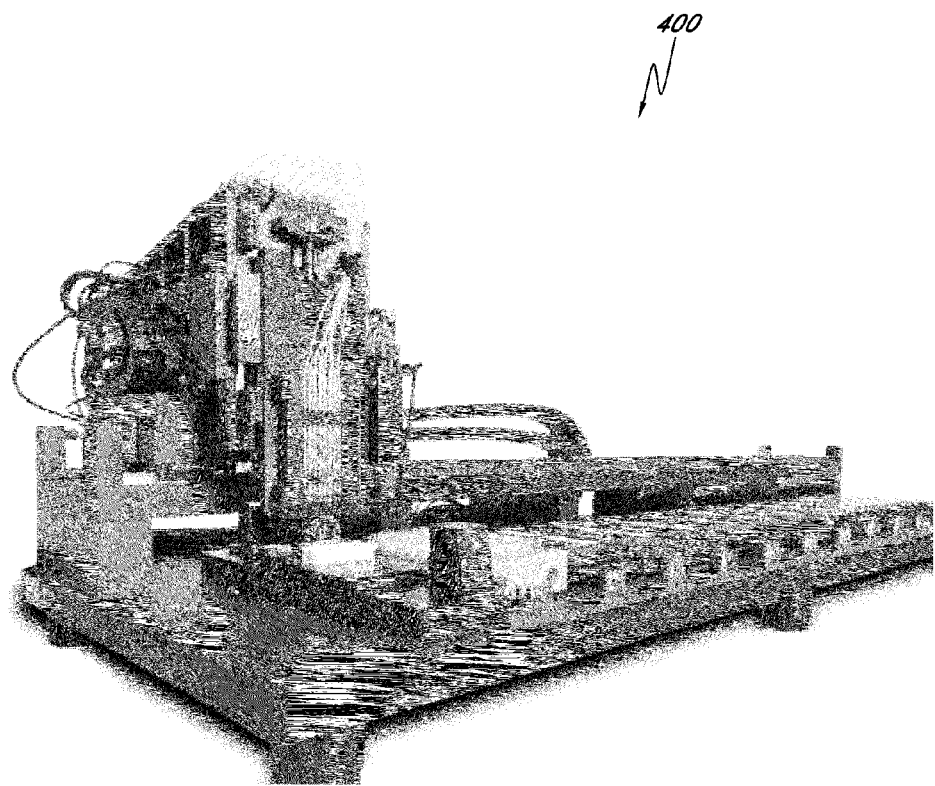
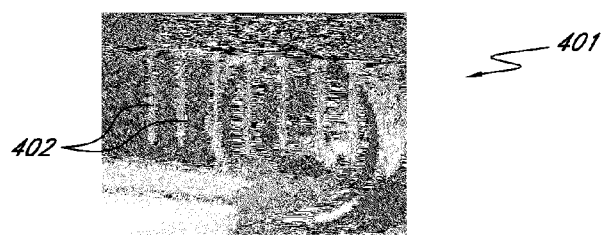
FIG. 1B

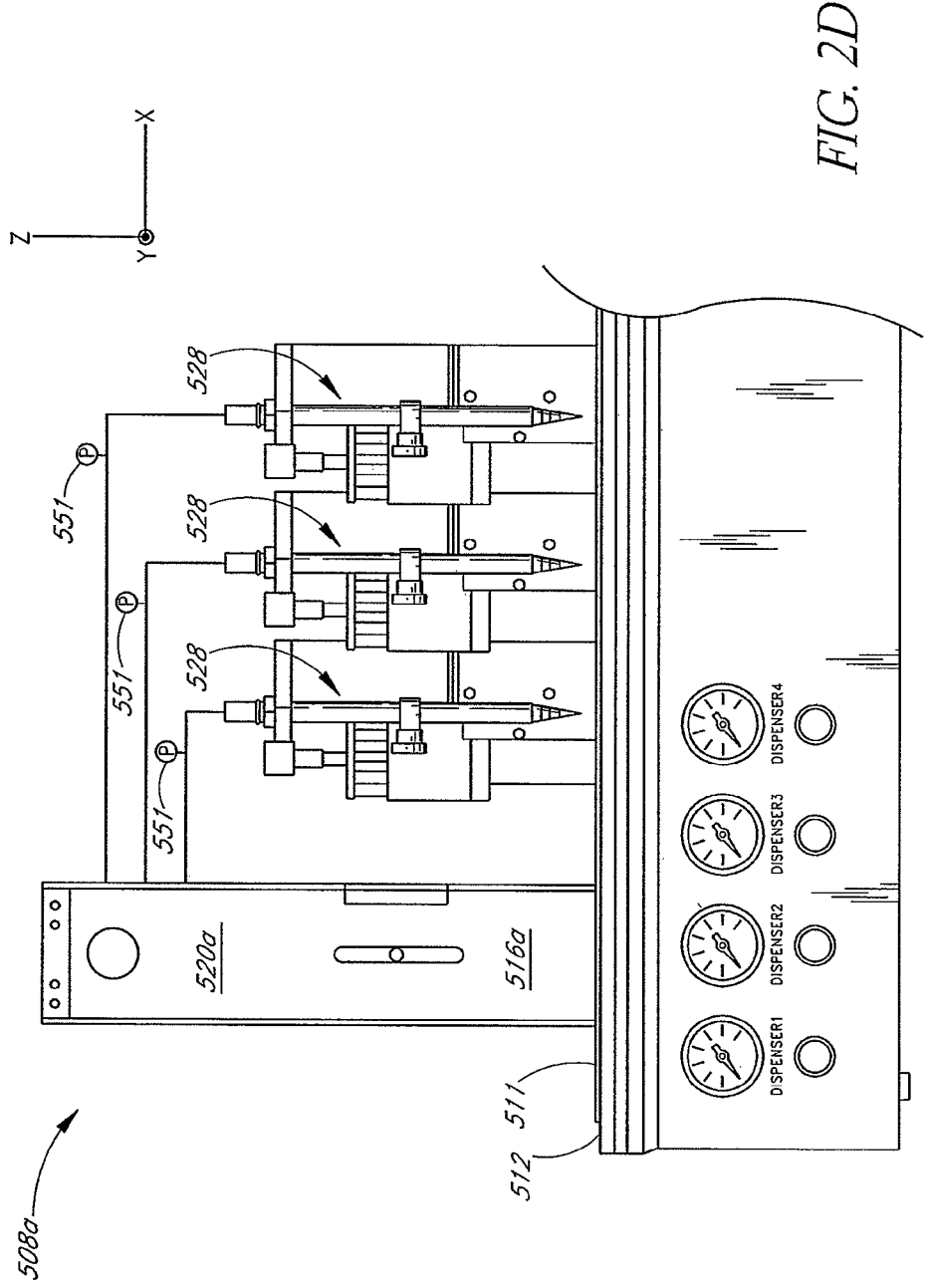

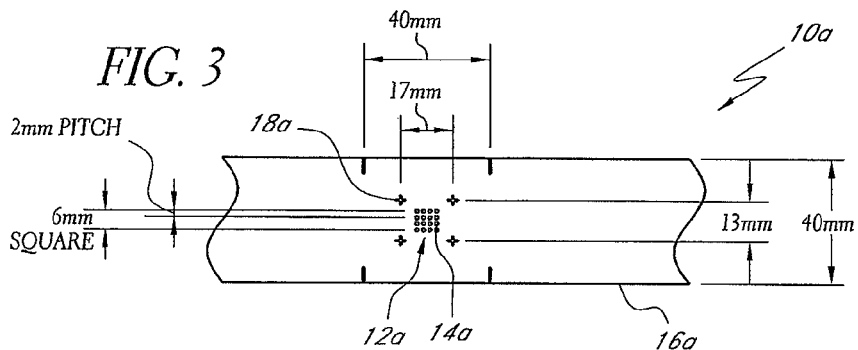
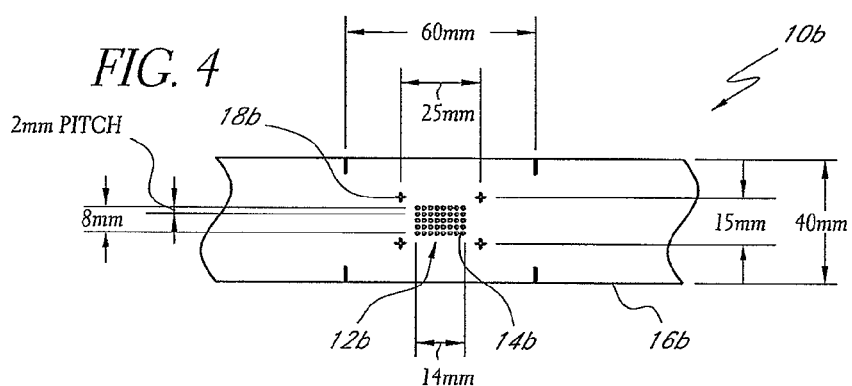
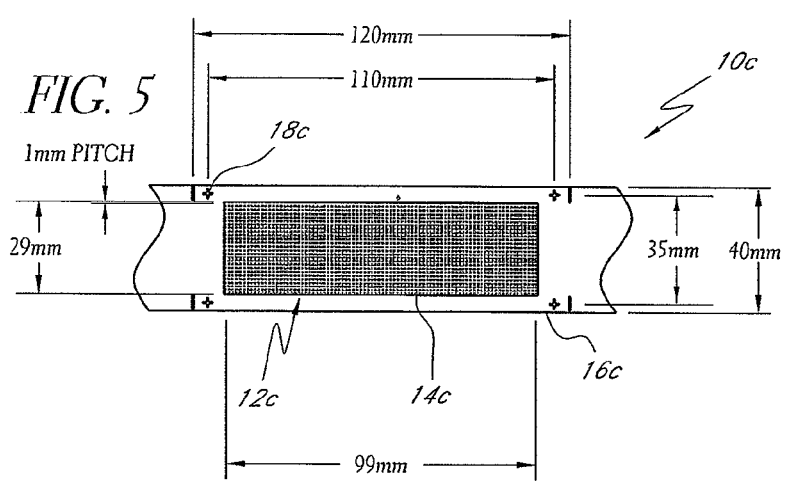

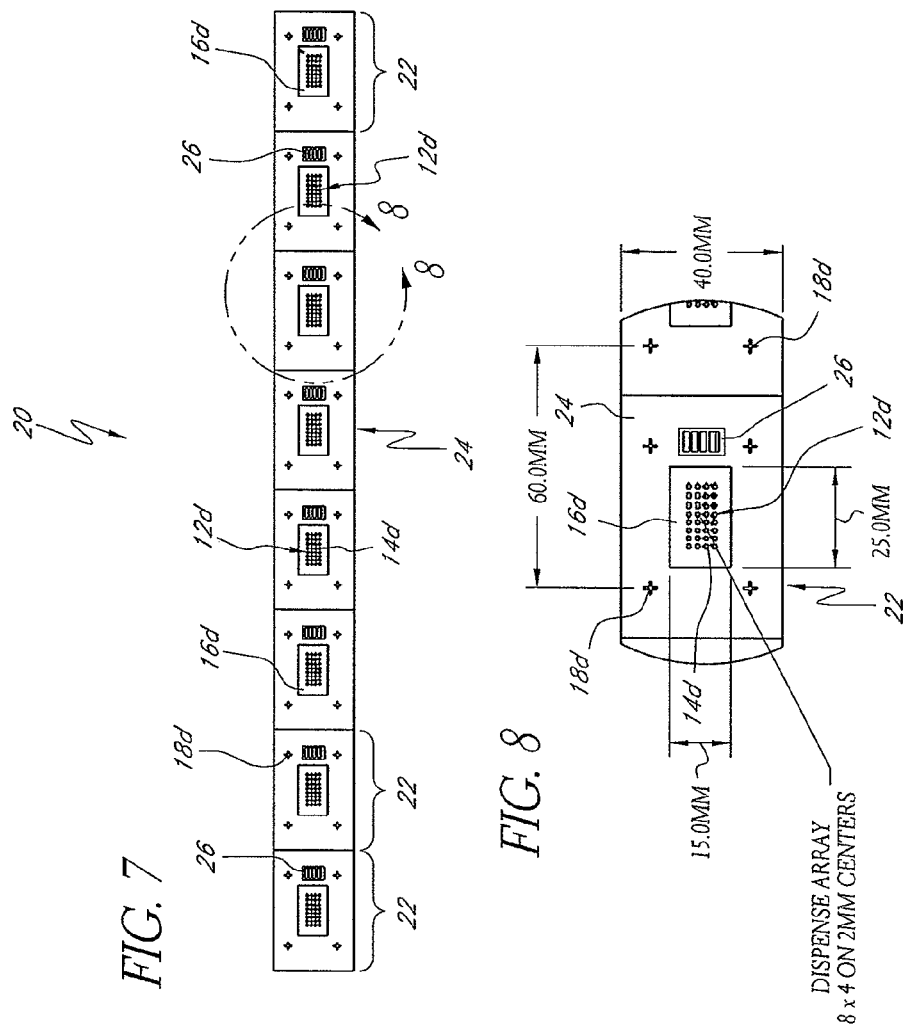

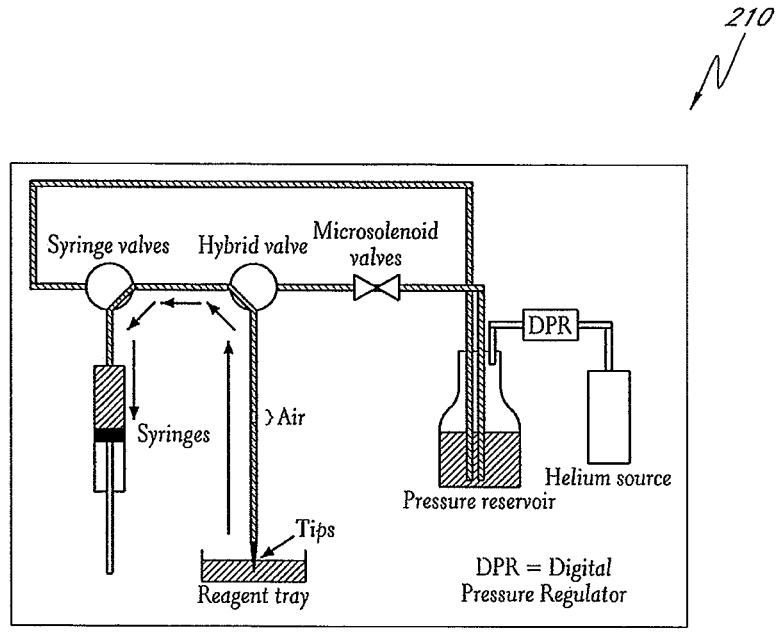
FIG. 13A  Reagent Aspiration, using the Syringe Path
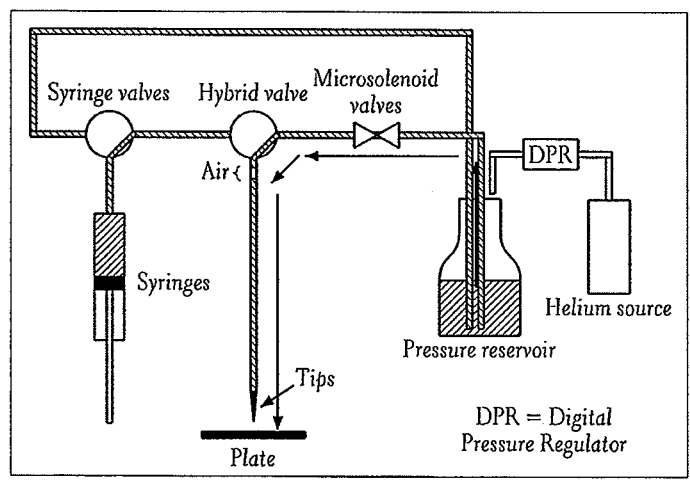
FIG. 13B  Reagent Dispense, using the Pressure Path

SIMPLE GENE EXPRESSION ANALYSIS WORKFLOW

SYSTEMS AND METHODS FOR HIGH SPEED ARRAY PRINTING AND HYBRIDIZATION

CROSS-REFERENCE TO RELATED APPLICATIONS

This application is a divisional application of U.S. patent application Ser. No. 12/016,961, filed Jan. 18, 2008, now abandoned, which claims the benefit of U.S. Provisional Application Ser. No. 60/881,322, filed Jan. 19, 2007, the entirety of each one of which is hereby incorporated by reference herein.

BACKGROUND OF THE INVENTION

1. Field of the Invention

The invention relates in general to diagnostic systems and methods and, more particularly, to systems and methods for high speed array printing, hybridization, quantitative development and assaying.

2. Description of the Related Art

Diagnostic formats involving microarrays or biochips continue to have a broad range of applications, such as, but not limited to, the fields of genomics and proteomics, among others. These technologies not only relate to the creation of the arrays but also to their processing and assaying such as hybridization. In many cases, valuable reagents need to be effectively utilized in small quantities which can be as low in the picoliter range.

Conventional systems, technologies and processes used in and/or associated with such diagnostic applications suffer from many drawbacks. These can include procedures which are relatively slow, take considerable time and hence are unable to achieve a desirably high throughput—this not only reduces process efficiency but also undesirably adds to the cost. Moreover, it is a difficult task to effectively utilize small quantities of chemical or biological reagents and other liquids when complex steps to precisely handle, transfer, deliver and process such small liquid quantities are entailed.

SUMMARY OF THE INVENTION

Microarrays or biochips are beginning to evolve into useful diagnostic formats for a broad range of applications that include, but are not limited to, human, veterinary, agriculture, and food markets, among others. The arrays can be based on a wide range of sensor molecules that include, but are not limited to, DNA, Oligonucleotides, proteins, antibodies, carbohydrates, cells, and small molecules, among others.

Research arrays tend to have high densities in the range of five to tens of thousands of spots or greater in order to achieve maximum information. Diagnostic applications are highly focused on a small number of targets and hence tend to have densities in the hundreds of spots or less.

Traditionally microarray development has been based on the use of small spots on a substrate such as glass where the spot sizes are typically in the range of about 100 microns ($\mu$m) to about 300 microns ($\mu$m). This has allowed spot densities in excess of 50,000 to be printed on a glass slide.

Spotting has been done with contact pins and piezoelectric non contact dispensing of drops in the picoliter range. Another driving force for using small spots has been the cost of the reagents for large spotting libraries. Research and development (R&D) arrays are typically printed in volumes under 200,000 per year as the conventional processing throughput is disadvantageously slow due to both the process speed and number of spots being printed.

Traditional microarraying is based on the use of aspiration and dispense processes where the source chemistries are presented in microtiter plate formats from which the reagents are aspirated and then dispensed (A/D) onto the array substrate. This conventional process undesirably requires a careful cleaning process each time the reagents are changed which results in a high overhead time and thus disadvantageously reduces production throughput.

This is the case for both conventional non-contact and contact dispensing approaches. These approaches can also undesirably waste valuable reagents due to washing, drying and/or dilution of the target reagents during the spotting process. Hence, high throughput manufacturing requires the use of bulk reagent dispensing using independent dispense heads.

The challenges for the adaptation of microarrays to large market diagnostic applications wherein the number of devices will be in the range from about 1 million to about 1,000 million lies in the ability to establish manufacturing strategies that can achieve array format densities and throughput capabilities. Other desirable features will include the ability to achieve performance coefficient of variations (CVs) and satisfy validation protocols.

Another important consideration for microarray formats is the hybridization process which develops the manufactured test for reading. Current methods of hybridization are undesirably slow and not suitable for major market segments such as point of sample testing (PST) wherein it is desirable to achieve test and read times typically less than 10 minutes. Disadvantageously, current hybridization techniques require much longer times while using expensive equipment with low throughput capabilities.

Advantageously, and as described further herein, systems and methods for high speed (and/or throughput) array printing, hybridization, quantitative development and assaying in accordance with certain embodiments of the invention achieve some or all of the above-mentioned desired or needed goals and/or objectives, and solve some or all of the above-mentioned problems and/or drawbacks.

Certain embodiments provide novel and improved systems and methods for high speed arraying, hybridization, quantitative development and/or assaying are provided. Some embodiments provide a web based arraying format. Some other embodiments provide a sheet based arraying format. Some embodiments use a drop on drop assaying or hybridization mode. In some embodiments, a substantially inert substrate is utilized. In some other embodiments, an interactive substrate is utilized.

In accordance with some embodiments a high speed array manufacturing system is provided. The system generally comprises a dispense module and a controller. The dispense module comprises a plurality of non-contact dispensers arranged in a predetermined configuration with a predetermined spacing for dispensing reagent drops onto a substrate medium. The controller provides relative motion between the dispensers and the substrate medium on which an array is formed to manufacture a substrate structure for assaying. The array has reagent spots dispensed on the substrate medium with spacings that are less than the spacings between the dispensers to form a high density substrate structure.

In accordance with some embodiments a high speed assaying system is provided. The system generally comprises a dispense module and a controller. The dispense module comprises a dispense head and a motion positioner. The dispense head comprises a plurality of non-contact dispensers arranged in a predetermined configuration with a predetermined spacing for dispensing reagent drops onto an array substrate with target spots formed thereon or therein such that the drops are precisely delivered at the position of the selected target spots. The controller monitors and controls said dispensers and the relative motion between the dispensers and the array substrate.

Some embodiments provide a combined high speed array manufacturing system and high speed assaying system. In some embodiments, the assaying involves hybridization. In some embodiments, the assaying involves PCR assaying.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 1B is a simplified view of a Scienion sciFLEXAR-RAYER™ S5 or S11 piezo dispenser, and an enlarged view of a dispensing head thereof, illustrating features and advantages in accordance with certain embodiments of the invention.

FIG. 2D is a simplified view of a dispensing apparatus with multiple dispensers and illustrating features and advantages in accordance with certain embodiments of the invention.

FIG. 3 is a simplified top view of a 16-spot array or microarray substrate illustrating features and advantages in accordance with certain embodiments of the invention.

FIG. 4 is a simplified top view of a 40-spot array or microarray substrate illustrating features and advantages in accordance with certain embodiments of the invention.

FIG. 5 is a simplified top view of a 3,000-spot array or microarray substrate illustrating features and advantages in accordance with certain embodiments of the invention.

FIG. 7 is a simplified top view of the web design substrate or substrate assembly of FIG. 6 illustrating features and advantages in accordance with certain embodiments of the invention.

FIG. 8 is a simplified enlarged view along line 8-8 of FIG. 7.

FIGS. 13A and 13B are simplified views of an aspirating and dispensing system illustrating features and advantages in accordance with certain embodiments of the invention.

DETAILED DESCRIPTION OF THE PREFERRED EMBODIMENTS

The preferred embodiments of the invention described herein relate generally to diagnostic systems and methods and, in particular, to systems and methods for high speed array printing, hybridization, quantitative development and assaying.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Some Non-Contact Dispensing Technology Embodiments

The working drop volume range suitable for production arrays lies in the range of picoliters to nanoliters which, in certain embodiments, is delivered by non contact methods in order to desirably meet process speeds which are suitable for high production throughputs.

In some embodiments, to dispense drops in the picoliter volume range, a state of the art technology and product base as available from Scienion AG of Berlin, Germany is utilized to deliver reagent at rates of up to about 5 drops/second using step and repeat indexing methods using bulk dispensing. In certain embodiments, an on the fly dispensing mode is utilized to increase this throughput to about 20 to about 50 depositions per second per dispenser, including all values and sub-ranges therebetween. In some embodiments, such as on the fly dispensing, the throughput is in the range from about 20 to about 500 depositions per second per dispenser, including all values and sub-ranges therebetween.

Scienion has also developed a disposable or reusable tip integrated with a piezo actuator for bulk dispensing of reagents known as SciSwift. This tip, in some embodiments, can be integrated into various machine configurations suitable to meet high throughput production requirements.

Figure 1A:
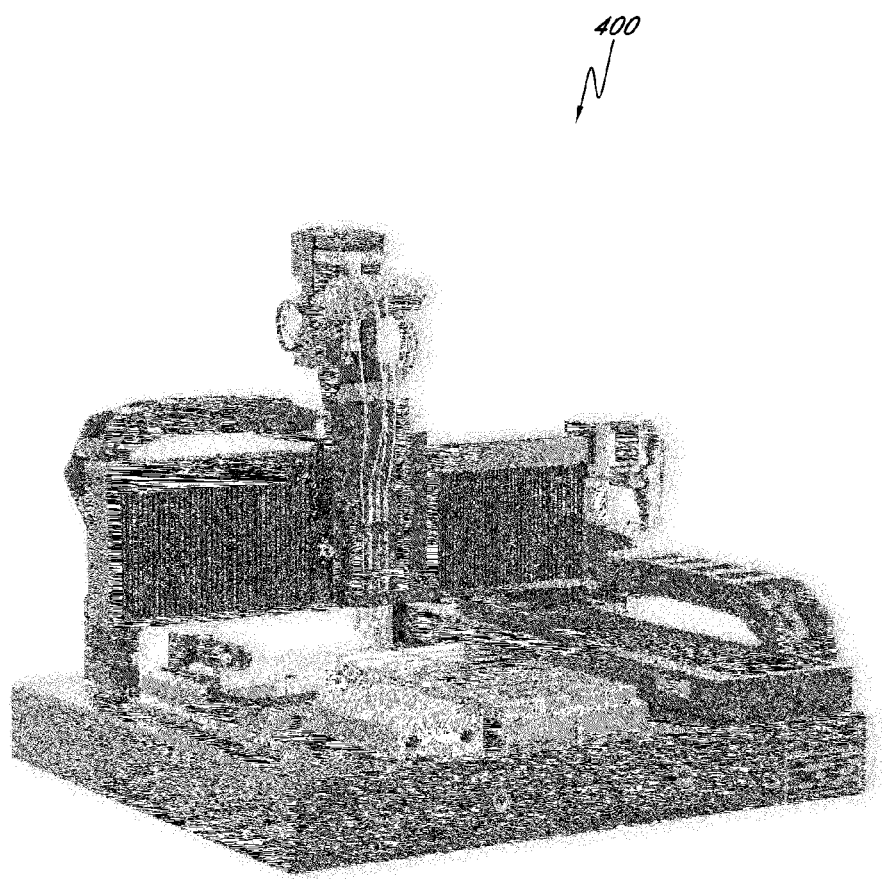
FIG. 1A is a simplified view of a Scienion sciFLEXAR-RAYER™ S3 piezo dispenser illustrating features and advantages in accordance with certain embodiments of the invention.
Figure 1C:
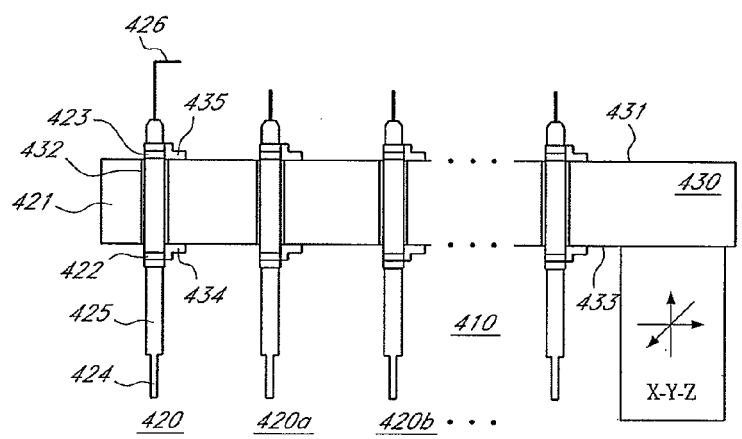
FIG. 1C is a simplified view of a piezo dispenser illustrating features and advantages in accordance with certain embodiments of the invention.

FIGS. 1A and 1B show various views and illustrate various features of Scienion sciFLEXARRAYER™ dispensing (and aspirating) and liquid handling systems (400, 400') used in conjunction with systems and methods in accordance with certain embodiments of the invention. U.S. Pat. No. 6,599, 479 B1, the entirety of which is hereby incorporated by reference herein, discloses a piezo electrically triggered multichannel dispensing (and aspirating) system (one embodiment is shown in FIG. 1C and referred to by reference numeral 410) which can be efficaciously utilized in accordance with certain embodiments of the invention. It is to be understood, that this patent document comprises a part of the present patent specification/application.

In general, the sciFLEXARRAYER embodiments provide ultra-low volume dispensing systems for R&D and manufacturing. The sciFLEXARRAYER product lines represent desirable tools for automated ultra-low volume liquid handling of biological samples in diagnostics, genomics and proteomics, among others.

In brief, certain embodiments of the sciFLEXARRAYER piezo dispensers are non-contact systems for producing high-quality, DNA micro-arrays, porotein micro-arrays, reversed phase protein micro-arrays, cell transfection arrays, and Glycan micro-arrays. Also, in brief, certain embodiments of the sciFLEXARRAYER piezo dispensers are non-contact systems for loading of biosensors, and matrix-assisted laser desorption/ionization (MALDI) targets. These embodiments are, without limitation, also operable in conjunction with many other ultra-low volume applications.

Advantageously, the sciFLEXARRAYER embodiments are capable of integration with well established technologies and also address the needs of specific customer needs from early research to high throughput manufacturing.

With particular reference to FIG. 1A, the dispensing system or apparatus 400 is a non-contact piezo dispenser for automated ultra-low volume liquid handling. This system 400 is desirably engineered robustly to handle many delicate substrates, advantageously provides a flexible tool in R&D and/or as reliable workhorse for manufacturing high quality arrays. Certain embodiments of the system 400 are specifically designed as beneficially providing a versatile tool in R&D. The dispensing system 400 of some embodiments provides an unsurpassed piezo-dispensing technology affordable, for example, for academic budgets. High-quality arrays can be desirably loaded, for example, MALDI targets or biosensors, among others, with efficacy.

Continuing with a discussion of the product description of the dispensing and arraying system 400, this technology involves an automated piezo driven non-contact dispensing system of ultra-low volumes, which in some embodiments, is specifically designed as economical entry unit for academic and R&D labs. Certain embodiments of the system 400 comprise an XYZ-stage with spindle drive, a piezo dispensing unit and a precision equipment for liquid handling. The system 400, in some embodiments, handles volumes from 100 picoliters up to several microliters. Advantageously, the system 400 is suitable for the production of DNA and protein microarrays, for cell transfection arrays, and for loading Matrix assisted Laser Desorption Ionisation Mass Spectrometry (MALDI-MS) targets or biosensor surfaces, among other features.

Embodiments of the system 400 desirably provide a heavy duty design and low maintenance components for long-term use as a flexible and highly dependable tool for drop-on-demand dispensing.

The system 400 advantageously provides several beneficial features and is particularly designed for a number of applications. These include, without limitation: DNA, protein, glycan arraying and biosensor loading; cell transfection arrays (and arraying); MALDI-MS sample preparation and target loading; accurate dilution series or addition of tiny aliquots of and/or to samples; printing chemical libraries; spotting onto customized targets, e.g. disc format (round targets or radial designs); assay development; and microarray-based analysis.

Some technical information relating to certain embodiments of the dispensing system 400 is presented in TABLE 1 below:

TABLE 1

| Dispensing System 400 | |
|---|---|
| Piezo Dispensing | Non-contact, drop-on-demand |
| No. of dispense capillaries | 1-8 (in any combination) |
| Minimum distance of dispense capillaries | 4.5 mm |
| Dispense volume | 100-500 picoliter (pL) per droplet |
| Capillary orifice | 50-90 microns (μm) |
| Capillary material | Borosilicate glass |
| Typical spot size | 120-250 μm |
| Typical pitch (spacing) | 300 μm (scaleable) |
| Dispense control | Integrated horizontal CCD Software: Windows XP based |
| Capacity | 1 holder (source plate) à 170 × 90 mm (MTP); 2 holders (targets) for a total of 20 standard glass slides; or 2 holders (target plates) à 170 × 90 mm (MTP) |
| Dimensions with enclosure (D, W, H) | 83 × 85 × 65 centimeter (cm) |
| Weight | 120 kilograms (kg) |

Several options are also available in conjunction with the dispensing system 400 for specific applications. These include, without limitation: humidity control; cooling unit; clean room; head-mounted camera; and software option for camera-based applications.

A wide variety of software systems may be used to control and coordinate the operation of the dispensing system 400. Advantageously, some embodiments of the software provide, without limitation: flexible and easy design of chip layout without any or minimal restrictions; programming of individual spotting routines by the user(s); a user friendly interface; and set-up of individual user profiles.

Embodiments of the dispensing system 400 desirably provide for individual configurations and enhanced versatility. For example, and without limitation: customization of hardware and software (e.g. environmental controls, software for pattern recognition); camera-based spotting (e.g. calculation of spot positions with guide dots); and barcodes (e.g. for identification and tracking).

With particular reference to FIG. 1B, the dispensing system or apparatus 400' is a non-contact piezo dispenser for automated ultra-low volume liquid handling. This figure also shows an enlarged view of a dispense head 401 of the system 400' comprising a plurality of dispensing channels or capillaries 402.

The dispensing system 400' provides a number of benefits and advantages. These include, without limitation: non-contact liquid handling of volumes from picoliter to microliter; the system's precise, robust X-Y magnetic linear stage is fast and maintenance-free; the transferred volume is constant and not affected by the target; non-contact dispensing substantially eliminates or reduces risk of contamination; "free-fly" of droplets allows dispensing into small cavities; re-spotting is facilitated by the system's drop-on-demand feature; efficient mixing of reagents is achieved; the dispense head 401 or individual capillaries 402 are easily changeable; exchange of target holders is swift and convenient; and the auto-drop function provides for a walk-away system.

Advantageously, the system 400' can be efficaciously utilized in a wide variety of applications. These include, without limitation: DNA, protein, glycan, and cell transfection arrays (and arraying); loading of biosensors; MALDI-MS sample preparation and target loading; accurate dilution series or addition of tiny aliquots to (and/or of) sample; printing chemical libraries; spotting onto disc format (round targets) and customized targets; assay improvement and screening assays; and any microarray-based analysis.

Some technical information relating to certain embodiments of the dispensing system 400' is presented in TABLE 2 below:

TABLE 2

| Dispensing System 400' | |
|---|---|
| Piezo Dispensing | Non-contact, drop-on-demand |
| No. of dispense capillaries | 1-8 (in any combination) |
| Minimum distance of dispense capillaries | 4.5 mm |
| Dispense volume | 100-500 picoliter (pL) per droplet |
| Capillary orifice | 50-90 microns (μm) |
| Capillary material | Borosilicate glass |
| Typical spot size | 120-250 μm |
| Typical pitch (spacing) | 300 μm (scaleable) |
| Dispense control | Integrated horizontal CCD camera system allows: manual or fully automated operation walk-away system, allows unattended production |

TABLE 2-continued

Dispensing System 400'

| | |
|---|---|
| Software | Windows XP based |
| Capacity - S5 embodiment | 5 holders à 170 × 90 mm |
| Capacity - S11 embodiment | 11 holders à 170 × 90 mm |
| Dimensions (D, W, H) - S5 embodiment | 850 × 580 × 450 millimeter (mm) |
| Dimensions (D, W, H) - S11 embodiment | 1400 × 580 × 450 mm |

Several options are also available in conjunction with the dispensing system 400', for example, for specific applications. These include, without limitation: humidity control; cooling unit; clean room enclosure; head-mounted camera; and software option for camera-based application.

A wide variety of software systems may be used to control and coordinate the operation of the dispensing system 400'. Advantageously, some embodiments of the software provide, without limitation: a user friendly, straight forward interface; flexible and convenient design of chip layout; no restrictions on target patterns, even radial designs; library of spotting routines (easily customizable); and individual user profiles.

Embodiments of the dispensing system 400' desirably provide for individual configurations and enhanced versatility. For example, and without limitation: customization of hardware and software (e.g. environmental controls, software for pattern recognition); connection to external equipment (e.g. plate hotels); camera-based spotting (e.g. calculation of spot positions with guide dots); and barcodes (e.g. for identification and tracking).

In some embodiments, a sciFLEXARRAYER S100 dispensing device ("the S100") available from Scienion AG of Berlin, Germany is utilized for liquid handling operations. The S100 is advantageously a top level high throughput production device, and provides a high throughput array and biosensor production instrument. Desirably, the S100 meets the high throughput production requirements of most bioarray formats like microtiter plates (MTPs), slides, wafers and a variety of biosensors, among others.

In embodiments of the S100 sciFLEXARRAYER, the targets are moved towards the dispense head mounted on each S100 portal and between each S100 portal via a conveyer belt. In some embodiments, each dispense head can be equipped with up to 12 sciSWIFT cartridges or sciDROP dispensers. Advantageously, this modularity allows the exact configuration of the system to the production volumes required. Moreover, and desirably, for customer specific applications, the system can be modified to meet any request (or a wide range of requests) for a variety of carrier formats. Additionally, the system can readily be adapted for special requirements, e.g., for software and hardware customization.

Some technical information, dispensing specifications and performance parameters relating to certain embodiments of the S100 dispensing system are presented in TABLE 3 below:

TABLE 3 sciFLEXARRAYER S100 Dispensing System

| | |
|---|---|
| Dimensions with enclosure (L × W × H) | min. 150 × 180 (2 portals) × 150 cm |
| Weight | min. 500 kg |
| Power Requirements | the machine runs on 400 V-500 V three-phase referencing |
| Referencing System | controlled via X, Y, Z stage and conveyer belt |
| Throughput | several 1000 per shift, approximately 1 array or sensor < 10 sec |

TABLE 3-continued sciFLEXARRAYER S100 Dispensing System

| | |
|---|---|
| Dispensing mode | aspirate/dispense mode using sciDROP technology; or bulk dispensing using sciSWIFT technology |
| Source | MTP, vessel or sciSWIFT cartridge |
| Target | carriers for 4 glass slide; other formats available as needed or desired |
| Options | e.g. target/carrier feed-in and feed-out |
| No. of portals | up to 12 |
| No. of dispense capillaries | 1-12 per portal |
| Minimum distance of dispense capillaries | 9.0 mm |
| Dispense volume | 100-500 pL per droplet |
| Typical spot size | 120-250 µm |
| Pitch (spacing) | scaleable |
| Dispense control | 2 CCD Cameras for XY correction |
| X-Y Axis | magnetic linear drives |
| Accuracy conveyer belts | <±200 µm |

U.S. Pat. No. 6,599,479 B1, the entirety of which is hereby incorporated by reference herein, discloses a multi-channel dispensing head including a plurality of micropipettes, each micropipette having an electrically actuatable trigger device with a ground and signal terminal; and a shared carrier having a plurality of receptacles located in a one- or two-dimensional arrangement and sized and shaped to receive said micropipettes, each receptacle having a ground and signal contact, wherein the ground and signal contacts on the carrier are spaced apart in the direction of a longitudinal axis extending through the respective micropipettes and each of the ground and signal contacts on the carrier contacting the ground and signal terminals of the trigger devices, respectively. The dispensing head delivers liquid droplets on or into predetermined locations of a target or substrate.

In some embodiments, U.S. Pat. No. 6,599,479 B1 provides a multichannel dispensing head in which micropipettes are arranged on a shared carrier in a two-dimensional or planar manner each with an electrically actuatable trigger device, which has a ground and signal terminal, the carrier having a ground or signal contact for each ground and signal terminal, wherein the ground and signal contacts on the carrier are arranged in two planes separated and electrically insulated from each other. The contacts on the carrier are spaced apart relative to the axial expansion (or longitudinal expansion) of the micropipettes. This configuration enables a greatly simplified design with a more compact micropipette arrangement.

Liquid handling embodiments disclosed in U.S. Pat. No. 6,599,479 B1 make reference to a dispensing head with piezoelectrically actuatable micropipettes, which are set up for the vertical release of microdrops on substrates in the sub-microliter (µL) range. However, the patent (U.S. Pat. No. 6,599,479) contemplates the use of a wide variety of microparticle placement devices with many types of trigger devices in which electrically actuated dispensers are arranged in rows or matrices, and the individual trigger devices of each dispenser are intended to be separately actuatable. Moreover, the patent (U.S. Pat. No. 6,599,479) contemplates formats for micropipette arrangement, which can be applied at any row length or matrix size for the vertical or horizontal microdrop or particle release.

FIG. 1C shows a schematic sectional view of a dispensing head, system or apparatus 410 in accordance with certain embodiments. The dispensing head 410 comprises a group of micropipettes 420 (420a, 420b, . . . ) that are attached to a shared carrier, gantry or arm 430, which can be adjusted with an x-y-z positioning device. Each micropipette 420 has a piezo element 421 as the trigger device with two control terminals comprising a ground terminal 422 and a signal terminal (or: phase terminal) 423. The micropipette 420 forms a load containing portion 424 at the pipette tip, which goes into a carrier containing portion 425 if needed. The opposite end of the micropipette has a pressure line 426. Though FIG. 1C shows a linear array of micropipettes, dispense channels or capillaries 420, the micropipettes can be efficaciously arranged in other manners (e.g., 2 or 3 dimensional arrays, non-linear arrays, staggered arrays, oblique or perpendicular arrays, arrays based on polar or cylindrical coordinates, combinations thereof, among others.)

The carrier 430 comprises at least one plate-shaped carrier element, which has receptacles 432 (432*a*, 432*b*, ...) for securing the micropipettes 420. In addition, the carrier 430 is provided with contacts 434, 435 at two spaced, electrically isolated, essentially flat areas, which in the depicted example are formed by the surfaces 431, 433 (or side surfaces) of the carrier element, each of these contacts comprising a ground contact 434 and a signal contact 435. The ground and signal contacts 434, 435 are each electrically connected with the ground and signal terminals 422, 423 of the piezo elements 421. Finally, electronic components and devices for attaching and connecting them can be provided on the carrier. To this end, the carrier is preferably a printed circuit board itself. In particular, the complete supply and demultiplexer electronics can be incorporated on the carrier.

An attachment device for holding the micropipette 420 is provided at each receptacle 432 of the carrier element 431. The attachment device is desirably detachable, so that individual micropipettes can be changed out. In one embodiment, the attachment device itself is formed by the ground and signal contacts 434, 435, provided the latter are spring elements, which act to retain the micropipettes 420 with the piezo element 421 in the receptacle 432.

As indicated with reference to FIG. 1C, each micropipette 420 is provided with a pressure line 426 which can simplify handling of a multi-channel dispensing head. In some embodiments, the pressure lines 426 of all micropipettes are connected with a distributor which is also secured to the dispensing head. A pressure supply line leads from the distributor to a fixed pressure device. The pressure device is provided to generate underpressures or overpressures for receiving carrier liquids, cleaning or stabilizing the pressure, which are conveyed by the distributor arrangement to the pressure lines 426 (e.g., gas pressure lines). The distributor can be a multi-valve or a branching arrangement. In the multi-valve arrangement, a number of valves corresponding to the number of micropipettes are provided at the dispensing head. The multi-valve arrangement desirably allows control of the pressure of individual micropipettes for charging or cleaning purposes. In the branching arrangement, the pressure supply line opens into the numerous pressure lines 426 without valves.

Embodiments of the dispensing head 410 and associated components, and other arrangements as disclosed in U.S. Pat. No. 6,599,479 B1 offer several advantages. The multi-channel dispensing head (e.g. dispensing head 410) has a desirably simplified design, which also permits a simplification of micropipette actuation depending on the specific micropipette arrangement through the use of, for example, demultiplex technology. In addition, the simplified structure is easier to manipulate, and, hence, can be positioned more precisely. Moreover, the arrangement of micropipettes (e.g., on a shared carrier) enhances overall operation relating to an increase in the number of parallel processed substances, thereby desirably resulting in a corresponding time savings. Also, the multi-channel dispensing head (e.g. dispensing head 410) advantageously enables a substantially fully automatic and reproducible control of dispensing head positioning and micro-drop release times based on predetermined program patterns, e.g., using a control computer.

In some embodiments, to dispense drops in the nanoliter range a technology and product base as available from BioDot, Inc. of Irvine, Calif., U.S.A. is utilized to deliver reagents at rates up to about 20 to about 50 parts or arrays per second using on-the-fly dispensing methods to deliver volumes in the range from about 20 nanoliter (nL) or less to about 100 nanoliter (nL) or more using bulk dispensing. In certain embodiments, on the fly dispensing modes are utilized to provide a throughput in the range from about 20 to about 50 depositions per second per dispenser, including all values and sub-ranges therebetween. In some embodiments, such as on the fly dispensing, the throughput is in the range from about 20 to about 500 depositions per second per dispenser, including all values and sub-ranges therebetween.

In brief, the BioDot dispensing (and/or aspirating) system in accordance with some embodiments, comprises a positive displacement syringe pump or device (or a direct current fluid source) hydraulically coupled or in fluid communication with a solenoid dispenser or actuator, and motion control means or device(s) to provide relative motion between the dispensing/aspirating tip and the target(s)/source(s), as needed or desired.

Any of these technologies, and many of the others taught or suggested herein, can be efficaciously utilized to place drops on previously dispensed spots or liquid drops in accordance with certain embodiments of the invention. Advantageously, this capability offers new, high speed approaches to the hybridization processes, and other assaying and quantitative development processes.

BioDot's U.S. Pat. Nos. 5,738,728, 5,741,554, 5,743,960, 5,916,524, 6,537,505 B1, 6,576,295 B2, RE38,281 E, U.S. Patent Application Publication Nos. US 2003/0211620 A1, US 2004/0072364 A1, US 2004/0072365 A1, US 2004/0219688 A1, US 2005/0056713 A1, US 2006/0211132 A1, and European Patent No. EP 1 485 204 B1, the entirety of each one of which is hereby incorporated by reference herein, disclose dispensing (and/or aspirating) systems and methods which can be efficaciously utilized in accordance with certain embodiments of the invention. All of these patent documents, as applicable, comprise a part of the present patent specification/application.

U.S. Pat. Nos. 6,063,339, 6,551,557 B1, 6,589,791 B1, and U.S. Patent Application Publication Nos. US 2002/0064482 A1, US 2003/0207464 A1, US 2003/0215957 A1, US 2003/0228241 A1, the entirety of each one of which is hereby incorporated by reference herein, disclose dispensing (and/or aspirating) systems and methods which can be efficaciously utilized in accordance with certain embodiments of the invention. All of these patent documents, as applicable, comprise a part of the present patent specification/application.

Figure 2A:
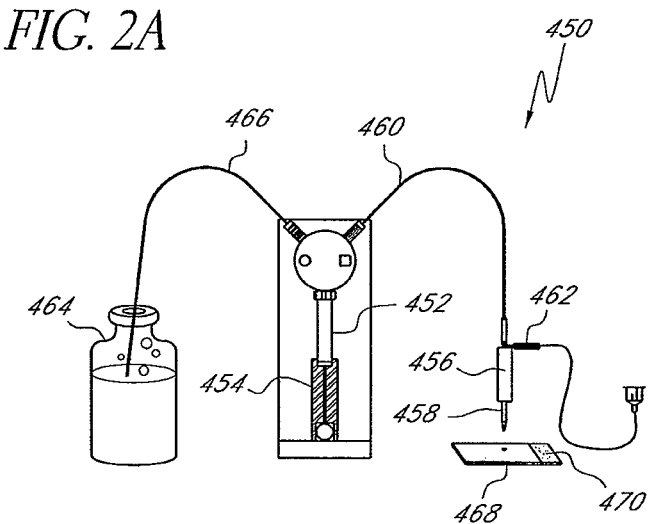
FIG. 2A is simplified schematic view of a BioJet Quanti™ dispenser illustrating features and advantages in accordance with certain embodiments of the invention.

FIG. 2A shows a BioJet Quanti™ dispensing system or apparatus 450 in accordance with certain embodiments. This quantitative non contact technology couples the BioDot "drop-on-demand" valve with a high resolution syringe pump to meter precise amounts of reagent. Incorporating the benefits of non-contact dispensing and the ability to program exact drop volumes, results in BioJet technology being a flexible and highly accurate technology.

The dispensing system 450 generally comprises a syringe 452 with a plunger 454 selectively communicable with a BioJet valve 456 and a dispense tip 458 via a dispense line

460. The figure also shows a BioJet valve connection 462. The syringe 452 is also selectively communicable with a reagent or liquid source 464 via a feed line 466. The system 450 dispenses droplets onto or into a target or substrate 468 which may be associated with backing cards 470.

Figure 2B:
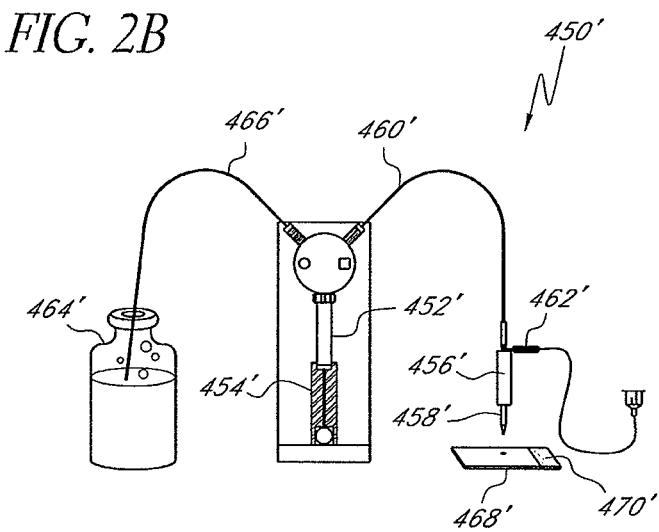
FIG. 2B is simplified schematic view of a BioJet Plus™ dispenser illustrating features and advantages in accordance with certain embodiments of the invention.

FIG. 2B shows a BioJet Plus™ dispensing system or apparatus 450' in accordance with certain embodiments. The proprietary BioJet Plus technology was developed for high speed dispensing. The technology involves (1) the coupling of a high speed micro solenoid valve with a high resolution syringe pump and (2) synchronization of the dispense system with the movements of the stage. The result is an extremely fast dispensing system which can deliver volumes from 20 nL to 4 µL in a single drop. BioJet Plus can work in either an Aspirate/Dispense mode or a Bulk Dispense mode. The BioJet Plus system can be used to dispense buffers, antibodies, enzymes or cells, among others. BioJet Plus dispensing is independent of the substrate allowing flexible dispensing to microtiter plates, glass slides or membranes. BioJet Plus systems are available from compact R&D systems to complete integrated manufacturing modules.

The dispensing system 450' generally comprises a syringe 452' with a plunger 454' selectively communicable with a BioJet Plus™ valve 456' and a ceramic dispense tip 458' via a dispense line 460'. The figure also shows a BioJet Plus™ valve connection 462'. The syringe 452' is also selectively communicable with a reagent or liquid source 464' via a feed line 466'. The system 450' dispenses droplets onto or into a target or substrate 468' which may be associated with sensor cards 470'.

In some embodiments, a tandem pump dispensing system is utilized by employing two syringe pumps for a single dispense operation where the syringes alternately fill and dispense to provide continuous flow for the dispensing operation. (Some embodiments of such a configuration are disclosed in U.S. Pat. No. RE38,281 E, the entirety of which is incorporated by reference herein.) The "Tandem Pump" configuration may be used in conjunction with any of the applicable dispensing embodiments taught or suggested herein. This desirably allows the use of small high resolution syringes in the range of 250 µL to be used. With this configuration continuous dispensing can be achieved with no limitations of the web length. In some embodiments, the "Tandem Pump" configuration is used for bulk dispensing on web based systems for both drop as well as continuous lines. For example, an aerosol type of dispense nozzle (e.g. see U.S. Pat. No. 5,738,728) that uses pressurized air to atomize the fluid passing through the nozzle can be utilized to create a quantitative spray format where a dot or line can be quantitatively generation on a continuous basis. In another example, the embodiments of FIGS. 2A and 2B can employ a "tandem pump" configuration to dispense drops at frequencies in the range of 20-1000 Hz to dispense non-contact drops on a continuous base. The advantages include: providing the ability to combine positive displacement dispensing with continuous operation; and versatility in configuration to allow adaptability to a range of different dispensing methods and/or systems.

U.S. Pat. Nos. 6,063,339, 5,916,524, 5,738,728, 5,743,960 and 5,741,554, the entirety of each one of which is hereby incorporated by reference, disclose the concept of a reagent dispensing apparatus and method in which a positive displacement syringe pump is used in combination with a liquid dispenser, such as a solenoid valve dispenser or piezoelectric dispenser, to achieve improved dispensing operations. The syringe pump meters a predetermined quantity or flow rate of reagent to the dispenser to regulate the quantity or flow rate of liquid reagent dispensed. Simultaneously, an associated X, X-Y or X-Y-Z table is controlled so as to move a substrate in coordinated relation with the dispenser operation such that the reagent density can be controlled, for example, in terms of volume of reagent deposited per unit length of substrate substantially independently of the particular flow characteristics of the liquid reagent or the particular operating parameters of the dispenser (within a given range).

Providing a positive displacement pump in series with the dispenser advantageously allows the quantity or flow rate of reagent to be controlled independently of the particular flow characteristics of the liquid being dispensed and/or the operating parameters of the particular dispenser. For example, the size of droplets formed by a dispenser can be adjusted by changing the operating frequency (for a solenoid valve or piezoelectric dispenser) or by adjusting the air pressure or exit orifice size (for an air brush dispenser) without affecting the flow rate of reagent. Also, the reagent flow rate can be controlled without substantial regard to the system operating parameters otherwise required to achieve stable dispensing operations. The quantity or flow rate of reagent dispensed is controlled or regulated independently by the positive displacement pump.

U.S. Patent Application Publication No. US 2004/0219688 A1, entitled METHOD AND APPARATUS FOR HIGH-SPEED MICROFLUIDIC DISPENSING USING TEXT FILE CONTROL, the entirety of which is hereby incorporated by reference herein, discloses the concept of a method and apparatus for dispensing reagents and other liquids onto a target or substrate and, in particular, a method and apparatus for high-speed precision dispensing, controlled by input data from a user-defined text file, of multiple chemical or biological reagents with the ability to dispense a wide dynamic range of dispense volumes in complex combinatorial patterns, ratios and arrays onto or into a high-density microwell plate, glass slide, receptive membrane, test strip, vial or other suitable target.

Certain embodiments relate to methods and systems for high-speed precision dispensing and/or aspirating of microfluidic and/or sub-microfluidic quantities of reagents and other liquids. In some embodiments, the operation of the systems is controlled by data accessed from a customized user-defined text file. Advantageously, the use of such text file control allows high-speed precision dispensing of one or more reagents with a wide dynamic range of dispense volumes in complex combinatorial patterns, ratios and arrays onto or into multiple predetermined locations of a desired target or substrate. This is particularly advantageous when a large number of permutations of different reagent and permutations of reagent volume ratios are involved. In some embodiments, the systems are operated in a high frequency modulated mode to further improve accuracy and reliability.

European Patent No. EP 1 485 204 B1, the entirety of each one of which is hereby incorporated by reference herein, discloses systems and methods for dispersing or dispensing liquids or reagents below a fluid surface using non-contact dispensing which can be efficaciously utilized in accordance with certain embodiments of the invention.

Some embodiments relate generally to dispensing of fluid droplets and in particular to methods and systems of dispersing, suspending or arranging microfluidic and/or sub-microfluidic volumes of droplets of chemical, biological or other reagents or liquids below the surface of a cover or host fluid using non-contact dispensing for creating an assay or reaction that produces a detectable signal or a by-product such as a harvestable protein crystal. Advantageously, evaporation of valuable reagents is substantially prevented or reduced.

Another advantage, in the case of miscible reagents, is that the drop velocities provide good mixing. Yet another advantage is that, in the non-contact dispensing scheme, the nozzle or tip is not immersed into the host fluid, thereby facilitating cleaning.

Figure 2C:
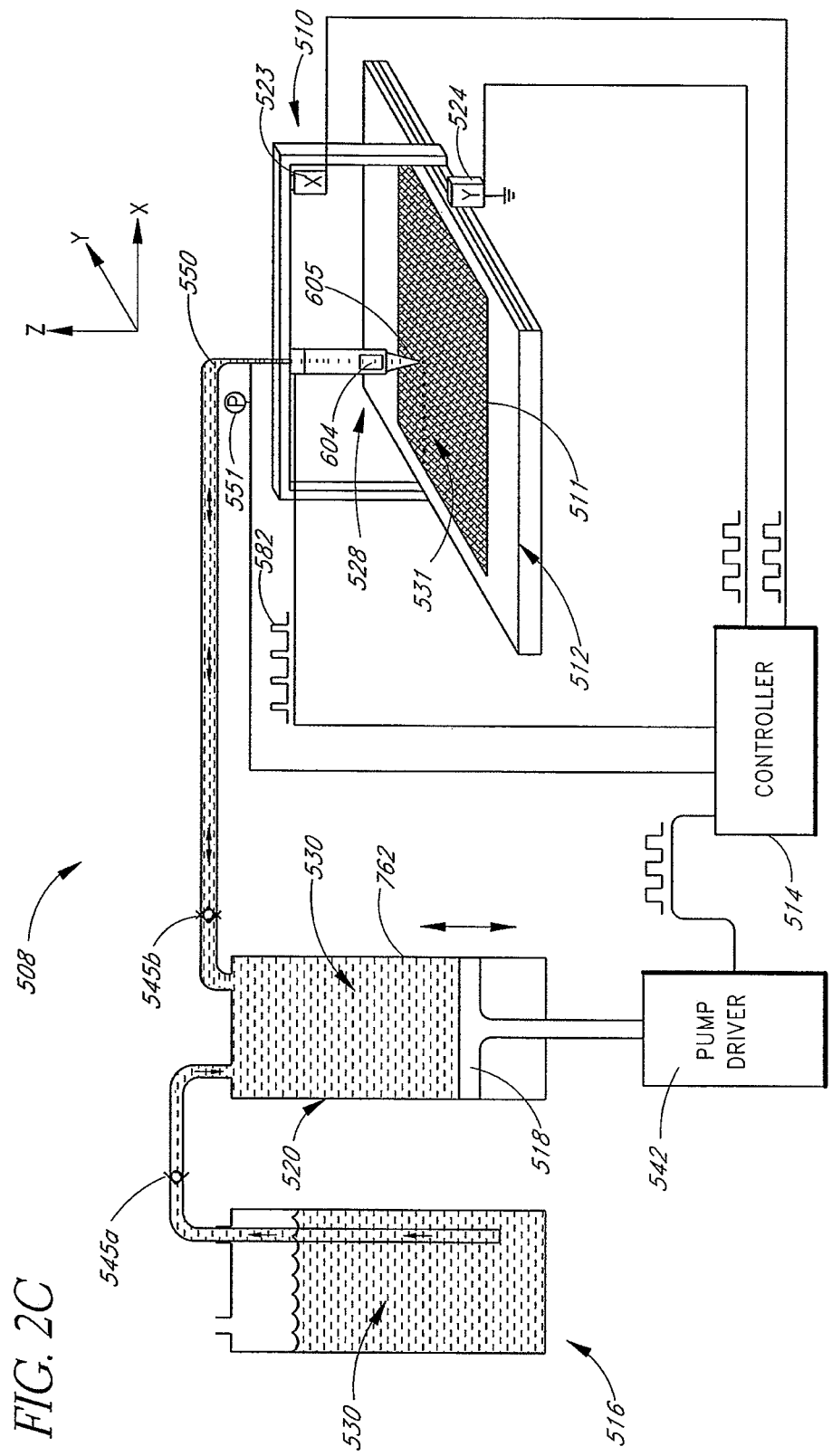
FIG. 2C is a simplified view of a dispensing apparatus illustrating features and advantages in accordance with certain embodiments of the invention.

FIG. 2C is a simplified overview of a dispensing apparatus 508 in accordance with certain embodiments. The dispensing apparatus 508 is particularly adapted for automated high-speed precision dispensing (and aspirating) of liquids such as chemical and biological reagents, for example, DNA, cDNA, RNA, proteins, peptides, oligonucletides, other organic or inorganic compounds, among others.

The dispensing apparatus 508 (FIG. 2C) generally comprises a dispensing head or dispenser 528 having a valve or other dispensing means 604 operated by an actuator, such as a solenoid. The dispenser 528 is hydraulically coupled or in fluid communication with a positive displacement pump 520 for metering precise quantities of fluid or liquid 530 to or towards the dispenser 528. The dispenser 528 is mounted on or in association with an X-Y table or gantry 510.

As shown in FIG. 2C, a substrate or target 511 is mounted on a carrier platform, table or carriage 512 to receive reagent or liquid dispensed from the dispenser 528. The target 511 can comprise one or more microtiter plates, glass slides, receptive membranes, test strips, or other suitable porous or non-porous targets such as one or more single-well receptacles, vials or tubes. The microtiter plates can be configured in 96, 384, 1536 and 2080 well plate formats, among other configurations.

Those skilled in the art will appreciate that the X-Y table 510 (FIG. 2C) may include one or more position stepper motors 523, 524 or the like, which are operable to move either the dispenser 528 and/or the carrier platform or table 512 relative to one another in the X, X-Y or X-Y-Z directions, as indicated in the drawing. Alternatively, or in addition, one or more suitable robot arms may be efficaciously used, as needed or desired, to provide controlled relative motion between the dispenser 528 and the target substrate 511 and/or other components or associated components of the apparatus 508.

Though FIG. 2C shows only a single dispenser 528, in other preferred embodiments and as discussed further below, it is contemplated that multiple dispensers in linear (1×N) or two-dimensional (M×N) arrays are used. These may be provided and operated either in parallel or in another coordinated fashion, as desired. It should be understood that any discussion herein with specific reference to the single dispenser embodiment is substantially equally applicable, with possible modifications as apparent to the skilled artisan, to multiple dispensers each connected to respective pumps or a single pump.

The positive displacement pump 520 (FIG. 2C) preferably comprises a syringe pump though other direct current (DC) fluid sources may be used with efficacy. The syringe pump 520 is hydraulically coupled to or in fluid communication with a fluid reservoir 516 through a first one-way check valve or open-close valve 545a. The syringe pump 520 draws fluid 530 from the fluid reservoir 516 and provides it to the dispenser 528 through a second check valve or open-close valve 545b on a supply line or feedline 550, as shown in FIG. 2C.

The syringe pump 520 (FIG. 2C) has a movable piston 518 within a syringe barrel 762. The syringe pump 520 is operated by a syringe pump driver 542 comprising, for example, a stepper motor and an associated lead screw, for extending and retracting the piston 518 within the syringe barrel 762. Those skilled in the art will readily appreciate that when the piston 518 is retracted, fluid 530 is drawn from the reservoir 516 into the syringe pump 520. When the piston 518 is again extended, fluid 530 is forced to flow from the syringe barrel 762 into the dispenser 528 via the supply tube 550, whereupon it is ejected by the dispenser 528 onto or into the target substrate 511 in the form of droplets 531 or a spray pattern.

In one embodiment, the fluid or liquid 530 (FIG. 2C) comprises the reagent that is dispensed onto or into the target 511. That is the system (reservoir 516, pump barrel 762, dispenser 528 and other connection lines) is filled with the reagent 530 to be dispensed. This set-up is particularly advantageous when relatively large quantities of the same reagent are to be dispensed.

In another embodiment, the fluid or liquid 530 (FIG. 2C) comprises a system fluid or backing reagent, such as distilled water, and the dispensing apparatus 508 operates in a "suck-and-spit" mode. In this embodiment, the dispenser 528 is used to aspirate a predetermined amount of fluid, liquid or reagent from a source receptacle or microtiter plate and the like and then dispense the aspirated reagent onto or into the target 511. As the skilled artisan will appreciate, reagent is aspirated by retracting or decrementing the pump piston 518 with the valve 545b open to create a reduced pressure or partial vacuum to draw source reagent into the dispenser 528 via a suitable tip or nozzle thereon.

A controller 514 (FIG. 2C) oversees operation of the pump 520, X-Y table 510 (or X, or X-Y-Z table) and the dispenser 528, among other associated components. The controller 514 coordinates and controls the motion of each of the stepper motors 523, 524, and the syringe pump driver 542, as well as the opening and closing of the dispensing valve 604 to precisely dispense an amount of reagent at one or more predetermined location(s) on or in the target substrate 511. The controller 514 also controls and coordinates aspiration of source reagent, as and if needed.

A computer software program is interfaced with the controller 514 (FIG. 2C) to guide dispensing (and/or aspirating) for different modes of operation and different applications. Preferably, a user-defined text file is created, for example, from a spreadsheet of values or template, with lists of numbers of user-defined dispense volumes of one or more reagents and corresponding coordinates of the dispense (and/or aspirate) operation. The controller 514 uses this text file data in cooperation with the software program to precisely control and coordinate the operation of the dispensing apparatus 508.

Advantageously, the use of such text file control allows high-speed precision dispensing of one or more reagents with a wide dynamic range of dispense volumes in complex combinatorial patterns, ratios and arrays onto or into multiple predetermined locations of a desired target or substrate. This is particularly advantageous when a large number of permutations of different reagent and permutations of reagent volume ratios are involved. In such cases, typically, more than one dispenser (see FIGS. 2D and 2E) or a manifold system (see FIG. 2F) or a combination thereof is utilized to facilitate process efficiency. These multiple dispensers can be operated in parallel or in synchronous coordination.

FIG. 2D is a simplified view of a dispensing apparatus 508a comprising a plurality of dispensers 528. As has been described above in reference to FIG. 2C, each dispenser 528 is connected to a respective pump 520 (in FIG. 2D, the pumps 520 are part of a pump bank 520a and a reservoir bank 516a comprises the reservoirs 516). A single reagent may be dispensed by all of the dispensers 528 or multiple reagents, as needed or desired. Moreover, reagent(s) can be first aspirated and then dispensed, as discussed above.

Still referring in particular to FIG. 2D, relative motion is provided between the substrate or target 511 and the dispensing channels 528. The dispensers 528 and/or the platform 512 are movable in the X, X-Y or X-Y-Z directions to allow for precision dispensing at predetermined locations. Multiple targets 511 may be placed on the table 512, as needed or desired. The dispensers 528 can be independently moved or together in the form of a dispense head comprising multiple dispense channels 528 paced from one another by predetermined distance(s). Moreover, the dispensers 528 can be individually (serially or sequentially) operated or substantially simultaneously (parallely) or a combination thereof, as needed or desired. A central or main controller, possibly in conjunction with sub-controllers, is used to control and coordinate the actuations of the pumps 520, dispensers 528 and relative movement between the target 511 and dispense channels 528.

Figure 2E:
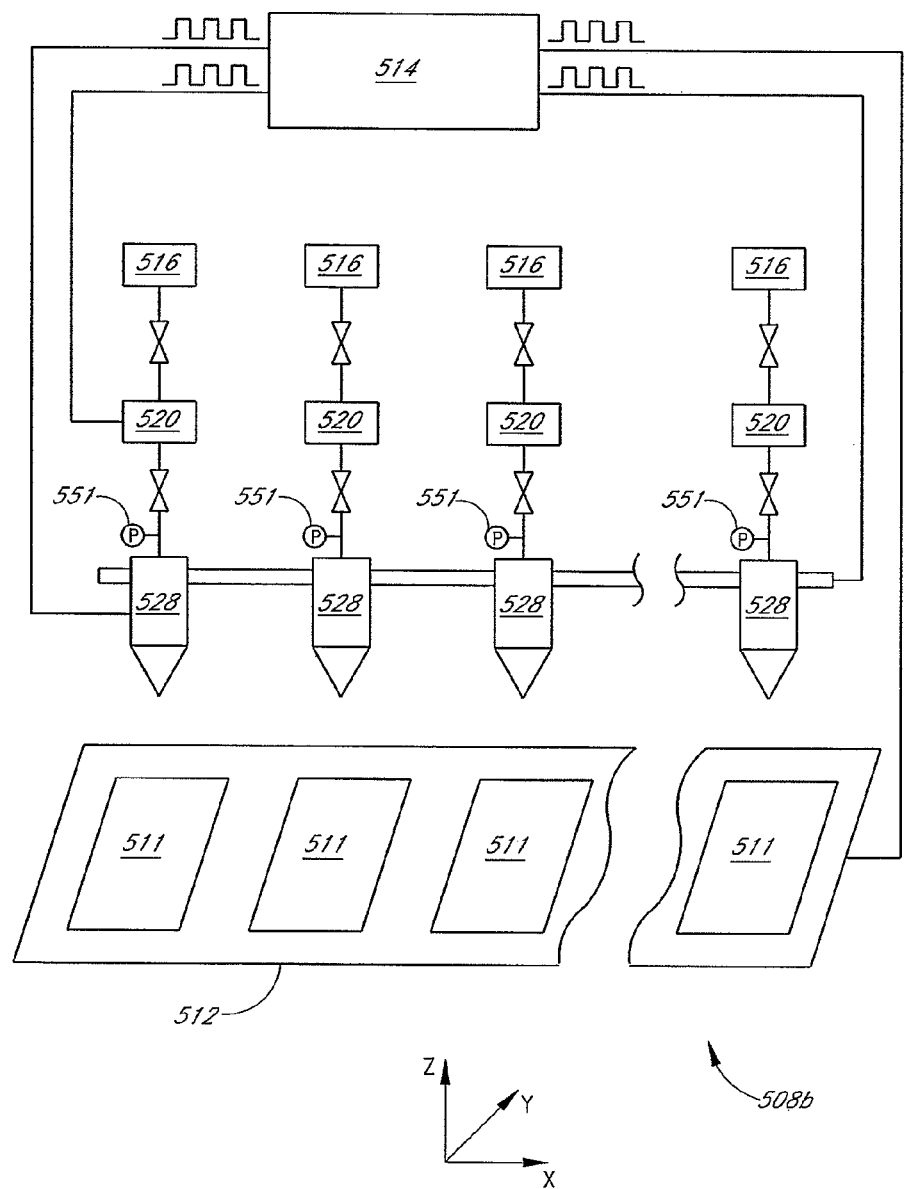
FIG. 2E is a schematic generalized illustration of a dispensing apparatus with an array of dispensers and illustrating features and advantages in accordance with certain embodiments of the invention.

FIG. 2E is a schematic view of a dispensing apparatus 508b comprising a plurality of dispensers 528. In general, the dispensing apparatuses described herein can comprise one or more dispensers 528 arranged in a wide variety of configurations such as linear (1×N), two-dimensional (M×N) or even three-dimensional (M×N×K) arrays. It should be noted that the array or collection of dispensers or dispenser heads 528 may be referred to as a "dispensing head" comprising multiple dispense channels or capillaries 528.

Figure 2F:
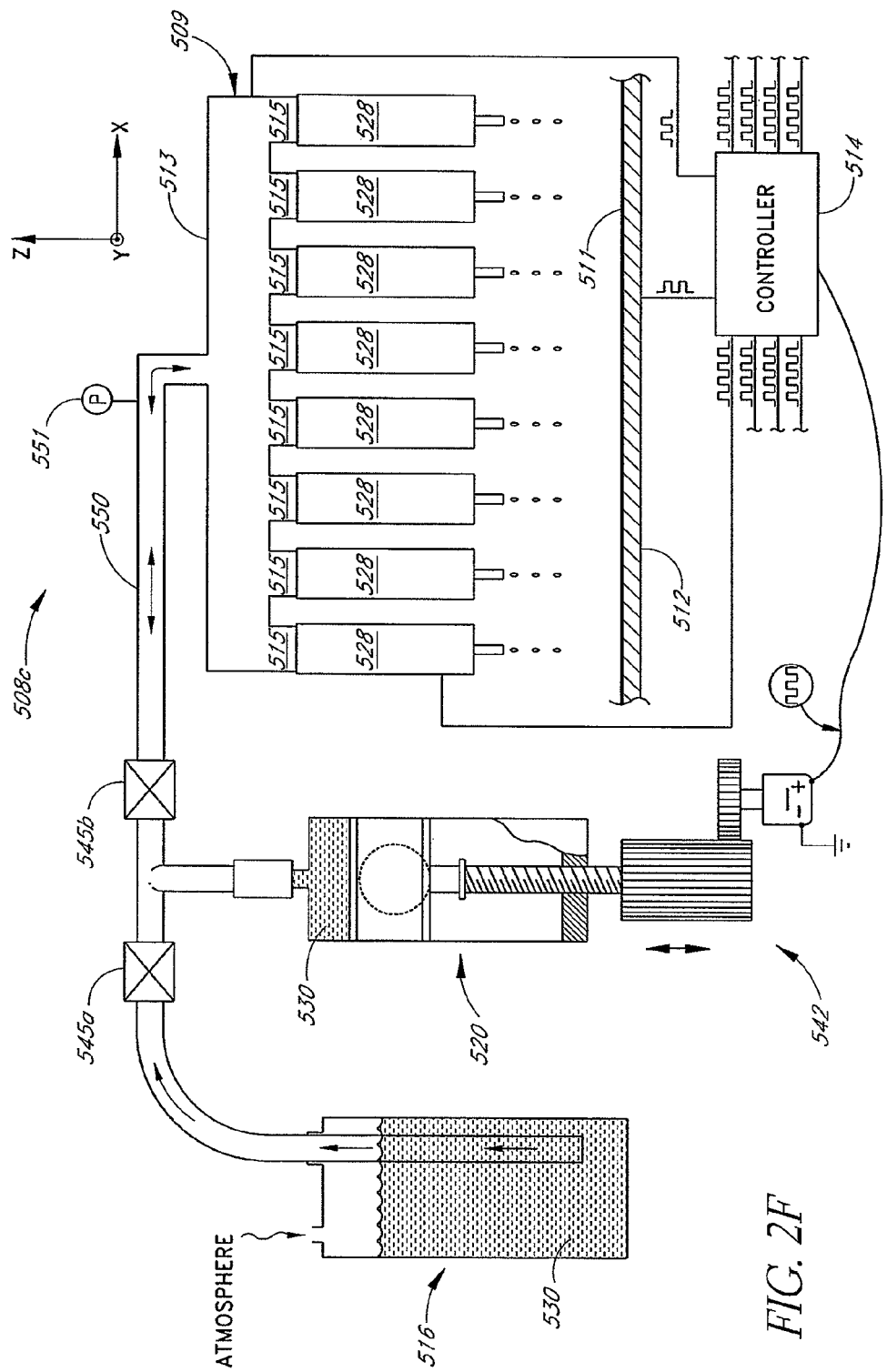
FIG. 2F is a simplified view of a dispensing apparatus with a manifold and illustrating features and advantages in accordance with certain embodiments of the invention.

FIG. 2F is a simplified view of a dispensing apparatus 508c comprising a manifold 509 connected to a plurality of dispensers 528. The manifold generally comprises a main supply line 513 in fluid communication (hydraulically coupled) with a plurality of independent channels 515 each of which is in fluid communication (hydraulically coupled) with a respective one of the dispensers 528. A positive displacement syringe pump 520 is in fluid communication (hydraulically coupled) with the manifold 509 via the feedline 550. Reagent(s) can be first aspirated and then dispensed or a single reagent may fill the system, as discussed above.

Still referring in particular to FIG. 2F, relative motion is provided between the substrate or target 511 and the dispensing channels 528. The dispensers 528 and/or the platform 512 are movable in the X, X-Y or X-Y-Z directions to allow for precision dispensing at predetermined locations. Multiple targets 511 may be placed on the table 512, as needed or desired. The dispensers 528 are in the form of multiple dispense channels spaced from one another by predetermined distance(s). More than one manifold may be utilized, as needed or desired.

The dispensers 528 (FIG. 2F) can be individually (serially or sequentially) operated or substantially simultaneously (parallely) or a combination thereof, as needed or desired. A linear (1×N) or two-dimensional (M×N) array of dispensers 528 may be used with efficacy. A central or main controller 514 is used to control and coordinate the actuations of the pump 520, dispensers 528 and relative movement between the target 511 and dispense channels 128. Certain embodiments of a multi-channel aspirate-dispense system comprising a manifold are described in U.S. Patent Application Publication No. US 2003/0215957 A1, entitled MULTI-CHANNEL DISPENSING SYSTEM, the entirety of which is hereby incorporated by reference herein.

Advantageously, and as shown in FIG. 2F, the use of a manifold 509 allows only one pump 520 to meter fluid to and from a plurality of dispensers 528. Desirably, this saves on cost. Moreover, balanced and controlled output can be achieved by adjusting the frequency and/or duty cycle of one or more of the dispensers 528 to compensate for any variations in flow resistances between channels.

Figure 2G:
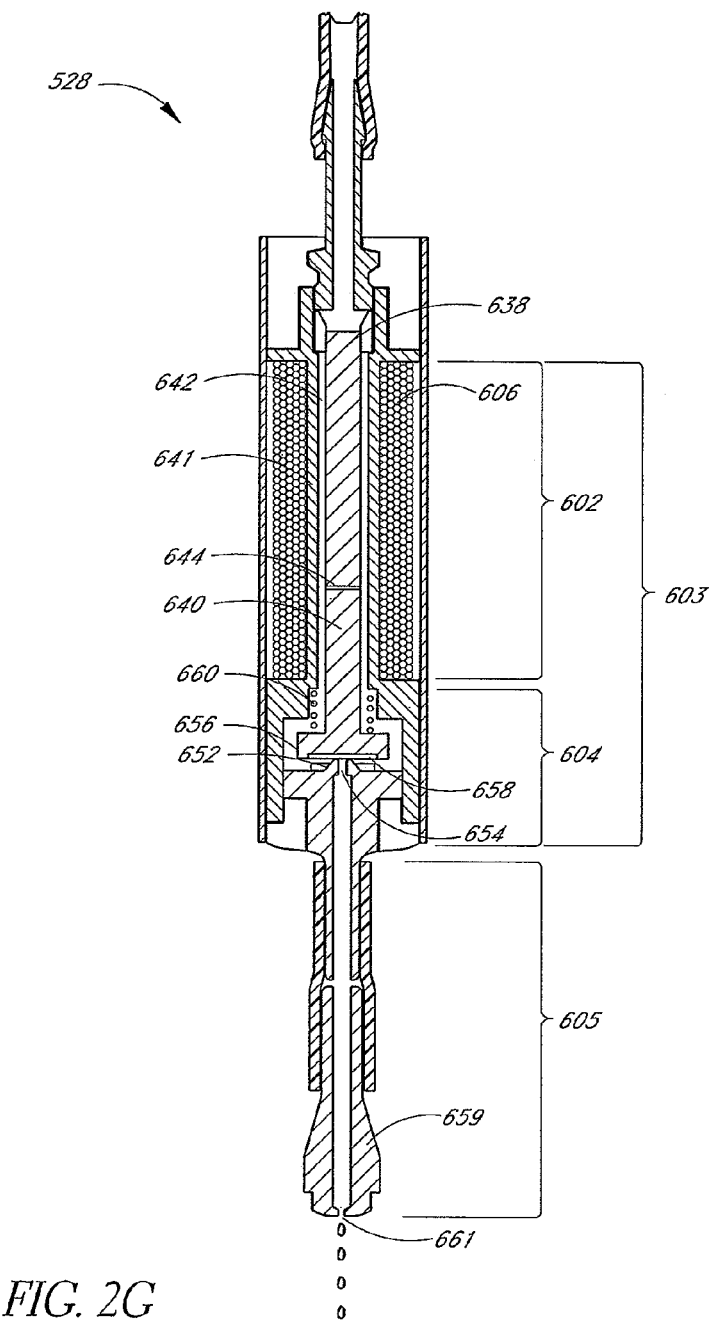
FIG. 2G is a cross-sectional view of a solenoid valve dispensing head for use in accordance with any of the embodiments of FIGS. 2A-2F.

FIG. 2G is a cross-sectional view of one embodiment of a solenoid valve dispensing head 128 for use, as applicable, with the dispensing (and/or aspiration) systems as described herein. Solenoid valve dispensers of the type shown in FIG. 3A are commonly used for ink-jet printing applications and are commercially available from sources such as The Lee Company of Westbrook, Conn. Other suitable drop-on-demand dispensers and valves may be efficaciously used, as needed or desired.

The drop-on-demand dispenser 528 generally comprises a solenoid portion 602, a valve portion 604 and a tube, capillary, tip or nozzle portion 605. The solenoid portion 602 and the valve portion 204 in combination can be termed a drop-on-demand valve, a solenoid-actuated valve or a micro-solenoid valve 603.

The solenoid portion 602 comprises an electromagnetic coil or winding 606, a static core 638 and a movable plunger 640. The static core 638 and movable plunger 640 are disposed within a hollow cylindrical sleeve 641 and are preferably spaced at least slightly away from the inner walls of the sleeve 641 so as to form an annular passage 642 there between through which the reagent 530 or other liquid to be dispensed may flow. The static core 638 and movable plunger 640 are preferably formed of a ferrous or magnetic material, such as an iron alloy, and are separated by a small gap 644. Those skilled in the art will appreciate that when the solenoid coil 606 is energized, for example by a current or voltage, a magnetic field is created which draws the plunger 640 upward toward the static core 638, closing the gap 644 and opening the valve 634.

The valve portion 604 comprises a valve seat 652, having an orifice opening 654, and a stopper 656 having a valve face 658 adapted to seal against the valve seat 652. The stopper 656 is in electro-mechanical communication with the plunger 640 and is spring biased toward the valve seat 652 via coil spring 660. Again, those skilled in the art will readily appreciate that as the plunger 640 moves up and down, the valve 234 will open and close, accordingly, hence providing selective fluid communication with the tip 605. Moreover, each time the valve 234 opens and closes, a volume of liquid is allowed to escape through the valve orifice 654. This, in conjunction with the metering of fluid by the pump 520, forms an energy pulse or pressure wave which causes a droplet of liquid to be ejected from the exit orifice 661 of the nozzle tip 659.

As indicated above, preferably, the pump 520 (see, for example, FIG. 2C) is a positive displacement pump and is provided in series with the solenoid valve dispenser 528. Configuring the dispensing system in this manner has the benefit of forcing the solenoid valve dispenser 528 to admit and eject a quantity and/or flow rate of reagent as determined solely by the positive displacement pump 520, with which it is hydraulically in series. For example, the syringe pump could be instructed to deliver a flow rate of 1 microliter per second of reagent to the solenoid valve dispenser 528 at a steady rate. As the valve stopper 556 is, opened and closed at a given frequency and duty cycle a series of droplets are formed which will exactly match the desired flow rate. The syringe pump acts as a forcing function for the entire system, ensuring that the desired flow rate is maintained regardless of the duty cycle or frequency of the dispensing valve.

Advantageously, within a certain operating range the frequency and/or velocity of the droplets can be adjusted without affecting the flow rate of reagent simply by changing the frequency and/or duty cycle of the energizing pulses 582 (FIG. 2C) provided to the solenoid valve dispenser 528. Of course, there are physical limitations of valve open time or duty-cycle necessary to achieve stable droplet formation. If the open time is too short relative to the flow rate, the pressure will increase and possibly prevent the valve dispenser 528 from functioning properly. If the open time is too long relative to the flow rate, then drop formation may be impaired or may not be uniform for each open/close cycle. Nevertheless, for a given flow rate of reagent 530 provided by the syringe pump 520 there will be a range of compatible frequencies and/or valve open times or duty-cycles in which stable dispensing operations may be achieved at the desired flow rate and droplet size. This range may be determined experimentally for a given production set up.

Certain embodiments of a solenoid actuated dispenser are described in U.S. Pat. No. 6,537,505 B1, entitled REAGENT DISPENSING VALVE, the entirety of each one of which is hereby incorporated by reference herein.

Those skilled in the art will recognize that other types of dispensers and valve actuation devices exist and may be used with efficacy. These may include, for example, but are not limited to piezoelectric dispensers, fluid impulse dispensers, heat actuated dispensers, air brush dispensers, and the like.

Figure 2H:
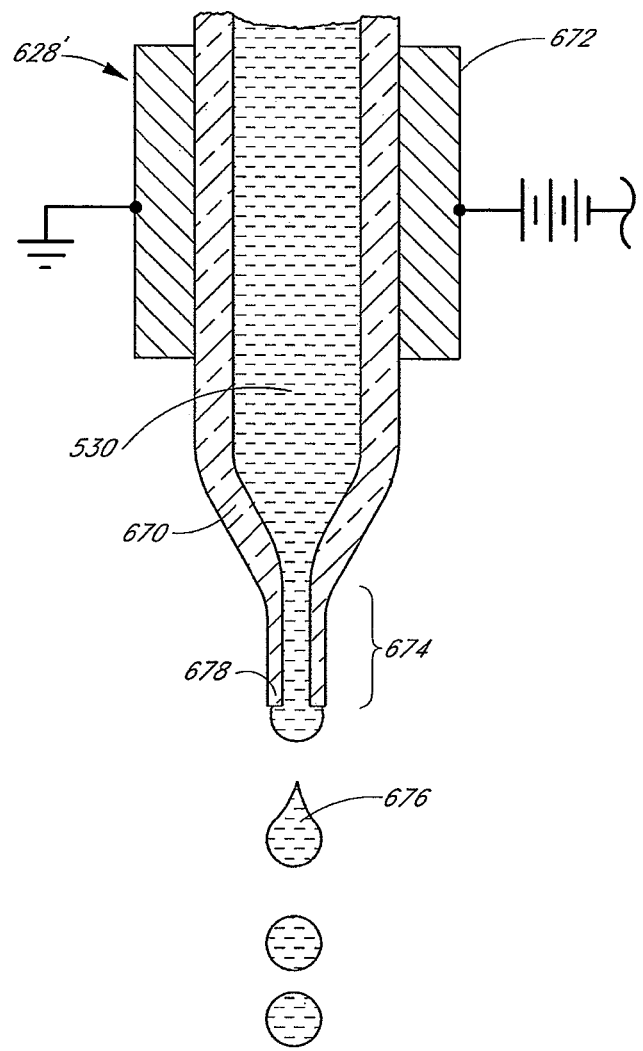
FIG. 2H is a cross-sectional view of a piezo electric dispensing head for use in accordance with any of the embodiments of FIGS. 2A-2F.

FIG. 2H shows a cross-sectional view of a piezoelectric dispenser 528' which also has advantageous use in accordance with certain embodiments of the invention. The piezoelectric dispenser 528' generally comprises a capillary tube 670 made of glass or other suitable material and a piezoelectric constrictor 672 disposed around the capillary tube 670, as shown. The capillary tube 670 has a nozzle portion 674 of a reduced diameter. When the capillary tube 670 is constricted by the piezoelectric constrictor 672, droplets 676 are formed at the exit orifice 678 of the nozzle portion 674. Advantageously, the dynamics of the piezoelectric dispenser 628' are such that it may be able to operate at even higher frequencies and shorter duty cycles than typical solenoid valve dispensers, resulting in even smaller droplets 676. Operation of the piezoelectric dispenser 628' in terms of adjusting droplet size, frequency, velocity and flow rates is substantially the same or similar to that described in connection with the solenoid valve dispenser 628 of FIG. 2G and, therefore, will not be repeated here.

Figure 2J:
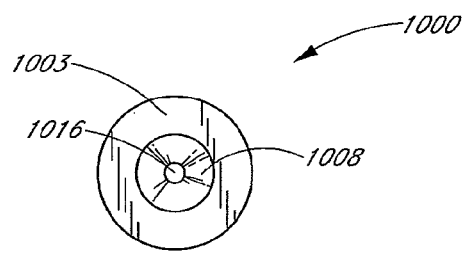
FIG. 2J is a top view of the tip of FIG. 2I.
Figure 2I:
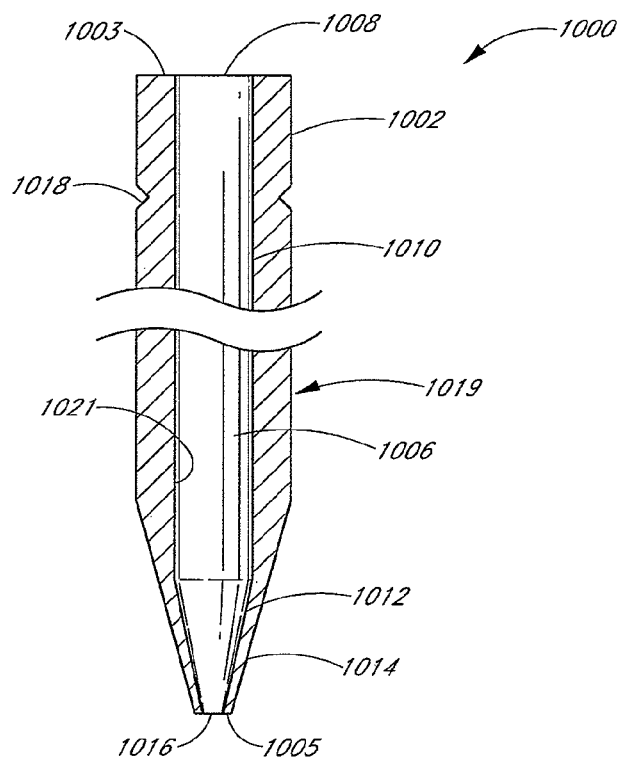
FIG. 2I is a cross-sectional view of a dispensing tip for use in accordance with any of the embodiments of FIGS. 2A-2H.
Figure 2K:
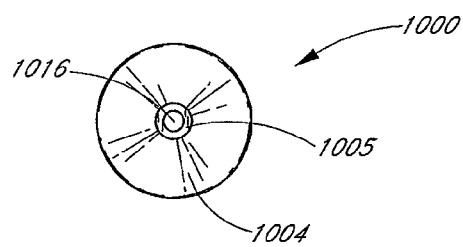
FIG. 2K is a top view of the tip of FIG. 2I.

FIGS. 2I, 2J and 2K show different views of a non-contact dispensing capillary tip or tube 1000 having features and advantages in accordance with certain embodiments of the invention. The dispensing tip 1000 may be incorporated into any of the dispensing systems taught or suggested herein, as applicable. Embodiments of such tips are disclosed in U.S. Pat. No. 6,551,557 B1, entitled TIP DESIGN AND RANDOM ACCESS ARRAY FOR MICROFLUIDIC TRANSFER, the entirety of which is hereby incorporated by reference herein.

In the illustrated embodiment of FIGS. 2I-2K, the tip 1000 is generally cylindrical in shape and comprises a non-tapered upper portion or shank 1002 with an upper end 1003, a tapered lower portion/outer surface 1004 with a lower end 1005 and an inner lumen or through cavity 1006. The inner lumen 1006 is generally cylindrical in shape with a top opening 1008, a non-tapered upper portion 1010, and a tapered lower portion/inner surface 1012 to form a nozzle 1014 having an orifice or opening 1016. Advantageously, the outer taper 1004 leads to less accumulation of fluid on the tip outer surface, for example, during aspiration. Also, advantageously, the inner taper 1012 is a desirable shape for capillary action, and reduces fluid mixing during aspiration and reduces the precipitation of gaseous bubbles within the fluid during aspirate-dispense operations.

Optionally, as shown in FIG. 2I, the tip 1000 may further include a generally circumferential groove, slot or notch 1018 on the non-tapered upper portion 1002. The slot 1018 is generally V-shaped. The notch 1018 advantageously provides an easy break point in the case of accidental hard or jarring contact between the tip 1000 and a contacting surface of the fluid source or target.

Preferably, the tip 1000 is fabricated from a ceramic material, and more preferably, from alumina. Advantageously, the ceramic material provides chemical inertness since alumina is inert to most chemical solvents. Moreover, the ceramic material provides robustness, and hence can withstand extreme mechanical stress. In other embodiments, the tip 1000 can be fabricated from a wide variety of materials with efficacy such as metals, alloys, and plastics, as required or desired, giving due consideration to the goals of providing chemical inertness and robustness.

In one embodiment, the outer surface 1019 (FIG. 2I) of the tip 1000 is coated with a thin film or coating that is not only chemically inert and mechanically robust but is also hydrophobic to most fluids such as aqueous reagents, DMSO, and other common solvents. The film helps in keeping the tip 1000 dry and also improves the microfluidic or sub-microfluidic transfer. Preferably, the film comprises a wear-resistant material so that it has an enhanced lifetime. Suitable films or coatings include silicon nitride, silicon carbide, titanium nitride, among others. The film or coating can be applied by a variety of methods such as plasma deposition and sputtering, among others, as is known in the art. A suitable hydrophobic coating may also be applied to selected portions of the inner surface 1021 of the tip 1000, as needed or desired.

The tip 1000 may be dimensioned in a wide variety of manners with efficacy, as required or desired, giving due consideration to the goals of providing reliable and repeatable microfluidic and sub-microfluidic transfer of fluid. In one embodiment, the tip 1000 has a length of 16 mm and an internal volume of about 20 microliters (µL). In some embodiments, the inner diameter at the nozzle end of the tip 1000 is in the range from about 20 to 180 microns (µm) and the outer diameter is in the range from about 50 to 400 µm or more. In other embodiments, the inner diameter at the nozzle end of the tip 1000 is in the range from about 100 to 300 µm and the outer diameter is in the range from about 400 to 900 µm.

Figure 2L:
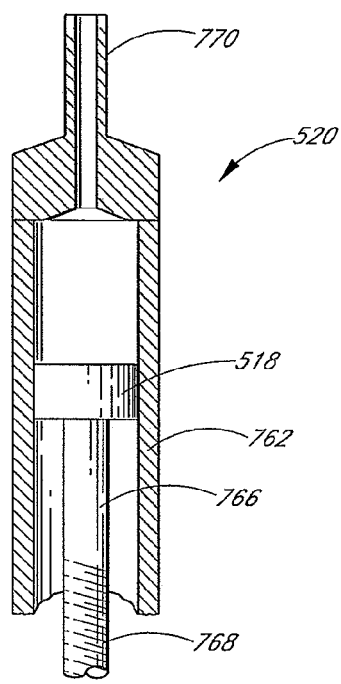
FIG. 2L is a cross-sectional view of a positive-displacement syringe pump for use in accordance with either of the embodiments of FIGS. 2A-2F.

Referring in particular to FIGS. 2C and 2L, the pump 520 is preferably a high-resolution, positive displacement syringe pump hydraulically coupled to the dispenser 528. Alternatively, pump 520 may be any one of several varieties of commercially available pumping devices for metering precise quantities of liquid. A syringe-type pump 520, as shown for example in FIG. 2C, is preferred because of its convenience and commercial availability. A wide variety of other direct current fluid source means may be used, however, to achieve the benefits and advantages as disclosed herein. These may include, without limitation, rotary pumps, peristaltic pumps, squash-plate pumps, and the like, or an electronically regulated fluid current source.

As illustrated in FIG. 2L, a suitable syringe pump 520 generally comprises a syringe housing 762 of a predetermined volume and a plunger 518 which is sealed against the syringe housing by O-rings or the like (not shown). The plunger 518 mechanically engages a plunger shaft 766 having a lead screw portion 768 adapted to thread in and out of a base support (not shown). Those skilled in the art will readily appreciate that as the lead screw portion 768 of the plunger shaft 766 is rotated the plunger 518 will be displaced axially, forcing reagent 530 from the syringe housing 762 into the exit tube 770. Any number of suitable motors or mechanical actuators may be used to drive the lead screw 768. Preferably, a pump driver 542 including a stepper motor (FIG. 2C) or other incremental or continuous actuator device is used so that the amount and/or flow rate of reagent 530 can be precisely regulated.

Several suitable syringe pumps are commercially available. One such syringe pump is the Bio-Dot CV1000 Syringe Pump Dispenser, available from BioDot, Inc. of Irvine, Calif. This particular syringe pump incorporates an electronically controlled stepper motor for providing precision liquid handling using a variety of syringe sizes. The CV1000 is powered by a single 24 DC volt power supply and is controlled via an industry-standard RS232 or RS485 bus interface. The syringe pump may have anywhere from 3,000-24,000 steps, although higher resolution pumps having 48,000-192,000 steps or more may also be with efficacy. Higher resolution pumps, such as piezoelectric motor driven pumps, may also be used to provide even finer resolutions as desired.

The lead screw 768 (FIG. 2L) may optionally be fitted with an optical encoder or similar device to detect any lost steps. Alternatively, the lead screw of the metering pump can be replaced with a piezoelectric slide to provide both smaller volume increments and also faster acceleration/deceleration characteristics. Multiple syringe pumps may also be used in parallel, for example, for delivering varying concentrations of reagent 530 and/or other liquids to the dispenser or for alternating dispensing operations between two or more reagents. This could have application, for instance, to ink jet printing using one or more colored inks or liquid toners.

Syringe size may vary from less than 50 microliters (μL) to 50 milliliters (mL), or more as needed. The minimum incremental displacement volume of the pump will depend on the pump resolution and syringe volume. For example, for a syringe housing volume of 50 μl, and 192,000 step resolution pump the minimum incremental displacement volume will be about 0.260 nanoliters (nL). Minimum incremental displacement volumes from about 0.25 nanoliters to about tens of milliliters (mL) are preferred, although higher or lower incremental displacement volumes may also be used while still enjoying the benefits disclosed, taught or suggested herein.

Of course, a wide variety of other positive displacement or "direct current" fluid sources may also be used to achieve the benefits and advantages as disclosed herein. These may include, for example and without limitation, rotary pumps, peristaltic pumps, squash-plate pumps, pumps incorporating hydraulic or electronic feedback control and the like.

In some embodiments, one or more pressure sensors 551 are provided in conjunction with the aspirate-dispense apparatuses 508 (FIG. 2C), 508a (FIG. 2D), 508b (FIG. 2E) and 508c (FIG. 2F) to monitor the system pressure and provide diagnostic information about various fluid and flow parameters within the hydraulic system. The one or more pressure sensors 551 are provided at appropriate locations on the respective systems. In one embodiment, the pressure sensors 551 are placed intermediate the syringe pump(s) 520 and the dispenser(s) 528, such as on the feedline 550 (see, for example, FIG. 2C). Alternatively, or in addition, the pressure sensor(s) 551 can be situated at the dispenser(s) 528 such as on the valve portion(s) 604.

It should be noted that for purposes of brevity of disclosure some of the discussion here refers to a single pump-dispenser apparatus. Of course, it should be understood that this can be suitably extrapolated to include operation of the embodiments of arrays of pump-dispenser systems, for example, the systems of FIGS. 2D and 2E. Moreover, and as one of ordinary skill in the art will appreciate, it is further extendable with some modifications to manifold systems, for example, the manifold dispensing system of FIG. 2F.

Referring in particular to FIG. 2C, the skilled artisan will recognize that the hydraulic coupling between the pump 520 and the dispenser 528 of the aspirate-dispense system 508 provides for the situation where the input from the pump 520 exactly equals the output from the dispenser 528 under steady state conditions. Therefore, the positive displacement system uniquely determines the output volume of the system while the operational dynamics of the dispenser 528 serve to transform the output volume into ejected drop(s) having size, frequency and velocity.

It has been discovered, however, that within the system there exists an elastic compliance partly due to the compliance in the delivery tubing and other connectors and components, and partly due to gaseous air bubbles that may have precipitated from air or other gases dissolved in the system and/or source fluid. As a result of this elastic compliance, initial efforts to dispense small quantities of fluid resulted in gradually overcoming the system compliance and not in dispensing fluid or reagent. Once this elastic compliance was overcome, a steady state pressure was found to exist and complete dispensing occurred thereafter.

A discussion of the theoretical predicted behavior and theoretical flow models relating to positive displacement dispensing and aspirating systems can be found in U.S. Patent Application Publication No. US 2003/0207464 A1, entitled METHODS FOR MICROFLUIDIC ASPIRATING AND DISPENSING, U.S. Patent Application Publication No. US 2003/0215957 A1, entitled MULTI-CHANNEL DISPENSING SYSTEM, and U.S. Pat. No. 6,589,791 B1, entitled STATE-VARIABLE CONTROL SYSTEM, the entirety of each one of which is hereby incorporated by reference herein.

Thus, by providing a positive displacement pump 520 (FIG. 2C) in series with a dispenser 528 (FIG. 2C) has the benefit of forcing the dispenser 528 to admit and eject a quantity and/or flow rate of reagent as determined solely by the positive displacement pump 520 for steady state operation. In essence, the syringe pump 520 acts as a forcing function for the entire system, ensuring that the desired flow rate is maintained regardless of the duty cycle, frequency or other operating parameters of the dispensing valve, such as the solenoid-actuated valve 528 (FIG. 2G). With such configuration and at steady state operation one does not really care what the pressure in the system is because it adjusts automatically to provide the desired flow rate by virtue of having a positive displacement or direct current fluid source as a forcing function for the entire system.

However, this does not address the situation of latent and/or transient pressure variations, such as associated with initial start-up of each dispense and aspirate function. In particular, it has been discovered that the pressure in the system is of critical concern for non-steady state operation involving aspirating or dispensing of microfluidic quantities, typically greater than about 1 nanoliter (nL) and less than about 50 microliters (μL), of liquid reagents or other fluids. Specifically, for an aspirate function it has been discovered that a system pressure close to or below zero is preferred, while for a dispense function it has been discovered that a finite and positive predetermined steady state pressure is preferred.

The transitions between various modes (aspirate, dispense, purge/wash) and/or flow rates or other operating parameters can result in pressure transients and/or undesirable latent pressure conditions within the positive displacement dispense/aspirate system. Purge and wash functions usually entail active dispensing in a non-target position. In some cases, when the same reagent is to be aspirated again, several aspirate-dispense cycles can be performed before executing a purge or wash function. Also, sometimes a purge function may have to be performed during a dispense function, for example, to alleviate clogging due to the precipitation of gaseous bubbles within the system and/or source fluid. Moreover, the accumulation of these bubbles can change the system compliance over time, and hence the desired optimum dispensing pressure.

Figure 2M:
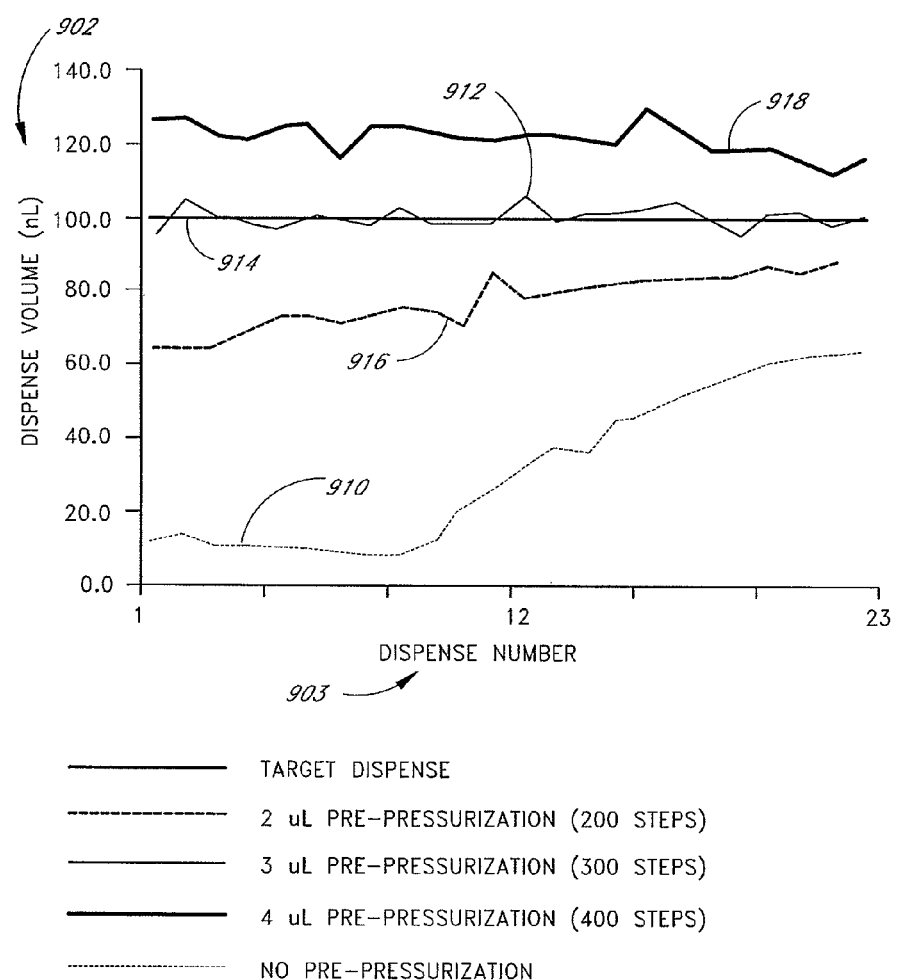
FIG. 2M is a graph illustrating initial (non-steady-state) dispense volumes versus target dispense volumes for a reagent dispensing method and apparatus in accordance with one embodiment of the invention and showing the effects of reagent pre-pressurization.

For example, line 910 in FIG. 2M illustrates transient dispense effects caused by initial start-up of a dispensing system 508 (FIG. 2C) in which no pressure compensation scheme is utilized. The x-axis 903 represents the dispense number or number of dispenses and the y-axis 902 represents the dispense volume, in nanoliters (nL) of each droplet or droplets dispensed. Line 914 in FIG. 5 represents the target dispense volume of 100 nL.

As can be seen by the data of FIG. 2M, the non-pressure compensated (non-steady state) dispensed volume represented by line 910 is substantially smaller than the target dispense volume of 100 nL (line 914) since the system pressure at start-up is substantially lower than the desired steady state and/or predetermined pressure. The non-pressure compensated dispense volume (line 910) can be lower by a factor of about ten compared to the target dispense volume (line 914). Moreover, even after 23 dispenses (see FIG. 2M) the dispensed volume (line 910) is still below the target volume (line 914).

Line 912 represents a series of about 100 nL dispenses performed in accordance with one embodiment, wherein an optimized pressurizing (300 steps of the syringe plunger 518—shown in FIGS. 2C and 2L) is performed prior to dispensing, that is, with the valve 604 (FIGS. 2C and 2G) closed. The pressure compensation scheme provides dispense volumes (line 912) which are in substantially close conformity with the target dispense volume (line 914) of 100 nL. Underpressurization (200 steps of the syringe plunger 518), as illustrated by line 916, can result in dispense volumes that are undesirably less than the target dispense volume 914. Similarly, as illustrated by line 918, over-pressurization (400 steps of the syringe plunger 518) can result in dispense volumes that are undesirably more than the target dispense volume 914.

Certain embodiments of pressure compensation or adjustment, for example, prior to dispense and aspirate functions, are described in U.S. Patent Application Publication No. US 2003/0207464 A1, entitled METHODS FOR MICROFLUIDIC ASPIRATING AND DISPENSING, U.S. Patent Application Publication No. US 2003/0215957 A1, entitled MULTI-CHANNEL DISPENSING SYSTEM, and U.S. Pat. No. 6,589,791 B1, entitled STATE-VARIABLE CONTROL SYSTEM, the entirety of each one of which is hereby incorporated by reference herein.

In brief, to set the system pressure to a predetermined and/or steady state dispense pressure, the syringe plunger 518 (FIGS. 2C and 2L) is typically incremented (or possibly decremented) by a predetermined amount to build up (or reduce) pressure, as described above in connection with FIG. 2M. Similarly, to set the pressure to a predetermined and/or steady state aspirate pressure, the syringe plunger 518 (FIGS. 2C and 2L) is typically decremented (or possibly incremented) by a predetermined amount. Of course, pre-dispenses of reagent or system fluid in a waste position may be performed to raise or lower the system pressure, as needed or desired.

One or more pressure sensors, such as the pressure sensor(s) 551 (FIGS. 2C-2F) are used to monitor the system pressure and ensure that the correct operational pressure(s) are achieved. Any one of a number of commercially available pressure sensors may be efficaciously used. The pressure sensors 551 are preferably differential type devices.

The desired steady state dispense pressure can be estimated from flow resistances and/or prior steady state pressure measurements or transient pressure measurements. A number of parameters can affect the selection of this pressure, including the desired droplet volume and system compliance, among other fluid, flow, system and operational parameters.

Some embodiments of methods for estimating this steady state dispense pressure are described in U.S. Patent Application Publication No. US 2003/0207464 A1, entitled METHODS FOR MICROFLUIDIC ASPIRATING AND DISPENSING, U.S. Patent Application Publication No. US 2003/0215957 A1, entitled MULTI-CHANNEL DISPENSING SYSTEM, and U.S. Pat. No. 6,589,791 B1, entitled STATE-VARIABLE CONTROL SYSTEM, the entirety of each one of which is hereby incorporated by reference herein.

The steady state pressure can also be estimated from previously formulated parametric tables or charts based on one or more fluid, system, flow and operational parameters. Regression analysis techniques may be used to estimate the optimum dispense pressure. Alternatively, or in addition, the dispense pressure may be predetermined for a given production set-up.

In some embodiments, the aspirate-dispense systems disclosed herein are configured to minimize the formation and accumulation of gaseous bubbles within the fluid residing in the system, and particularly in the dispensers 528 (FIGS. 2C-2F), feedline 550 and manifold 509 (FIG. 2F). For example, to minimize bubble formation, the system components be configured such that the fluid movements within the system avoid sharp local pressure drops, and hence gaseous bubble precipitation. Additionally, the components may be configured such that none or few "dead spots" are encountered by the fluid, thereby discouraging bubble accumulation within the system. These configurations can utilize suitably tapered inner cavities or lumens within the valve portion 604, tip 605 and/or nozzle 659 to provide relief from gaseous bubble precipitation and/or "dead spots."

In one embodiment, a suitably configured bubble trap (not shown) is provided in fluid communication with the dispenser 528 (see, for example, FIG. 2C). The trap encourages the migration of gaseous bubbles to collect within the trap and prevents undesirable bubble accumulation within the aspirate-dispense system.

In some embodiments, the dispensing operation takes place on-the-fly, that is without stopping the motion of the X-Y table (see U.S. Pat. No. 6,063,339, incorporated by reference herein). To accommodate this on-the-fly dispensing without compromising accuracy, precision or repeatability, the controller 514 calculates a phase adjustment for each dispense cycle. The phase adjustment is such as to advance (or retard) the timing of the valve opening and closing so that the dispensed droplet of reagent lands at the desired location on the substrate 511 (or at a desired offset location), taking into account its anticipated trajectory.

Those skilled in the art will recognize that the magnitude of the necessary or desired phase adjustment will depend, among other things, on a number of system input and output parameters and behavioral characteristics, including the desired drop offset (if any), the vertical distance between the dispenser nozzle 605 and the surface of the substrate 511, the velocity and/or acceleration of the dispenser 528 and/or the substrate 511 relative to one another, the velocity of the dispensed droplets, ambient temperature and humidity, and other controlled and/or uncontrolled factors. While certain of these parameters or characteristics can be isolated and studied such that their impact on the necessary phase adjustment is fairly predictable, other parameters or characteristics can neither be isolated nor predicted. It is however contemplated, that precise phase adjustments can be determined experimentally for a given production set up either before or during production such that a high degree of accuracy, precision and repeatability is attained during long production runs.

In some embodiments, a modulated mode of valve operation is utilized. As discussed above, the syringe positive displacement and solenoid valve 603 combination results in the syringe pump 520 determining the drop volume and the solenoid valve aiding in the ejection of a drop from the dispense channel nozzle 659 (FIG. 2G). The modulation mode of operation takes place when the solenoid drive current for open/close of the valve 603 is driven at higher frequencies than allowed for a full open and close situation. In this case, the valve plunger face 658 does not seal against the valve seat 652 but oscillates in the open position. This oscillation energy further facilitates the ejection of the fluid from the tip 605 and/or nozzle 659 through the orifice 661. The ejection format can be in the form of a continuous jet with volume oscillations to individual drops. This mode of operation can typically be operated at much higher frequencies compared to the "burst" mode since the valve does not fully close. For example, theses frequencies can be in the range of about 6000 Hz.

The modulation mode can advantageously provide high speed dispensing of fluid using small drop sizes. This provides a robust and accurate delivery of fluid as compared to some lower frequency operations. This method also allows for selection of parameters that eliminates the need for pressure adjustment to achieve steady state dispensing between desired droplet volume changes. The modulation mode provides robust and accurate delivery of single drops over a wide range of ejected drop volumes, ranging from about 2 nL or less to over 100 nL.

It will be appreciated that any of the dispensing (and aspirating) systems taught or suggested herein can employ a number of optional features with efficacy, as needed or desired. The include, without limitation: humidity control; cooling unit(s); clean room enclosure(s); camera(s); software options; degasser(s) (e.g., helium vacuum, in line); vacuum pump(s); wash station(s); vision system(s); and barcode reader(s).

U.S. Patent Application Publication No. US 2005/0056713 A1, the entirety of which is hereby incorporated by reference herein, discloses helium degassing methods and systems. In certain embodiments, such a method is used to degas the fluids utilized in connection with the dispensing systems disclosed herein. The method generally comprises pressurizing a reservoir containing a reagent to a degassing high first pressure by providing a static pressure from a helium source over the reagent to degas the reagent. The first pressure in the reservoir is reduced to a low second pressure. The reservoir is vented to ambient conditions. A pump connected to the reservoir is operated to draw the reagent from the reservoir into the pump. A tip having a dispense nozzle and a through lumen is provided with the tip being connected to the pump. A predetermined quantity of the reagent is metered from the pump to the tip to dispense one or more droplets of the reagent from the nozzle onto or into a target.

U.S. Patent Application Publication No. US 2003/0228241 A1, the entirety of which is hereby incorporated by reference herein, describes an apparatus for liquid sample handling which has efficacy in conjunction with some of the liquid dispensing and aspirating embodiments disclosed herein. The apparatus generally comprises a plurality of hollow capillaries, a housing which retains the capillaries in their desired orientation and means to effect sample removal from the capillaries. Each capillary is open at both ends and has a defined internal volume. On contact of an open end of the capillary with a sample a defined volume of sample is drawn up into the capillary by capillary action. The capillaries can be arranged in a one-dimensional array or a two-dimensional array. Pressurized gas is provided by means of a control valve and suitable pipework or through an orifice to achieve droplet dispensing.

Some Embodiments of Array Features and Details

Array Density

For some embodiments, the expected or typical range of spots per array for diagnostic applications is in the range from about 10 to about 3000. In certain embodiments, with the largest number of applications for high volume diagnostics, the expected or typical range of spots per array is in the range from about 100 to about 200 spots or dots per array or lower.

In order to manufacture such arrays (100-200 spots/array) with production rates in the range of 1-1,000 million units per year, some embodiments contemplate utilization of in-line types of approaches using web or carrier formats for discrete substrates. Advantageously, this would allow the use of highly parallel dispensing strategies to allow large numbers of dispensers to operate in parallel to meet the required or desired production rates.

For array densities above 200 the same approach can be taken but the number of dispensers increases as does the cost. For example, if the cost per dispense channel is assumed to be about $10,000, then 3,000 channels would cost $30,000,000. Hence, a different approach is desirable to save on cost.

In some embodiments, for array densities above 200, a smaller number of channels could be used, such as 150 channels. This would involve 20 aspirate/dispense (A/D) operations and hence reduce throughput by a factor of 20. It would also entail running the substrates 20 times under the dispenser configuration which involves precise repositioning.

Thus, depending on the array density and the particular application and budgetary constraints, certain embodiments of the invention involve a judicious choice of the number of dispensers or dispense channels to optimize the throughput while maintaining a balance between cost and time. Hence, the particular dispense configuration can be customized and/or optimized with efficacy, as needed or desired.

FIGS. 3-5 show exemplary embodiments of low density and medium density array format designs or concepts. These figures show respective substrates or substrate assemblies 10 (10a, 10b, 10c) comprising respective arrays or microarrays 12 (12a, 12b, 12c).

FIG. 3 shows a 16 (4×4) spot array or microarray 12a formatted in a generally square (4×4) configuration with a plurality of spots 14a on a substrate surface or medium 16a such as a glass slide or the like. One or more fiducial targets, indicia or marks 18a can be provided to facilitate proper alignment and/or orientation, such as during processing, with efficacy, as needed or desired.

The dimensions shown in FIG. 3 are in millimeters (mm). In one embodiment, the 16 spot density array or microarray 12a has spots or dots located on (or spaced by) about 2 mm centers.

FIG. 4 shows a 40 (5×8) spot array or microarray 12b formatted in a generally rectangular (5×8) configuration with a plurality of spots 14b on a substrate surface or medium 16b such as a glass slide or the like. One or more fiducial targets, indicia or marks 18b can be provided to facilitate proper alignment and/or orientation, such as during processing, with efficacy, as needed or desired.

The dimensions shown in FIG. 4 are in millimeters (mm). In one embodiment, the 40 spot density array or microarray 12b has spots or dots located on (or spaced by) about 2 mm centers.

FIG. 5 shows a 3,000 (30×100) spot array or microarray 12c formatted in a generally rectangular (30×100) configuration with a plurality of spots 14c on a substrate surface or medium 16c such as a glass slide or the like. One or more fiducial targets, indicia or marks 18c can be provided to facilitate proper alignment and/or orientation, such as during processing, with efficacy, as needed or desired.

The dimensions shown in FIG. 5 are in millimeters (mm). In one embodiment, the 3,000 spot density array or microarray 12c has, spots or dots located on (or spaced by) about 2 mm centers.

The spot spacing for these exemplary array substrates 10 allows for the arrays 12 to be desirably made with drop sizes, which in some embodiments are, in the range from about 100 picoliters (pL) to about 50 nanoliters (nL), including all values and sub-ranges therebetween. In certain embodiments, the drop size or volume is in the range from about 20 picoliters (pL) to about 1 microliter (µL), including all values and sub-ranges therebetween. Any of the dispensing techniques taught or suggested herein, among others, may be used to dispense these drop sizes.

In some embodiments, a solenoid actuated dispensing technology is used to form the arrays 12 by dispensing drop sizes in the nanoliter range, for example, the dispensing systems of FIGS. 2A-2F. In some embodiments, a piezo or piezoelectric dispensing technology is used to form the arrays 12 by dispensing drop sizes in the picoliter range, for example, the dispensing systems of FIGS. 1A-1C.

In certain embodiments, any of the dispensing technologies taught or suggested herein, but not limited to, U.S. Pat. Nos. RE38,281 E, 6,063,339, 6,599,479 B1, and US 2004/0219688 A1, the entirety of each one of which is hereby incorporated by reference herein and comprises a part of the present patent specification/application, can be efficaciously used to form the array substrates 10 comprising arrays 12 with dispensed drop sizes in the picoliter and/or nanoliter range, as needed or desired.

The array substrates 10a, 10b, 10c comprising respective arrays 12a, 12b, 12c, in some embodiments, share a common substrate size such that the substrates 10a, 10b, 10c or respective substrate surfaces or mediums 16a, 16b, 16c have substantially the same size. This desirably facilitates in overall efficiency in substrate handling. In certain embodiments, one or more of the substrates 10 (10a, 10b, 10c) or substrate surfaces or mediums 16 (16a, 16b, 16c) has a size which is about the same as the size of a standard glass slide.

Hybridization

In general, the hybridization process comprises up to three steps, acts or elements. These, without limitation, are: (a) blocking for protein arrays, (b) reaction of the sample/probe (e.g., solution, liquid or reagent such as chemical or biological) with the target (e.g., solution, liquid or reagent such as chemical or biological), and (c) washing excess sample/probe from the substrate.

The reaction step or part typically requires good mixing, temperature and time. The wash step typically needs to completely remove substantially all excess unreacted probes. In conventional techniques, these process steps are typically done by flooding the entire array substrate, which can undesirably add to the cost and time.

Certain embodiments of the invention by employing drop on drop modes of operation, as described further herein, are advantageously able to execute these hybridization process steps by desirably using less probe and/or by achieving faster process times.

It should be noted that some types of arrays do not require blocking or washing, such as for intercalating reactions, where the probe only becomes active when the assay reaction takes place.

Some Arraying and Hybridization Embodiments

Certain embodiments of the invention provide novel and improved systems and methods for arraying. Some embodiments of the invention provide a web based arraying format. Some other embodiments of the invention provide a sheet based arraying format.

Certain embodiments of the invention provide novel and improved systems and methods for assaying and hybridization. Some embodiments use a drop on drop assaying or hybridization mode. In some embodiments, a substantially inert substrate is utilized. In some other embodiments, an interactive substrate is utilized.

Web Based Manufacturing Systems for Arraying

Figure 6:
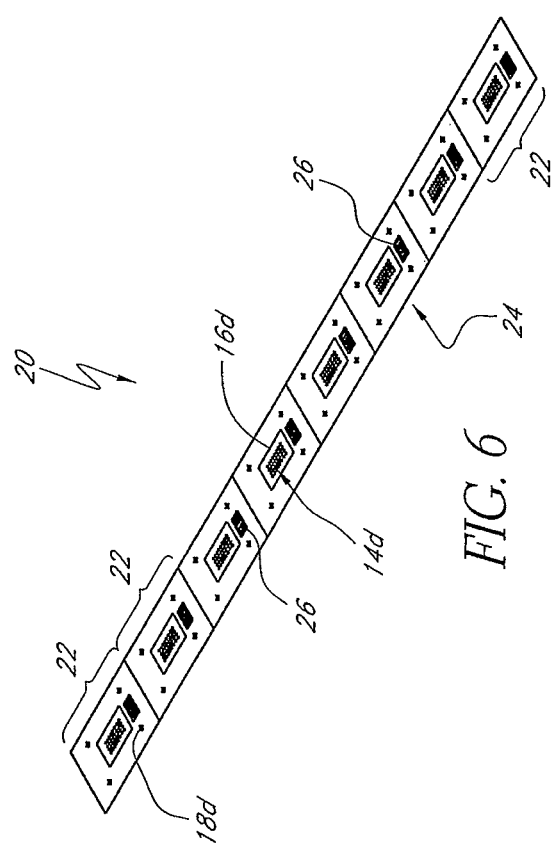
FIG. 6 is a simplified perspective view of an array or microarray based web design substrate or substrate assembly illustrating features and advantages in accordance with certain embodiments of the invention.
Figure 9:
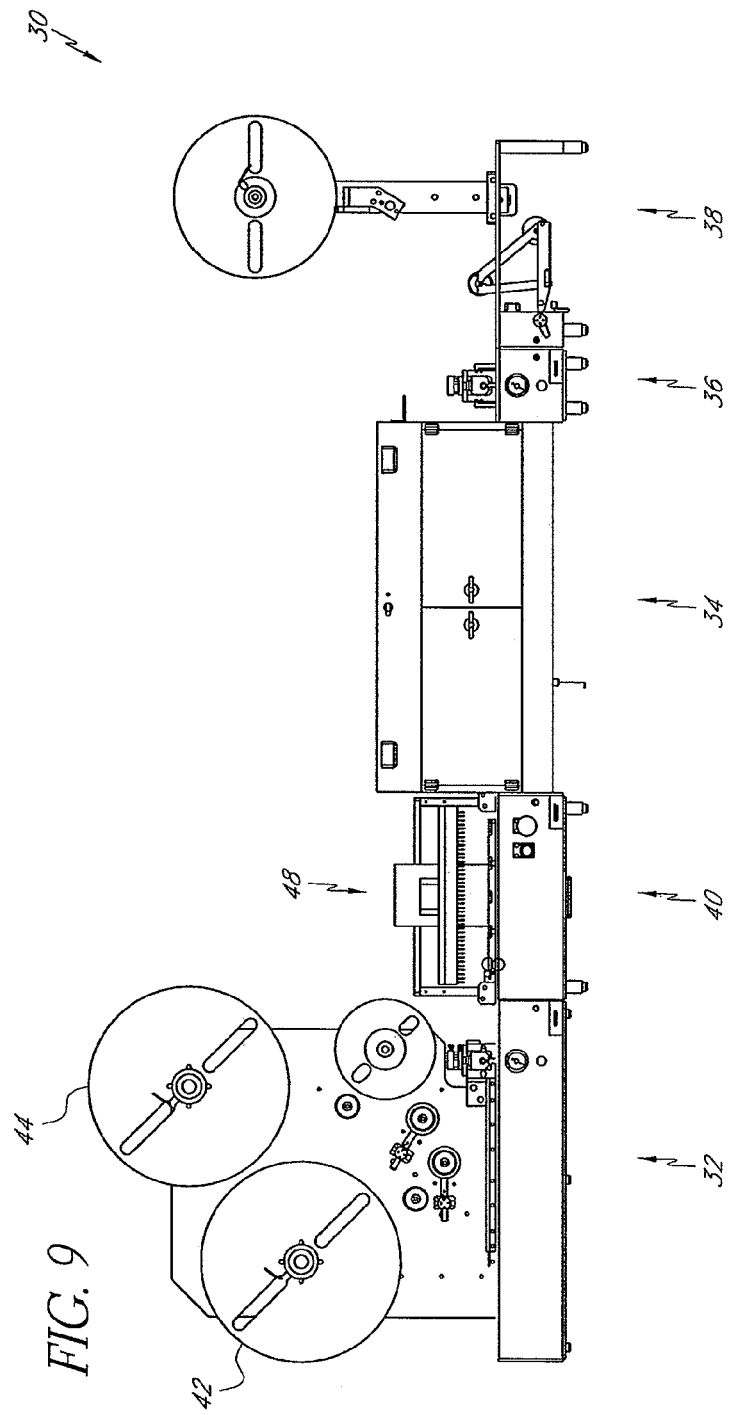
FIG. 9 is a simplified side view of a web based array assembly system illustrating features and advantages in accordance with certain embodiments of the invention.
Figure 10:
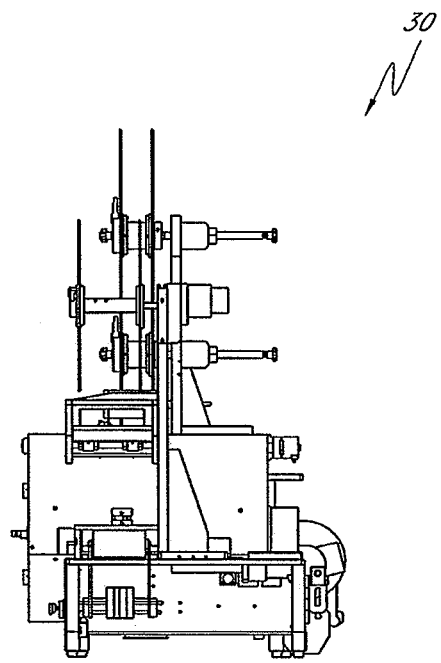
FIG. 10 is a simplified end view of the web based array assembly system of FIG. 9 illustrating features and advantages in accordance with certain embodiments of the invention.

Some embodiments of the invention provide web based systems and methods for arraying. FIGS. 6-8 show an assay web substrate concept, design, structure or assembly 20 in accordance with certain embodiments.

The web substrate format or assembly 20, in some embodiments, is generally created based on the array formats of FIGS. 3-5 and is desirably used for in line web based manufacturing. The web substrate 20 comprises a plurality of substrate units or elements 22 with each having an array or microarray 12d formed thereon. The arrays 12d each comprise a plurality of spots or dots 14d arranged in a predetermined manner, such as but not limited to, for example, a rectangular or square array format.

The web substrate 20, in some embodiments, comprises a substrate surface or medium 16d and a cover, carrier or shield 24 which are mechanically connected to or in mechanical communication with one another. The substrate surface or medium 16d has the spaced arrays 16d formed thereon.

In some embodiments, the substrate surface or medium 16d comprises a flexible film or the like and is fabricated from, for example, polyester. The cover or carrier 24 comprises, for example, a plastic material or the like, and desirably provides protection and/or at least some degree of controlled rigidity to the substrate surface or medium 16d to facilitate handling and processing of the web substrate structure 20.

Each substrate unit 22, in some embodiments, comprises one or more fiducial targets, indicia or marks 18d on the cover 24 to facilitate proper alignment and/or orientation, such as during processing, with efficacy, as needed or desired.

In certain embodiments, each substrate unit 22 comprises a bar code 26 or the like to facilitate in identification, classification and/or detection of the particular substrate unit and the array formed thereon.

Some exemplary dimensions are shown in millimeters (mm) in FIG. 8. The embodiment of this figure also shows a 32 (8×4) array 12d configured with spots or dots 14d located on (or spaced by) about 2 mm centers.

FIGS. 9-12 show different views of an array dispensing machine or a web based manufacturing system 30 to produce arrays or microarrays on a continuous basis to form one or more web substrate structures such as the web substrate 20 in accordance with certain embodiments of the invention.

The web substrate manufacturing system 30, in some embodiments, comprises a staggered array of dispensers or dispense channels as shown. The web substrate manufacturing machine 30 includes, in some embodiments, web feeds for a plastic backing and substrate materials which are laminated followed by dispensing, drying and re-reeling.

The web substrate manufacturing system, apparatus or machine 30 generally comprises a laminate module or section 32, a dispense module or section 40, a drying module or section 34, a capstan module or section 36, and a take-up module or section 38 arranged in a successive or consecutive manner with the laminate module 32 occupying the upstream most position and the take-up module 38 occupying the downstream most position.

The laminate module 32, in some embodiments, comprises a backing reel apparatus 42 and a membrane reel apparatus 44 and a lamination or laminating apparatus or system. The backing reel apparatus 42 provides a backing, cover or carrier (e.g., the plastic cover 24) and the membrane reel apparatus 44 provides a membrane, film or substrate surface or medium (e.g., the polyester film 16$d$) which are laminated by the lamination apparatus of the module 32 to create one or more web substrate devices onto which the appropriate reagent or liquid arrays are formed.

The dispense module 40 is used to dispense or deliver one or more reagents or liquids on to the web substrate device(s) to form arrays or microarrays thereon so as to form a web substrate structure (e.g., the web substrate 20). In some embodiments, the dispense module 40 generally comprises a dispense head 46 and an X-Y axis dispense head motion positioner 48 to provide movement to the dispense head 46 and hence relative motion with respect to the web substrate device(s) on which the arrays or microarrays are to be formed. The web substrate device(s) can also be movable with respect to the dispense head 46 in some embodiments.

The dispense head 46 can comprise one or more dispensers or dispense channels with efficacy, as needed or desired. In the illustrated embodiment, the dispense head 40 comprises a plurality of dispensers or dispense channels arranged in a generally staggered configuration.

The drying module 34 can comprise a suitable drying source such as an oven, fans or the like with efficacy, as needed or desired. The drying module 34 is used to dry the dispensed reagent or liquid array spots onto the web substrate (e.g., the substrate medium or surface 16$d$).

The capstan module 36, in some embodiments, can comprise a rotatable drum or shaft to move or drive a tape or the like, such as the prepared web substrate structure(s) 20, at a predetermined (generally constant, but can be variable) speed towards and into the take-up module 38. The manufactured web substrate structure(s) 20 are re-reeled into the take-up module 38 from which they can then be retrieved, as and when needed, for assaying processes such as hybridization.

The movement of the web substrate from upstream to downstream may be further facilitated in conjunction with various other devices, such as, but not limited to conveyor belts, pick-and-place robotic arms, and the like. Desirably, a controller or control system is used to monitor and control the operation of the web substrate manufacturing machine 30 with efficacy, as needed or desired.

Figure 12:
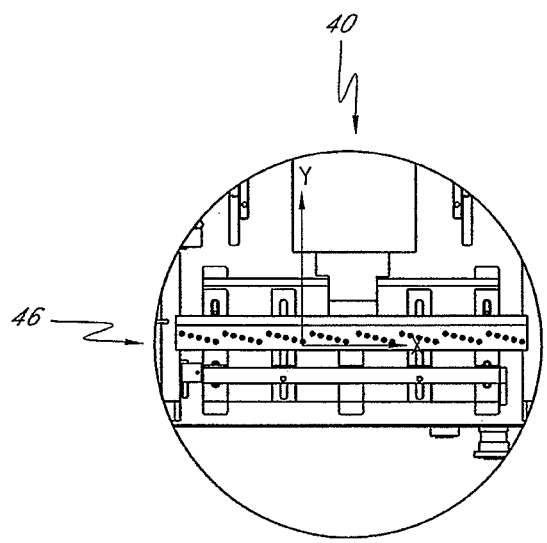
FIG. 12 is a simplified enlarged view along line 12-12 of FIG. 11 illustrating features and advantages in accordance with certain embodiments of the invention.
Figure 11:
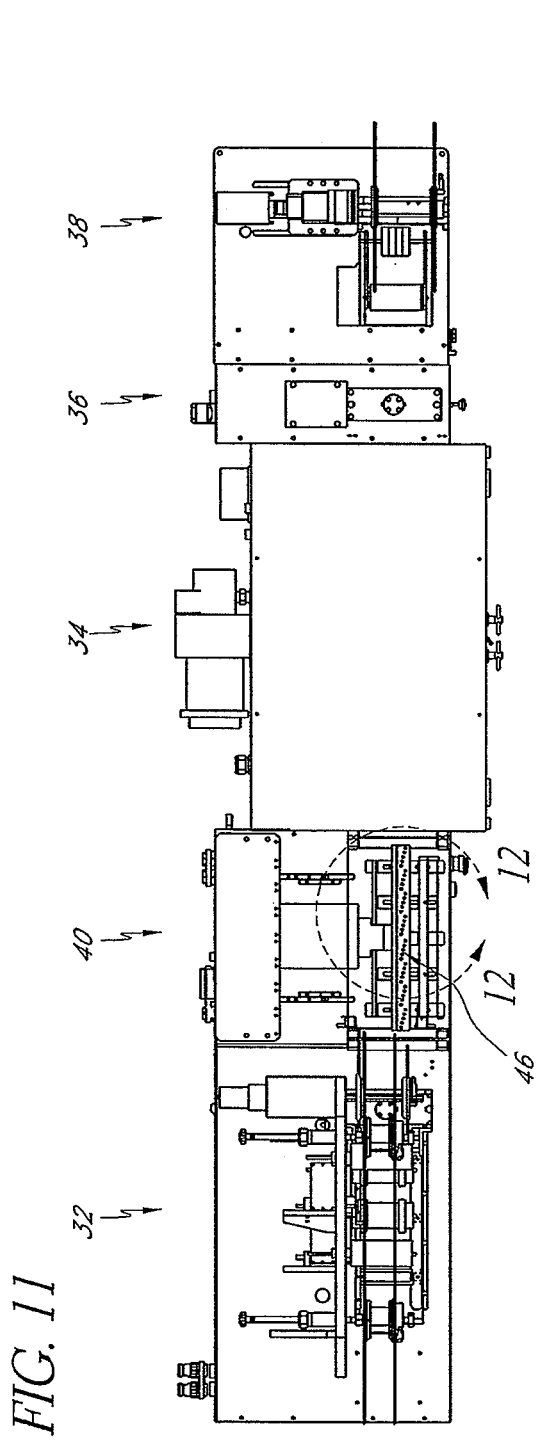
FIG. 11 is a simplified top view of the web based array assembly system of FIG. 9.

FIG. 12 shows a staggered dispense location pattern, in accordance with some embodiments, and an X-Y Cartesian axis or coordinate system. In one embodiment, the staggered dispense locations have an about 9 mm pitch in the X-direction and an about 2 mm pitch in the Y-direction. In modified embodiments, other dispense patterns, pitches and/or dimensional offsets may be efficaciously utilized, as needed or desired, depending at least partly on the particular application and/or process(es) involved.

In some embodiments, and as best seen in FIG. 12, the dispensing module or system 40 and/or the dispense head 46 comprises a plurality of bulk dispense channels or dispensers with the same number of channels as spots on the array. For a 5×8 array located on centers of 2 mm the dispense channels are grouped by sets of 5 with a 9 mm offset between channels along the web axis and 2 mm centers perpendicular to the web axis. There are 8 sets of the diagonal dispense array. Of course, as the skilled artisan will appreciate, the number, spacing and/or arrangement of the dispense channels can be efficaciously varied, as needed or desired, depending at least partly on the particular application and/or process(es) involved.

Still referring in particular to FIG. 12, by using time delays between the dispensers, each set of 5 channels can form, create or make a set of 5 spots generally perpendicular to the web axis. A second set of delays between the diagonal channel arrays places the sets of 5 spots at a spacing of 2 mm from the adjacent sets to finalize the creation of the 5×8 array.

In one example, each array substrate length is about 60 mm, and by utilizing web speeds of 60 mm per second, the throughput is 1 part (or array) per second which is equivalent to desirably about 6 million arrays per year on a single shift basis. Using three shifts per day can then advantageously achieve up to around 18 million arrays per year. Faster web speeds would yield even higher throughputs. This exemplified the high throughput capabilities of certain web based embodiments of the invention to achieve high speed array printing and manufacturing.

The reagent or liquid dispensing to form array(s) or microarray(s), such as in accordance with web based embodiments, can be performed by any of the dispensing (and/or aspirating) systems taught or suggested herein, for example, those of FIGS. 1A-1C and 2A-2F.

In certain embodiments, the non-contact dispensing technologies of U.S. Pat. Nos. RE38,281 E, 6,063,339, and US 2004/0219688 A1, the entirety of each one of which is hereby incorporated by reference herein and comprises a part of the present patent specification/application, are utilized for array printing, fabrication and/or manufacture. In one mode or embodiment of operation, continuous motion of the positive displacement syringe pump or device (or a direct current fluid source) with timing of valve opening, such as a solenoid dispenser or actuator valve, is employed for arraying. In another mode or embodiment of operation, controlled timing of valve, such as a solenoid dispenser or actuator valve, and syringe, such as a positive displacement syringe pump or device (or a direct current fluid source), operations are efficaciously employed for array creation.

Any of the dispensing and/or array technologies (e.g., FIGS. 1A-1C and FIGS. 2A-2F) taught or suggested can utilize tandem systems or configurations. Other examples include those of U.S. Pat. Nos. RE38,281 E, 6,063,339, 6,599,479 B1, and US 2004/0219688 A1, the entirety of each one of which is hereby incorporated by reference herein and comprises a part of the present patent specification/application. Dispense heads or channels can be efficaciously utilized to switch back and forth with respect to the dispensers. For example, switching between dispense heads and/or channels may be utilized to allow for to allow for syringe refill and tip washing while a secondary system is dispensing. Advantageously, this can provide substantially uninterrupted operation and/or high throughput processing.

In some embodiments, similar set ups can be used for high density array creation using the disposable/reusable piezo-electric pipette tip technology of Scienion, as taught or suggested herein. In certain embodiments, the Scienion sciFLEXARRAYER dispensers of FIGS. 1A and 1B are utilized. In some embodiments, the non-contact piezo dispensing technology of U.S. Pat. No. 6,599,479 B1, the entirety of which is hereby incorporated by reference herein, is employed.

In general, for the piezoelectric dispenser technologies taught or suggested herein the mode or embodiment of operation involves a controlled timing of the piezoelectric actuation for creating the array or microarray. In some embodiments, for example, the case of the 3,000 spot array (30×100) format shown in FIG. 5, the array configuration, in certain embodiments, can comprise 30 sets of 100 dispensers or dispense channels in a 4.5 mm by 3 mm offset arrangement.

As the skilled artisan will appreciate, numerous non-contact dispensing technologies can be efficaciously utilized to achieve high throughput array printing. In some modified embodiments, contact printing of arrays or microarrays can have efficacy in conjunction with other features and aspects of high speed array printing, hybridization, quantitative development and assaying, as taught or suggested herein.

In some embodiments, the liquid handling and dispensing technologies disclosed in U.S. Pat. Nos. 6,585,296 B1, 6,453,929 B1, 6,852,291 B1, 6,569,687 B2, 6,627,157 B1, and US 2003/0167822 A1, US 2003/0170903 A1 and US 2001/0053337 A1 are utilized, as applicable, in conjunction with, but not limited to non-contact dispensing and/or printing of arrays or microarrays. The entirety of each one of these U.S. patent documents is hereby incorporated by reference herein and comprises a part of the present patent specification/application.

FIGS. 13A and 13B show a dispensing instrument or system 210 as available from Innovadyne Technologies, Inc. which has some operations in California, U.S.A. The dispensing system 210 can be efficaciously employed in accordance with certain embodiments of the invention as disclosed herein, including, but not limited to non-contact dispensing and/or printing of arrays or microarrays.

The dispensing instrument 210 utilizes two separate flow paths—a "syringe path" and a "pressure path"—to aspirate and dispense reagent. FIG. 13A illustrates reagent aspiration using the "syringe path" and FIG. 13B illustrates reagent dispensing using the "pressure path."

Referring in particular to FIG. 13A, the syringe path is used to aspirate an air gap and reagent. The syringe path is the flow path between the syringes and the tips, as shown in FIG. 13A. To aspirate an air gap, the tips are exposed to the atmosphere (not descended into the reagent tray), allowing air to flow into the tips. The valves are switched into position, allowing flow from the tips to the syringes. The syringes are pulled down, creating a vacuum, and system fluid flows from above the reagent tray to the syringes. Air is aspirated through the tips and system fluid flows toward the syringes. Next, to aspirate reagent, the tips are descended into the reagent tray, then the syringes are pulled down further. Reagent flows from the reagent tray to the syringes, separated from system fluid by the air gap.

Referring in particular to FIG. 13B, the pressure path, using a pressure reservoir filled with de-ionized system liquid held at system pressure, is used to dispense reagent. The pressure path is the flow path from the pressure reservoir, via the microsolenoid valves, to the tips, as shown in FIG. 13B. The pressure reservoir contains system liquid, maintained by a digital pressure regulator (DPR) at a specified system pressure. To dispense reagent, the hybrid valve switches the flow from the syringe path to the pressure path, and then the microsolenoid valves are opened and closed the requisite number of times to permit the desired volume of system liquid to flow from the pressure reservoir toward the tips. Note that the reagent does not itself flow through the microsolenoid valves; system liquid does. The motion of the system liquid towards the tips displaces the desired volume of reagent out through the tip, and reagent is dispensed into the plate.

In some embodiments, the liquid handling and dispensing technologies disclosed in U.S. Pat. Nos. 6,669,909 B2 and 6,713,021 B1, European Patent No. EP 1379332 B1, and PCT Patent Application Publication No. WO 02/076615 A2 are utilized, as applicable, in conjunction with, but not limited to non-contact dispensing and/or printing of arrays or microarrays. The entirety of each one of these patent documents is hereby incorporated by reference herein and comprises a part of the present patent specification/application.

Figure 14:
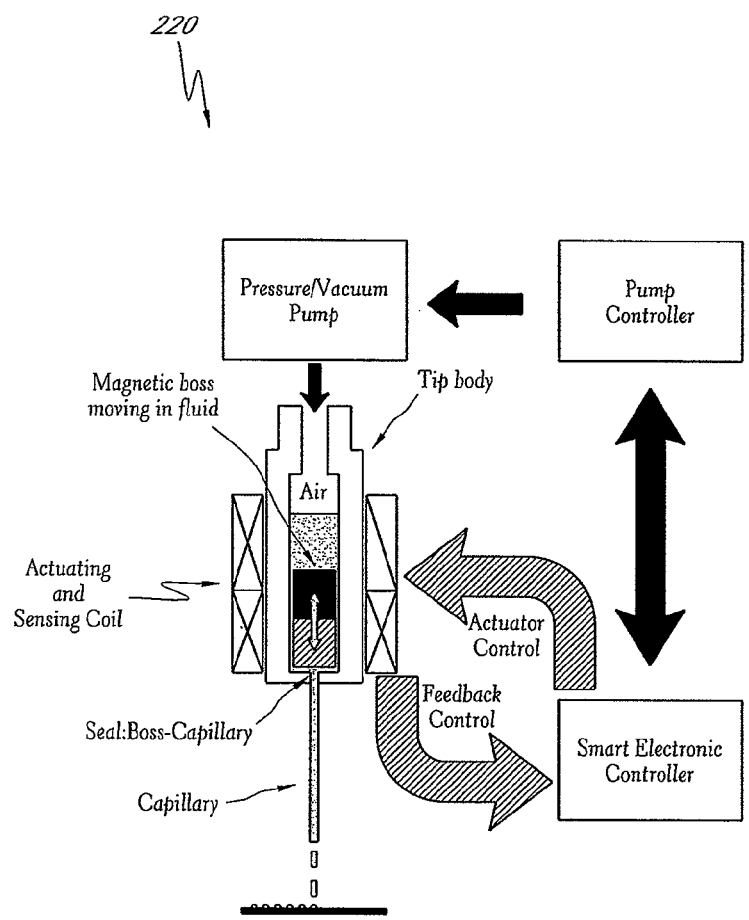
FIG. 14 is a simplified view of an aspirating and dispensing system illustrating features and advantages in accordance with certain embodiments of the invention.

FIG. 14 shows a dispensing system or apparatus 220 as available from Deerac Fluidics which has some operations in Ireland and Massachusetts, U.S.A. The dispensing system 220 can be efficaciously employed in accordance with certain embodiments of the invention disclosed herein, including, but not limited to non-contact dispensing and/or printing of arrays or microarrays.

Referring in particular to FIG. 14, the system 220 utilizes a Spot-On™ technology to aspirate and dispense liquids or reagents. In some embodiments, the core of the Spot-On™ technology is a pipetting tip which acts as a fast-actuating valve and which is connected to a pressure or vacuum source. There is no system liquid within the pipettor—only air, and the sample liquid which is aspirated and dispensed through the tip. The tip preferably comprises a PEEK body which contains a "boss" made of a magnet coated with a chemically inert material. The boss when resting against the capillary creates a seal and can be used as a valve. This valve is opened by raising the boss, which creates an opening to the capillary for the flow of the fluid. The boss is raised by the passage of a current through an electronic coil which surrounds the lower section of the tip body (as shown in FIG. 14). The opening time for each aspirate and dispense is determined by the Spot-On™ electronic controller from the supplied liquid properties, the required or desired volume and other system parameters. Precise control of the dispensation volume is further enabled by sensing the level of magnet actuation, using a sensing coil, and processing this information into a real time feedback. This feedback allows for the prospect of measuring the viscosity and flow of the liquid to be dispensed, adding a significant advantage to the Spot-On™ technology.

Some unique and/or novel features, aspects and advantages in accordance with certain embodiments of web based manufacturing systems for arraying include, but are not limited to the following:

(1) Some embodiments advantageously provide continuous motion generation of arrays at high production speeds using non contact dispensing. These would comprise continuous web or a web carrier with individual sheets that is indexed.

(2) Some embodiments desirably provide the ability to change array patterns using timing control and layout of the dispense channels with efficacy, as needed or desired.

(3) In certain embodiments, array patterns do not necessarily have to be mirrored in the dispenser configuration. One specific embodiment of the invention is, that out of 3,000 dispensers, arrays manufactured from a subset of 384 dispensers might be the final product. Due to the versatile design of certain system embodiments, in principle every array manufactured can show a different composition of bioanalytes by addressing a subset of dispensers to create subsets of arrays from the complete set of bioanalytes. This can desirably happen without decreasing the speed of the conveyor belt. As a result, in some embodiments, and advantageously, identical and non identical array replicates can be produced with an identical speed.

(4) Some embodiments desirably provide the ability to perform in line inspection of array quality using wet/dry or other contrast methods with efficacy, as needed or desired.

(5) Some embodiments advantageously provide the ability to add other reagent processes such as blocking and washing using emersion, spray coating or drop on drop approaches with efficacy, as needed or desired.

(6) Some embodiments desirably provide the ability to combine other value added processing in line such as, but not limited to, lamination, drying, incubation, cutting, and punching, among others, with efficacy, as needed or desired.

Sheet Based Manufacturing Systems for Arraying

Figure 15:
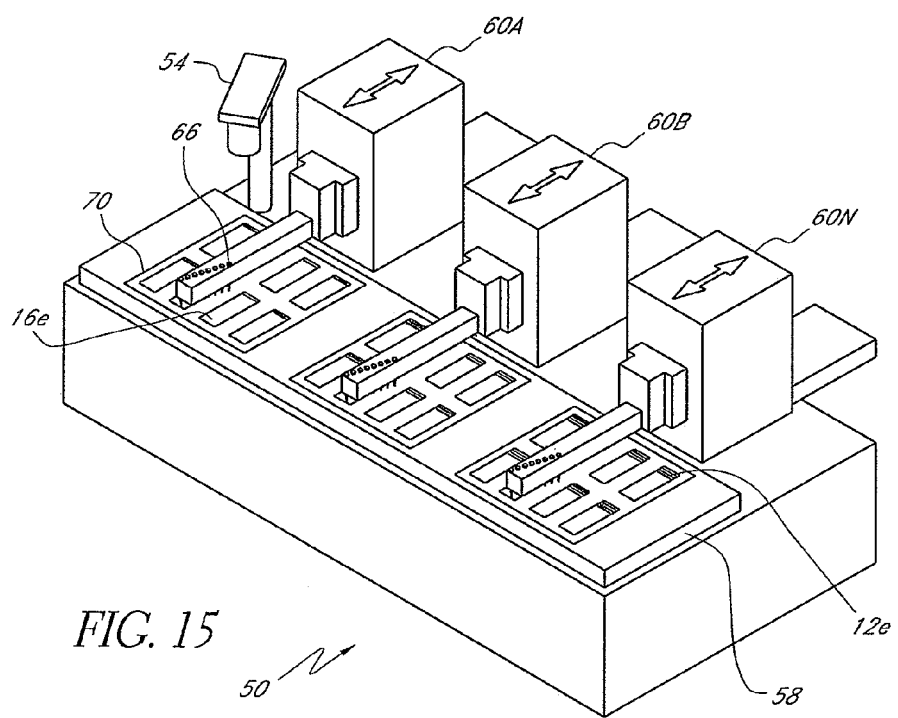
FIG. 15 is a simplified perspective view of a sheet based array assembly module or system illustrating features and advantages in accordance with certain embodiments of the invention.

FIG. 15 shows an array dispensing machine or sheet based dispense array module, apparatus or manufacturing system 50 in accordance with certain embodiments of the invention. In certain sheet based dispensing embodiments, such as that of FIG. 15, the dispensing is distributed over a number of dispense work stations 60 (60A, 60B, . . . , 60N) as compared to embodiments of the continuous in line approach, such as those of FIG. 9-12.

It is contemplated that the sheet based approach can be considered, at least in some aspects, as a compromise manufacturing strategy relative to the continuous web format. For example, the sheet based approach can be suitable in applications where the substrate material may not lend itself to a web format due to thickness or mechanical rigidity or other considerations.

The sheet based dispensing module 50, in some embodiments, generally comprises a plurality of dispense work stations 60, one or more positioning cameras 54 or the like, and a conveyor mechanism, system or apparatus 58. Each dispense work stations 60 comprises a dispense head 66 with one or more dispense channels or dispensers.

Substrate assemblies or structures 70, in some embodiments, each comprise one or more dispense regions 16e (or substrate units) on which dispense patterns, arrays or microarrays 12e are formed as the substrates 70 are transported via or on the conveyor mechanism 58. In these embodiments, the format of the arrays is in a sheet format or a X-Y carrier format which provides an X-Y presentation of arrays to the dispensing process.

In certain embodiments, an indexing in-line process can be established where the sheets or carriers can be moved through process steps such as dispensing, and drying, among others, similar to the continuous in-line approach embodiments. In some embodiments, the dispensing is done or performed with the web or carrier in a stopped position and the motion is supplied by an overhead gantry motion system. In this case, the dispensing can be normal or parallel to the web/conveyor motion with efficacy, as needed or desired.

The reagent or liquid dispensing to form array(s) or microarray(s), such as in accordance with sheet based embodiments, can be performed by any of the dispensing (and/or aspirating) systems taught or suggested herein. These include those described above in connection with web based manufacturing embodiments.

Some unique and/or novel features, aspects and advantages in accordance with certain embodiments of sheet based manufacturing systems for arraying include, but are not limited to, those described above in connection with web based manufacturing embodiments.

Some further unique and/or novel features, aspects and advantages in accordance with certain embodiments sheet based manufacturing systems for arraying include, but are not limited to the following:

(1) Some embodiments efficaciously and desirably provide high throughput manufacturing methods for substrate formats that do not lend themselves to a continuous web format, as needed or desired.

(2) Certain embodiments advantageously provide the ability to do in-line processes to maintain dispensing quality such as, but not limited to, periodic cleaning of dispense tips to ensure good quality dispensing without perturbing the quality and speed of the overall process. For example, the index time can be defined to allow ample time for tip cleaning.

Exemplary Formats for Continuous and Indexed Web Manufacturing Methods

The arraying systems and methods in accordance with certain embodiments of the invention can efficaciously utilized to create, manufacture or produce a wide variety of array or microarray substrate structures or assemblies, as needed or desired.

Figure 16:
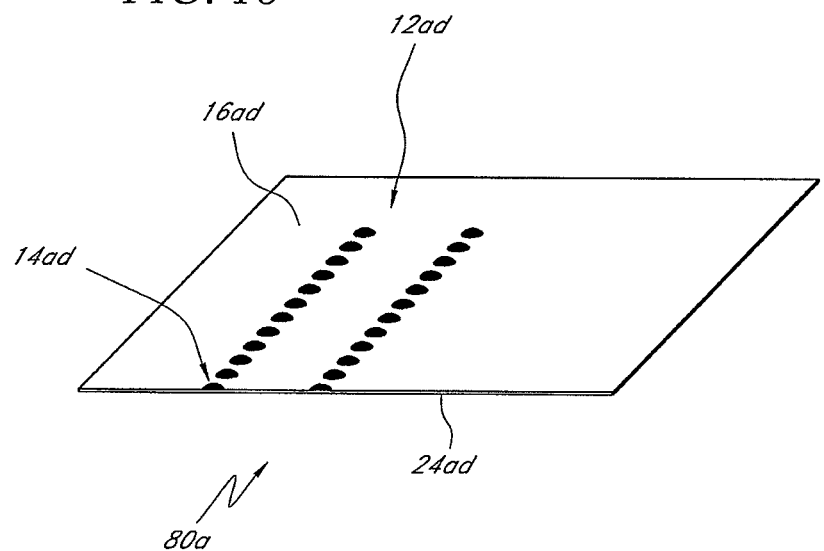
FIG. 16 is a simplified perspective view of an inert substrate assembly or structure illustrating features and advantages in accordance with certain embodiments of the invention.

FIG. 16 shows a substantially passive or inert substrate structure 80a fabricated in accordance with certain arraying embodiments. An array 12ad comprising a predetermined or selected arrangement or configuration of dispensed liquid or reagent spots, dots or drops 14ad is formed on a membrane, substrate surface or medium 16ad. The substrate surface or medium 16ad can serve as a carrier or an independent carrier 24ad may be employed with efficacy, as needed or desired.

Figure 17:
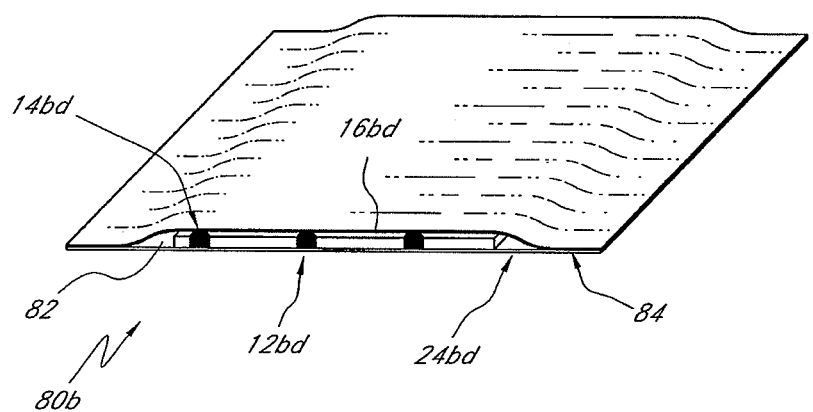
FIG. 17 is a simplified perspective view of an interactive substrate assembly or structure illustrating features and advantages in accordance with certain embodiments of the invention.

FIG. 17 shows a substantially active or interactive substrate structure 80b fabricated in accordance with certain arraying embodiments. An array 12bd comprising a predetermined or selected arrangement or configuration of dispensed liquid or reagent spots, dots or drops 14bd is formed intermediate a membrane, substrate surface or medium 16bd and a carrier 24bd. An absorbent material 82 is generally provided between the membrane, substrate surface or medium 16bd and the carrier 24bd and adhesive junctions 84 or the like are utilized to laminate, attach or connect the membrane and carrier.

Referring in particular to the inert substrate embodiment of FIG. 16, test reagents or liquids (e.g., in the form of droplets 14ad) are put down or dispensed onto the substrate surface or membrane 16ad which does not chemically interact with the reagent or liquid and hence the drops 14ad hydrodynamically sit or reside on the substrate surface or medium 16ad. In this case the type of assay that can be used here may be limited since under hybridization conditions the substrate cannot be washed as the material will be removed. However, advantageously, in certain embodiments, by using an intercalating dye type based method for detection of DNA binding events where only positive probe and target reactions turn on the probe, the wash step is not needed. Also, again advantageously, blocking steps are not required since the substrate is inert. One example of such an assay would be a Single-Nucleotide Polymorphism (SNP) assay on a polyester film in either a web or sheet format.

Referring in particular to the interactive substrate embodiment of FIG. 17, the targets or drops 14bd actually bind to the substrate. In this case, both blocking and washing steps are typically performed to complete the assay for reading. The active substrate 80b represents one example of such an assay format suitable for the proposed in line for indexing approach described above which is an adaptation of a flow through commonly used for protein assays. In one embodiment, the substrate device 80b generally comprises a plastic backing 24bd, a nitrocellulose membrane 16bd and an absorbent spacer 82 that is laminated between the membrane substrate 16bd and the plastic carrier 24bd. In this case, the membrane 16bd comprises the active substrate surface.

Figure 18:
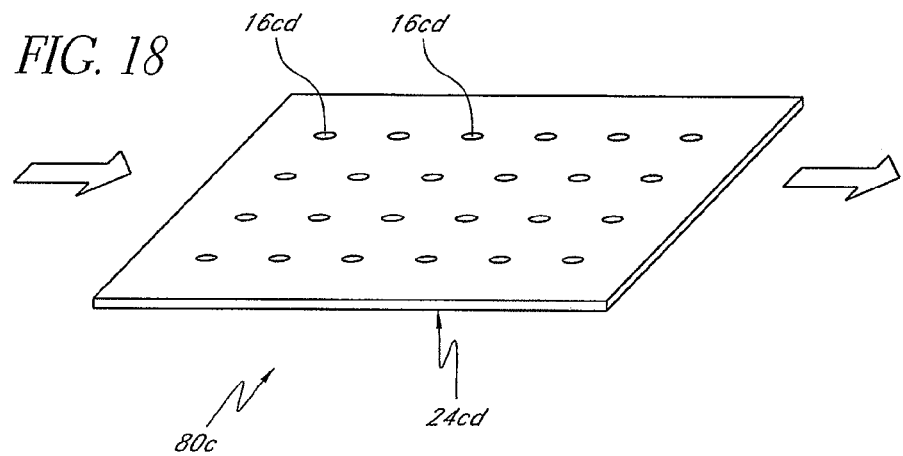
FIG. 18 is a simplified perspective view of a PCR conducive substrate assembly or structure illustrating features and advantages in accordance with certain embodiments of the invention.

FIG. 18 shows a Polymerase Chain Reaction (PCR) adaptable substrate structure or assembly 80c in accordance with certain embodiments. The substrate device 80c employs an array or microarray configuration such as a sheet with welds 16cd or a microtiter format. The substrate device 80c can utilize a carrier or backing 24cd with efficacy, as needed or desired. A plurality of such devices 80c may be conveyed on a suitable transportation device. The PCR assay employs amplification and has certain special processing steps in accordance with embodiments of the invention. The substrate device 80c can be customized, for example, based on the number, spacing and/or arrangement of array sites, dots or drops with efficacy, as needed or desired.

In certain embodiments, and as discussed further below, assaying based on a PCR format such as a TaqMan® assay is performed. An array is dispensed into a PCR plate such as the substrate plate 80c of FIG. 18. In this case, the array comprises a set of oligonuclides including a TaqMan® probe. For certain embodiments of this PCR assay, the reaction is performed under an oil layer and a master mix (TaqMan® master mix) and sample are dispensed through the oil. As discussed below, a thermal cycler is utilized followed by reading.

Drop on Drop Methods and Hybridization Equipment Systems

Figure 19:
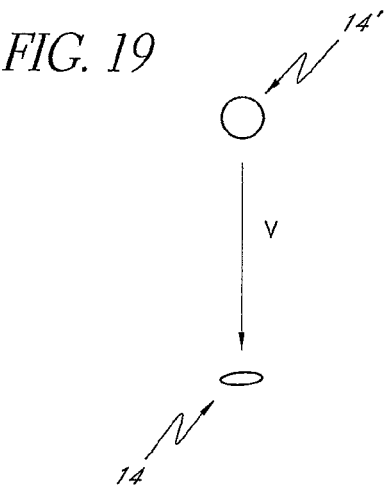
FIG. 19 is a simplified schematic view of precision drop on drop (or spot) dispensing for assaying purposes illustrating features and advantages in accordance with certain embodiments of the invention.
Figure 20:
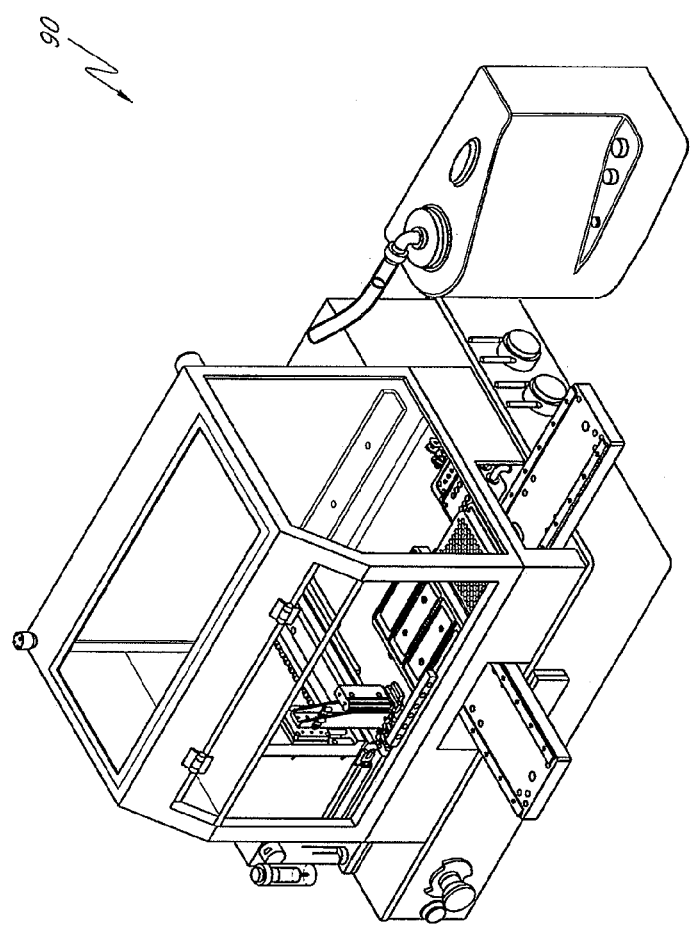
FIGS. 20-23 are various simplified views of a bench top hybridization (and/or assaying) system illustrating features and advantages in accordance with certain embodiments of the invention.
Figure 21:
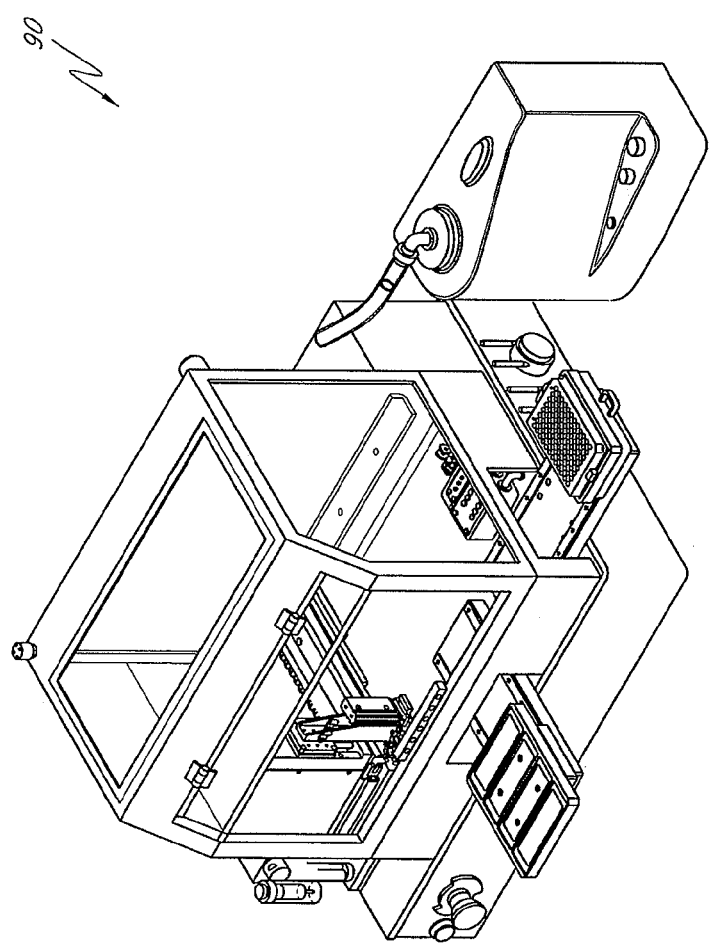

FIG. 19 shows embodiments in accordance with precision drop on drop (or spot) dispensing for hybridization and/or assaying processes which advantageously provide for, among other desirable features, high throughput and judicious utilization of valuable liquids or reagents. In particular, the figure schematically illustrates the dispensing of a liquid or reagent drop or droplet 14' onto a liquid or reagent drop, spot or dot 14 such as one formed as part of an array on a substrate. In some embodiments, the drop 14' is dispensed at a certain predetermined or selected velocity (V) or momentum to advantageously facilitate desirable kinetic mixing and/or reaction between the drop 14' and the arrayed spot 14.

Inert Substrate Related Embodiments:

FIGS. 20-23 show various views of some embodiments of a bench top hybridization (and/or assaying) system 90 particularly suited to the hybridization of a single array. In this case, only the probe or sample (e.g., reagent(s)) typically needs to be added to the substrate coupled with heating for the hybridization process. After this the array is ready for reading.

The hybridization machine 90 can utilize any of the dispensing (and/or aspirating) technologies (e.g. those of FIGS. 2A-2F) as taught or suggested herein with efficacy, as needed or desired. Certain embodiments of the machine 90 are configured with any of the solenoid actuated or piezoelectric dispensing technologies of U.S. Pat. Nos. RE38,281 E, 6,063,339, 6,599,479 B1, and US 2004/0219688 A1 the entirety of each one of which is hereby incorporated by reference herein and comprises a part of the present patent specification/application.

In some embodiments of these cases, the input to the machine 90 would be the sample (e.g., liquid reagent(s)) in the format of a microtiter plate and a master mix as a bulk reagent that is mixed with the sample. The work station comprises two dispense channels: a) one is to add the master mix to the sample with mixing and b) one is to aspirate the mixture followed by dispensing onto each individual spot in the arrays. After drying the arrays are ready for reader analysis. Typically, this system would be targeted at low volume use for point of testing type of applications. The hybridized array would then go to a read station.

Figure 22:
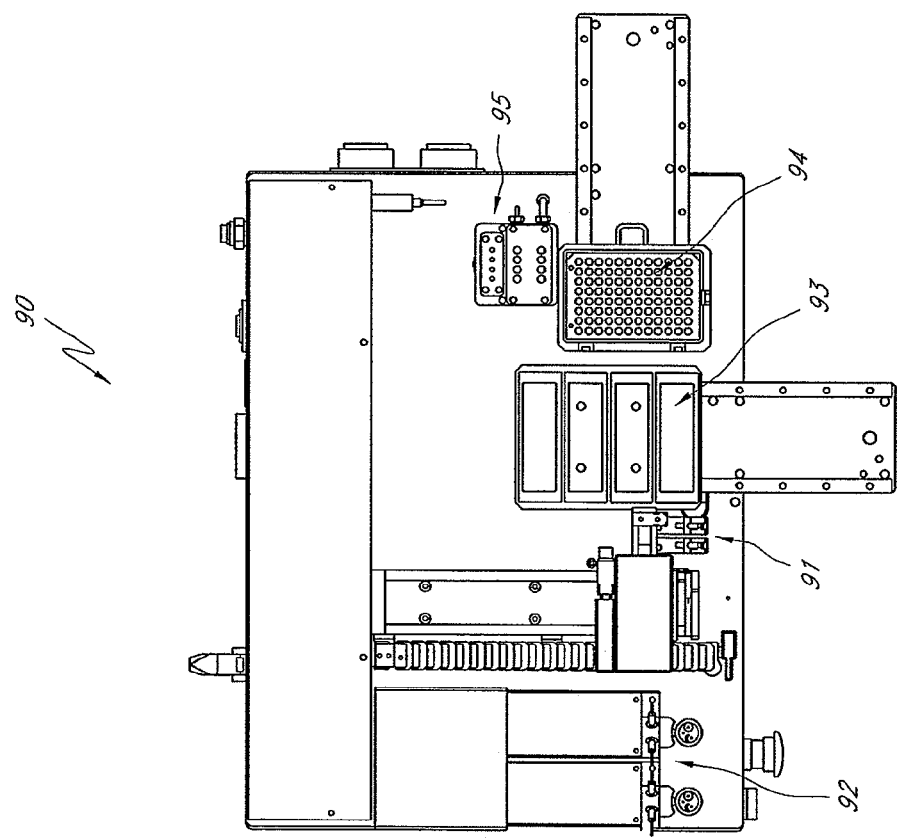

Referring in particular to FIG. 22, in certain embodiments, the system or machine 90 generally comprises, among other things, a dispense head 91, one or more syringe pumps 92, an array nest 93, a source plate nest 94, and a wash station 95.

Figure 23:
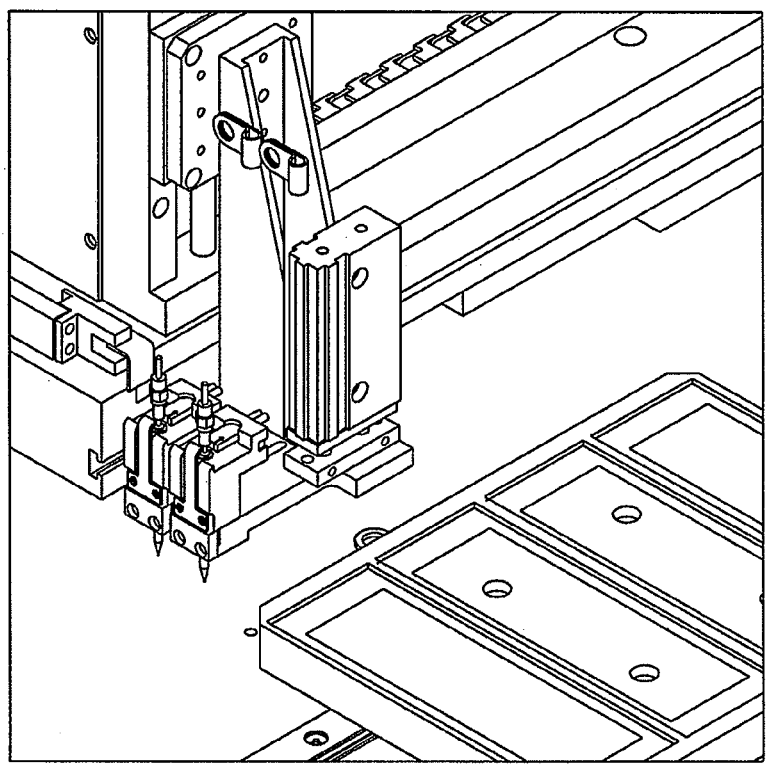

Referring in particular to FIG. 23, an enlarged view of the dispense head 91 shown along with, among other things, an array nest (40×120 shown) 93' and a differential Z-axis actuator 96. The dispense head 91, in certain embodiments, comprises one or more bulk dispense channels 97 and one or more aspirate and dispense channels 98.

FIGS. 20-23 generally show an AD1500 Research System as available from BioDot, Inc. of Irvine, Calif., U.S.A. Any of the liquid handling, dispensing, aspirating, arraying, hybridization embodiments, among others, disclosed herein can efficaciously utilize BioDot's AD3050 Research System, AD3200 Development System, AD3400 Development System, and AD6000 Production System. For example, in some arrangements, the AD6000 machine can comprise up to 96 dispense channels. In some arrangements, the AD6000 machine can fill 1536 well plate with 500 nL/well in about 20 seconds.

Figure 24:
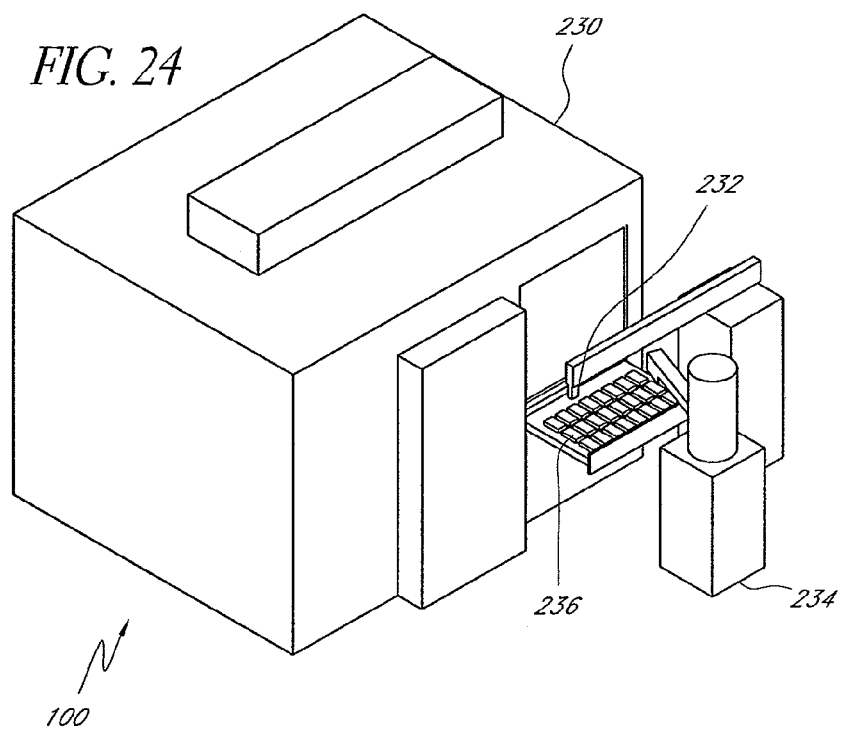
FIG. 24 is a simplified perspective view of a sample storage, dispense master mix and magazine loader system illustrating features and advantages in accordance with certain embodiments of the invention.
Figure 26:
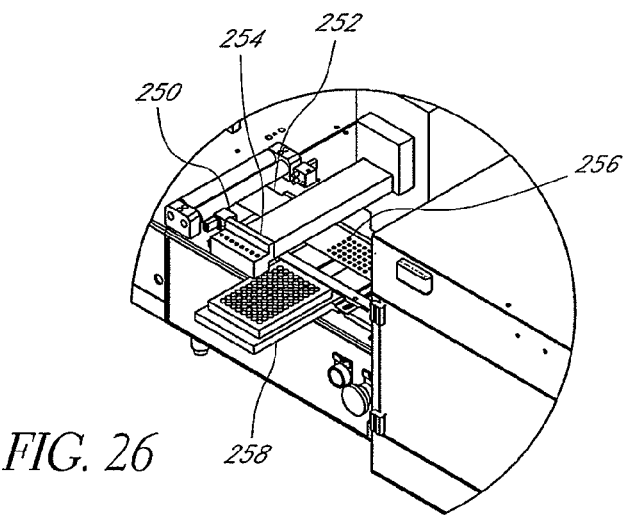
FIG. 26 is a simplified enlarged view along line 26-26 of FIG. 25 illustrating features and advantages in accordance with certain embodiments of the invention.
Figure 25:
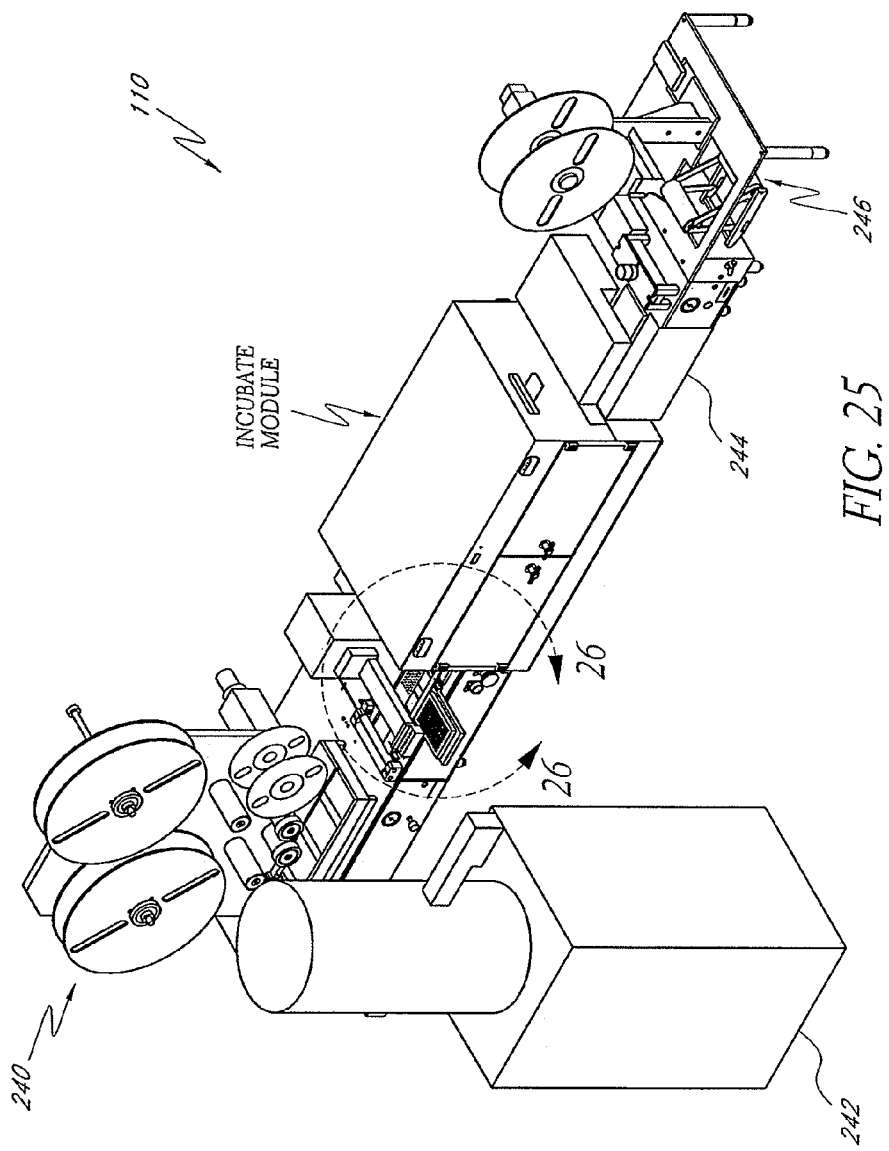
FIG. 25 is a simplified perspective view of a hybridization and reading system illustrating features and advantages in accordance with certain embodiments of the invention.

FIGS. 24-26 show various views of some embodiments of a sample storage, dispense master mix and magazine loader system 100 and a hybridization and reading system 110 particularly suited for high volume assay array applications. FIGS. 27-31 show various views of certain other embodiments of a high volume array printing, hybridization and reading system or assay array machine 120.

Referring in particular to FIG. 24, the system 100 in certain embodiments generally comprises, among other things, a sample plate storage system 230, a master mix dispense head 232, a magazine loader 234, and sample micro-plates 236.

Referring in particular to FIG. 25, the system 110 in certain embodiments generally comprises, among other things, a supply module 240, a magazine storage module or device 242, a reader module 244, and a take-up module 246.

Referring in particular to FIG. 26, this drawing in certain embodiments generally shows, among other things, a camera positioner 250, conveyed material 252, a 8-channel dispense head 254, an arrayed pattern 256, and a micro-well plate 258.

Figure 27:
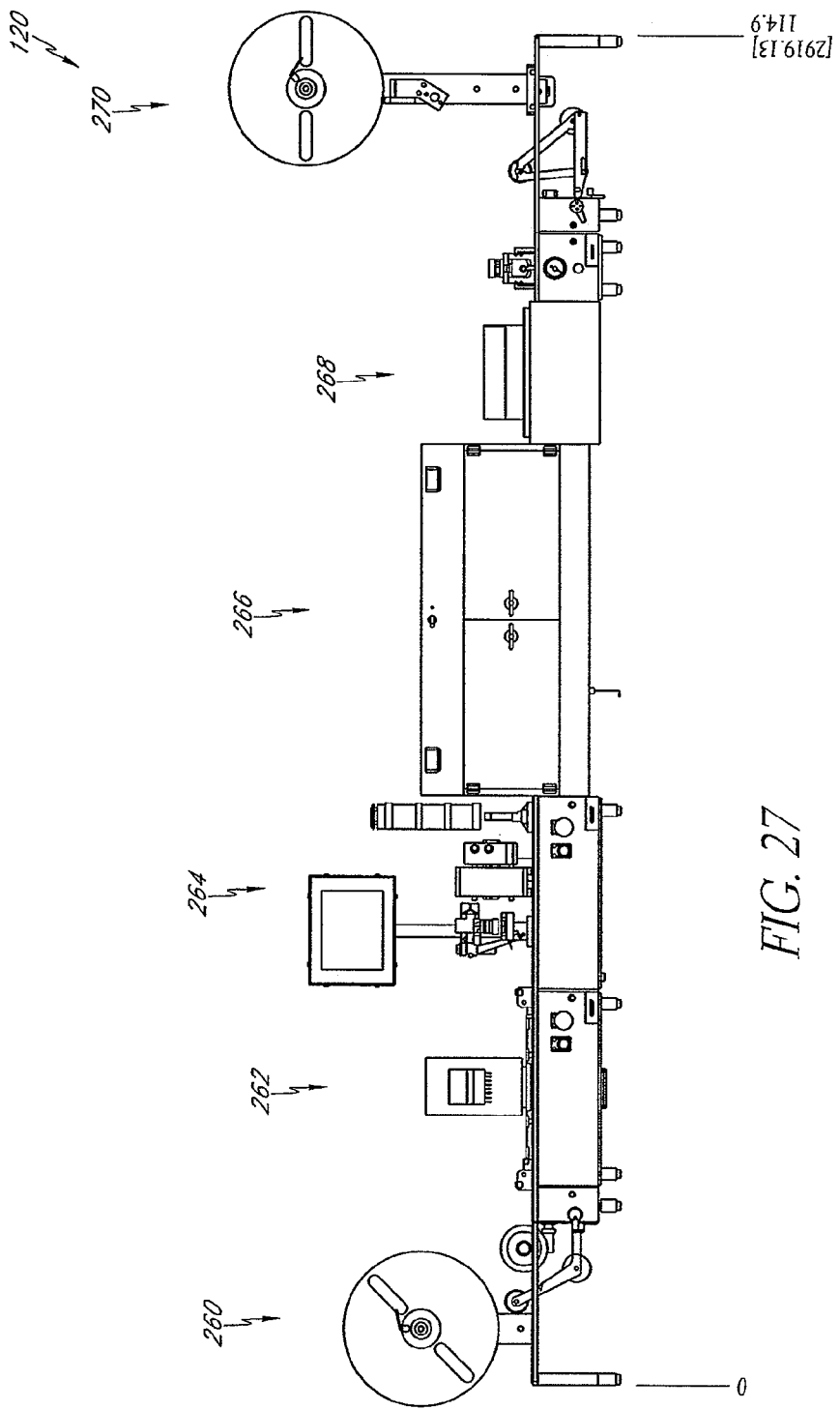
FIG. 27 is a simplified side view of an arraying, hybridization and reading system illustrating features and advantages in accordance with certain embodiments of the invention.
Figure 28:
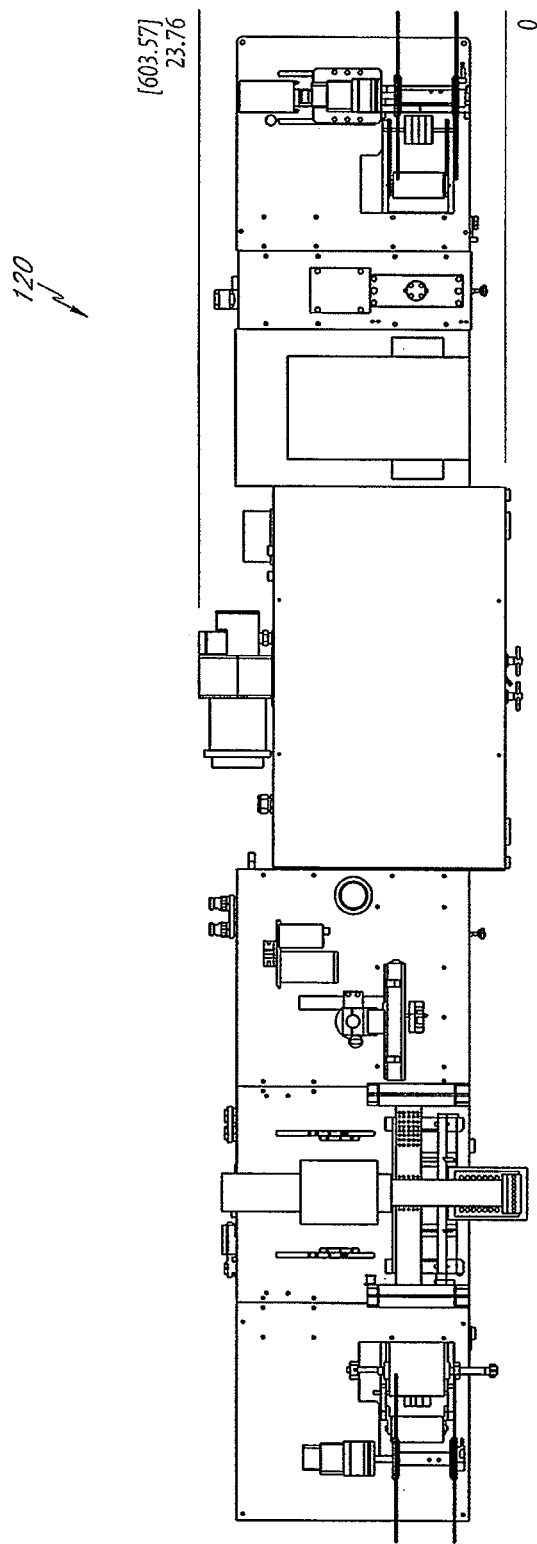
FIG. 28 is a simplified top view of the arraying, hybridization and reading system of FIG. 27 system illustrating features and advantages in accordance with certain embodiments of the invention.
Figure 29:
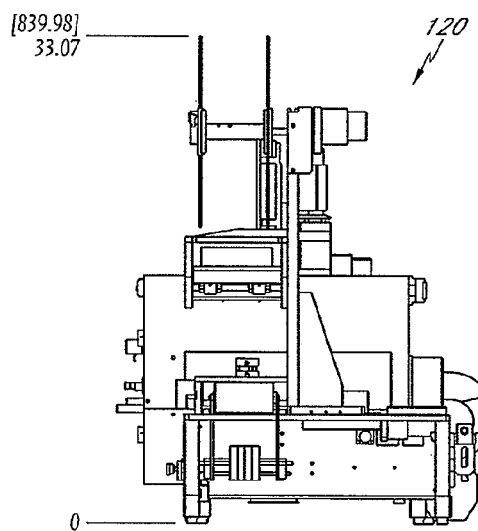
FIG. 29 is a simplified end view of the arraying, hybridization and reading system of FIG. 27 system illustrating features and advantages in accordance with certain embodiments of the invention.

Referring in particular to FIG. 27, the machine 120 in certain embodiments generally comprises, among other things, a payout module 260, a dispense module 262, a vision module 264, an incubation module 266, a reader module 268, and a take-up module 270.

Figure 31:
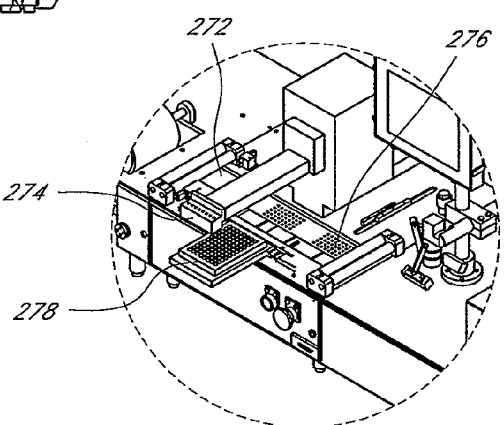
FIG. 31 is a simplified enlarged view along line 30-30 of FIG. 30 illustrating features and advantages in accordance with certain embodiments of the invention.

Referring in particular to FIG. 31, this drawing in certain embodiments generally shows, among other things, conveyed material 272, a 8-channel dispense head 274, an arrayed pattern 276, and a MTP source 278.

The embodiments of FIGS. 24-31 are particularly suited wherein hybridization and reading is done in a central laboratory and the testing is at a much higher volume (compared to the embodiments of FIGS. 20-23), for example, into the tens of millions or more annually. Certain embodiments of FIGS. 24-31 advantageously integrate both the hybridization and reading process together using a web based system for handling the arrays. In addition to the web handling module with dispensing, heating and reading the system comprise a sample store where the samples that come into the testing laboratory are stored. The samples could represent patient samples for medical tests, plant samples for agriculture crop or animal testing, or a wide range of other types of testing applications that are tested in a central laboratory environment.

Embodiments of the example machines 100, 110, 120 comprise one or more work stations or modules which are described further below. For this example, it is assumed that the test volume is about 10-100 microliters (μL) per sample using 96 well sample formats working 3 shifts per day to test 1.4 million samples per year or 8,000 samples per day or about 80-96 plates per day. These numbers are based on 4000 hours per year of available analysis time. The storage capacity of plates is assumed to be in the range of 5-10,000 plates. The store system can supply plates to a number of Hybridization Systems.

Some features of embodiments of the sample store and hybridization systems are described below with particular reference to the embodiments of FIGS. 24-31 and machines 100, 110, 120:

SAMPLE STORE MODULE: This system stores the sample plates before and after testing and has a capacity for storing up to 20,000 plates. Other operations within this module will be to thaw the plates, fill with master mix and then place the plates into transfer magazines.

Plate Handling Station: This station includes a barcode reading system and pick and place devices, such as robotic arms or the like, which can place or retrieve plates from the store racks.

Plate Storage Station: This station is a temperature controlled storage system with storage racks and a rack handling system. Each rack has a unique position within the storage system and each plate had a unique position on a given rack.

Dispense Master Mix Station: At this station the plate is thawed and then master mix is dispensed into the plates.

Magazine Load/Unload Station: This station loads the plates into a transfer magazine which then are located on the dispenser station on a Hybridization/Reader Module.

HYBRIDIZATION/READER MODULE: This module dispenses the sample to the test array followed by incubation and reading.

Web Feed Station: This station comprises a web feed module for the array web that has been printed on the master manufacturing machine. In this case the web is fed using an index mode to position a set of arrays in the Dispense Station. In this example we assume the positioning of 8 of the low density or 4 of the high density arrays per index.

Dispense Sample/Master Mix Station: This station comprises an overhead gantry module with a vision camera; two 8 channel dispenser and tip wash stations working in tandem to provide continuous indexing of the web. Each dispense head alternately aspirates 8 reagents and dispenses either 4 high density or 8 low density samples on arrays. After dispensing the dispense channels are cleaned for the next index cycle. Each sample is assigned the bar code of the individual arrays where the dispensing occurs.

Incubation Station: This station comprises an incubation tunnel where the arrays are heated to a determined temperature with a controlled level of humidity.

Read Station: This station comprises a reader head mounted on an overhead gantry. At each index step either 4 or 8 arrays are read by the camera and the data transferred to the system data base.

Web Take-up Station: This station comprises a take-up real for collection of the web.

Some unique and/or novel features, aspects and advantages in accordance with certain embodiments of sample storing, arraying, hybridization and reading systems include, but are not limited to the following:

(1) Some embodiments provide an array format on a web with unique bar codes for each test position.

(2) In some embodiments, alignment features are provided on each array for positioning using vision or other methods for application of reagents and reading.

(3) Certain embodiments provide Barcode, punch card, and/or Radio Frequency Identification Device (RFID) identifiers on samples plates with a data base that identifies individual well samples.

(4) Some embodiments comprise a sample storage system that can input new samples sent to the laboratory into the data base and can output these samples to the web hybridization/reader system. This would include the manual or automatic transfer to microtiter plate or other sample containers between the store and hybridization/reader system.

(5) In some embodiments, a data base tracking system is utilized that provides for collection, reading and sending of data for each sample that includes the analysis data and interpretation.

(6) Some embodiments provide a dispensing system that includes the ability to process multiple tests to provide for the ability to achieve high throughput processing.

(7) In some embodiments, an incubation system provides for the hybridization process to take place after application of the sample with master mix.

Interactive Substrate Related Embodiments:

An example of this type of array format is shown as the interactive substrate 80d in FIG. 17 for a flow through type of substrate. Other examples can include a membrane attached directly to the substrate or other surfaces that have been directly functionalized to bind with the target species. For these types of devices certain changes and/or additions are needed or desired in conjunction with the embodiments of the Manufacturing and the Hybridization/Reader machines described above.

Figure 34:
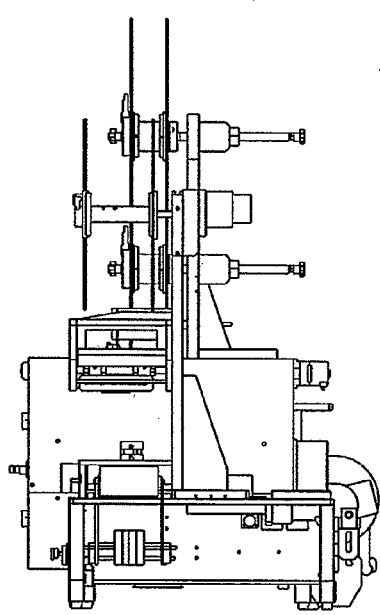
FIG. 34 is a simplified end view of the web based interactive array assembly system of FIG. 32 illustrating features and advantages in accordance with certain embodiments of the invention.
Figure 30:
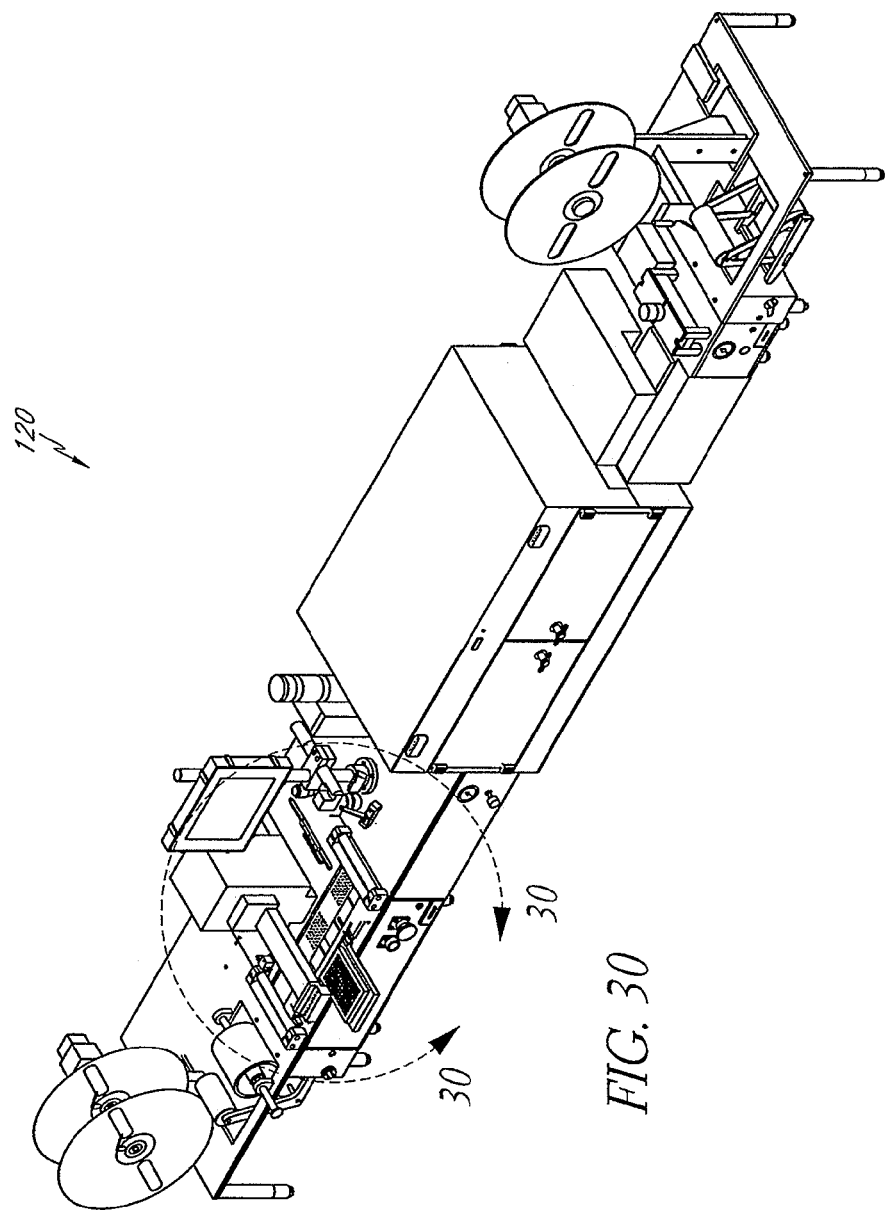
FIG. 30 is a simplified perspective view of the arraying, hybridization and reading system of FIG. 27 system illustrating features and advantages in accordance with certain embodiments of the invention.
Figure 32:
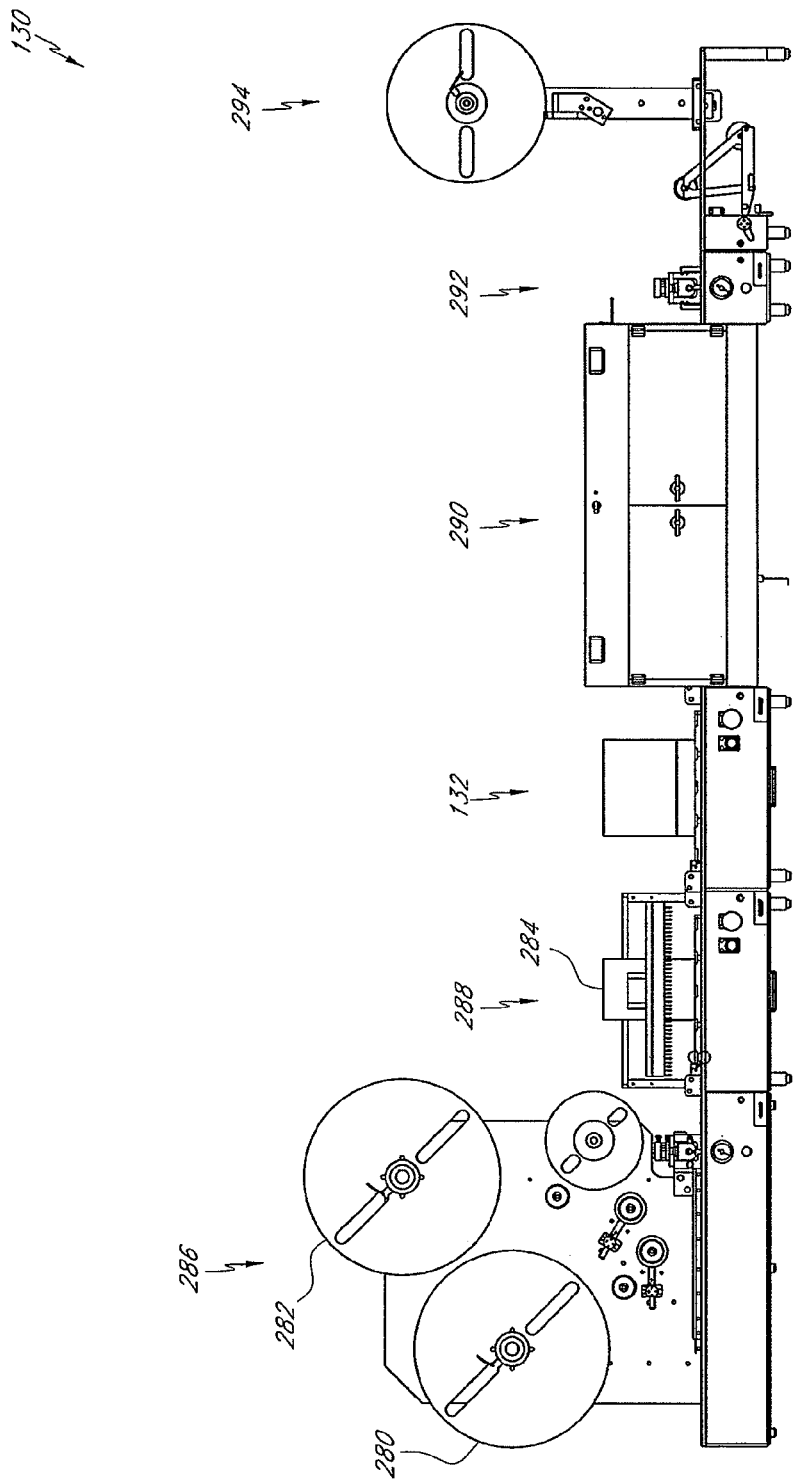
FIG. 32 is a simplified side view of a web based interactive array assembly system with a blocking module illustrating features and advantages in accordance with certain embodiments of the invention.
Figure 33:
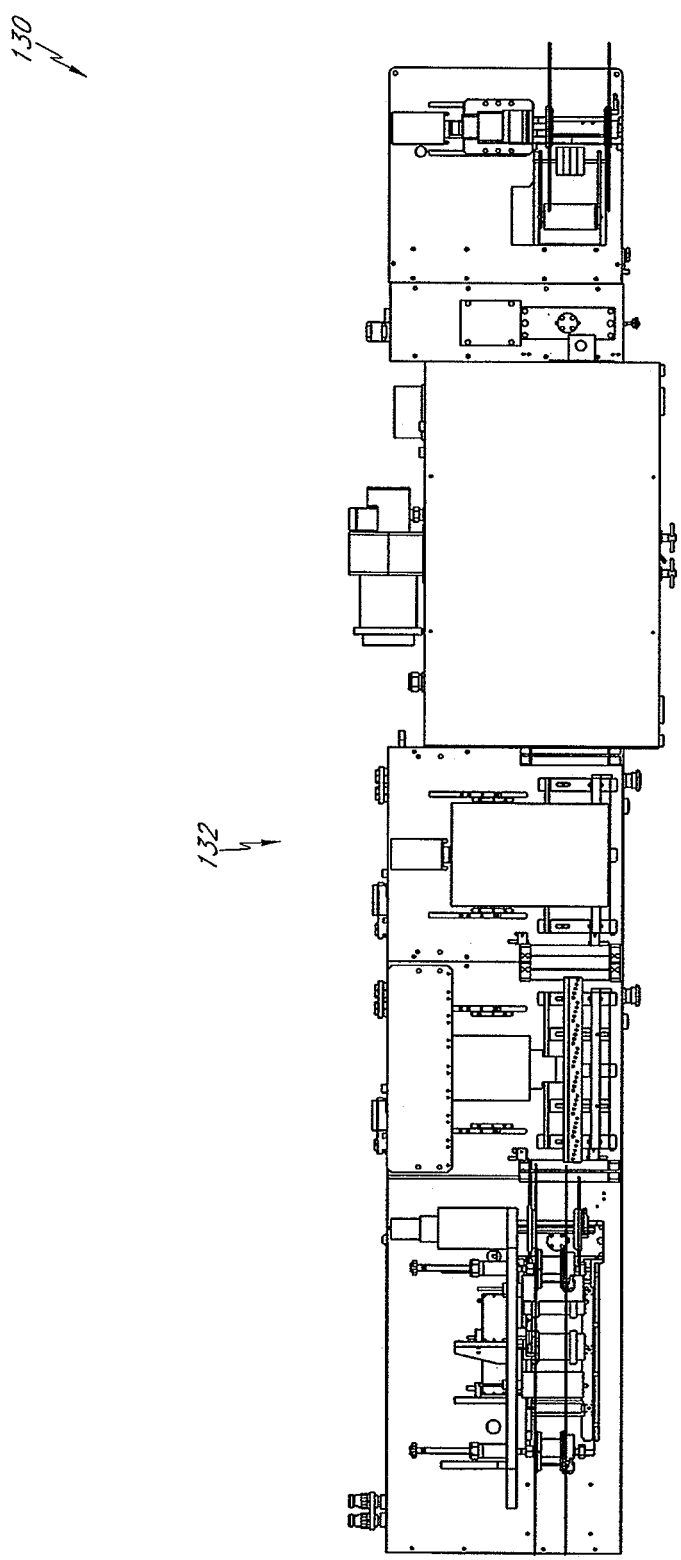
FIG. 33 is a simplified top view of the web based interactive array assembly system of FIG. 32 illustrating features and advantages in accordance with certain embodiments of the invention.

FIGS. 32-34 show different views of certain embodiments of a web based interactive array assembly system 130 comprising a blocking module 132. The array assay blocking wash flow through device manufacturing machine 130 is generally similar to the embodiments of the array manufacturing machine 30 of FIGS. 9-12 except that it has an added blocking/drying station 132.

Referring in particular to FIG. 32, the system 130 in certain embodiments generally comprises, among other things, a backing reel 280, a membrane reel 282, a Y-X axis head motion positioner 284, a laminate module 286, a dispense module 288, the blocker spray or dip module 132, a drying module 290, a capstan module 292, and a take-up module 294.

The blocking/drying stations 132 can efficaciously comprise a liquid dip, aerosol spray of dispensing of a blocking solution directly onto the spots. As shown, for example in FIG. 32, these stations 132 are located directly after the dispense station or module.

In connection with embodiments of the Hybridization/Reader Machine, washing/drying stations are desirably added after the incubation station and before the reader station.

PCR Substrate Related Embodiments:

In some embodiments, a PCR assay is executed with a PCR plate such as the PCR plate or substrate 80c shown in FIG. 18. As set of oligonucleotides are added or dispensed at the dispensing station of an assay array assembly or manufacturing machine. In one embodiment, these comprise two primers and a TagMan® probe.

A TaqMan® assaying system as available from Applied Biosystems of Foster City, Calif., U.S.A. has efficacy with certain particular features of PCR assaying in accordance with some embodiments. Applied Biosystems TaqMan® gene expression assays solutions are discussed in further detail below.

In certain embodiments, the assay machine is used to dispense a cover or host fluid, such as oil or other suitable substantially immiscible and/or inert liquid, onto or into the array formed on the PCR plate 80c in the form of an oil layer or layers. Typically, an oil layer would cover each of the individual array sites, spots, drops or dots A master mix (in one embodiment, a TaqMan® master mix) and a selected sample(s) are then dispensed through the oil layer using non-contact dispensing so that the reaction(s) take place under the oil layer.

European Patent No. EP 1 485 204 B1, the entirety of each one of which is hereby incorporated by reference herein, discloses systems and methods for dispersing or dispensing liquids or reagents below a fluid surface using non-contact dispensing which can be efficaciously utilized in accordance with certain embodiments of the invention. This patent document comprise a part of the present patent specification/application, and a copy of it is also attached herewith as part of the specification.

In these PCR assaying embodiments, the incubation chamber, station, module or system is replaced by a thermal cycling or cycler station, module, system or process. The PCR substrate(s) 80c are then read at the read, reading or reader station, module or system. This substantially completes the PCR assaying process.

Applied Biosystems TaqMan® Gene Expression Assays

Applied Biosystems offers one of the largest family of products to meet your quantitative gene expression needs: from off-the-shelf gene-specific probe and primer sets to Custom TaqMan® probes and primers manufactured to your desired sequences, and everything in between. All products use TaqMan® probe-based chemistry and are designed for use on the suite of Applied Biosystems Real-Time PCR Systems—together the gold standard in quantitative gene expression offering the greatest sensitivity, specificity, reproducibility, and the broadest dynamic range.

TaqMan® Gene Expression Assays

| | |
|---|---|
| Gene-specific TaqMan ® probe and primer sets for quantitative gene expression studies Human, mouse, rat, *Arabidopsis*, *Drosophila*, *C. elegans*, Rhesus macaque, and canine species available | Convenient single-tube format Universal cycling conditions |

Figure 35A:
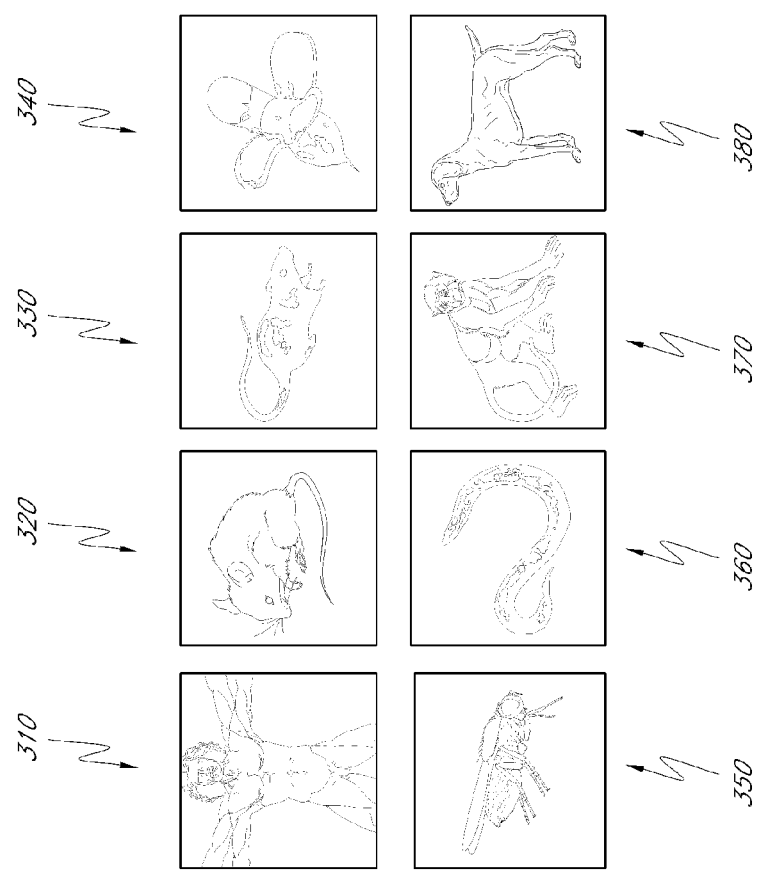
FIG. 35A shows simple views of various species whose genes can be provided for assaying illustrating features and advantages in accordance with certain embodiments of the invention.

TaqMan® Gene Expression Assays are a comprehensive collection of over 700,000 pre-designed probe and primer sets that enable researchers to quickly and easily perform quantitative gene expression studies on human 310, mouse 320, rat 330, *Arabidopsis* 340, *Drosophila* 350, *C. elegans* 360, *Rhesus macaque* 370, or canine 380 genes (see FIG. 35A). Each gene expression assay consists of a FAM™ dye-labeled TaqMan® MGB probe and two PCR primers formulated into a single tube. Every assay is optimized to run under universal thermal cycling conditions with a final reaction concentration of 250 nM for the probe and 900 nM for each primer. This streamlined approach and comprehensive assay selection enables a convenient, standardized process for quantitative gene expression.

Human Assays

Over 200,000 gene expression assays are available for all known human genes. These include genes in the public domain with associated RefSeq transcripts (NCBI Reference Sequence project database: http://www.ncbi.nlm.nih.gov/RefSeq), the mammalian gene collection (MGC), and GenBank® database. A minimum of one assay (probe and primer set) per RefSeq transcript is available as an inventoried, off-the-shelf product currently numbering >24,000 assays. The complete collection includes assays for nearly every exon junction in all known human genes, both in the public domain and the Celera database, covering every probe on the Applied Biosystems Expression Array System.

Mouse and Rat Assays

Over 300,000 mouse and rat assays have been designed for all known genes. As with our human assays, at least one assay per RefSeq transcript has been manufactured and is available from our inventory. High quality assay designs for all other genes are also available on a made-to-order basis, as Custom TaqMan® Gene Expression Assays.

Strain-Neutral Mouse and Rat Assays

The assay design process yields strain-neutral mouse and rat gene expression assays. Polymorphisms are the cause of most sequence variability between strains. By avoiding areas in the gene transcripts of known polymorphisms, we design only strain-neutral gene expression assays.

TaqMan® Gene Copy Number Assays

TaqMan Gene Copy Number Assays are now available to detect gene copy number. Copy number is an important polymorphism in the human genome associated with genetic diseases such as cancer, immune diseases, and neurological disorders. Drug metabolizing enzymes were selected as the first set of TaqMan Gene Copy Number Assays due to their significance in human physiology and disease. Gene Copy Assays were designed to detect CYP2D6, CYP2A6, CYP2E1, GSTT1, and GSTM1.

TaqMan Gene Expression Assays for Mitochondrial DNA Transcripts

TaqMan® Assays are also available for 19 mitochondrial (mt) DNA encoded transcripts, including 13 mt mRNAs, two mt mRNAs and one mt D-Loop. Three additional assays targeting the mt inter-tRNA region are available as Custom TaqMan Gene Expression Assays. Our TaqMan Assays targeting mtDNA transcripts are ideal for sensitive, specific, and accurate quantification of mtDNA transcription.

Like all TaqMan Gene Expression Assays, measurements are made in real-time, use universal cycling conditions and TaqMan® Universal PCR Master Mix.

Comprehensive Coverage and Selection

Not only have we designed an assay for every gene, but also for multiple locations across each gene transcript. More than 700,000 high-quality assay designs are available for human, mouse, rat, *Arabidopsis, Drosophila, C. elegans*, and canine genes on a made-to-order basis. This vast selection allows researchers to select the specific location on a given transcript they wish to detect. For instance, microarray researchers that may prefer a 3' bias in their TaqMan® probe and primer sets will be able to select from robust, pre-designed TaqMan® Gene Expression Assays. Additionally, researchers performing RNA studies can choose multiple assays per gene to validate their knockdown results.

State-of-the-Art Assay Design Bioinformatics

All assays are designed using Applied Biosystems sophisticated bioinformatics pipeline, customized for either the human, mouse, or rat genome. This pipeline consists of three main steps.

Step One

Both public and Celera sequence data are used to identify the optimal probe and primer locations. This process comprises: mapping transcripts to the genome to identify exon boundaries; masking sequence discrepancies between public and Celera data; masking sequence repeats; and masking known SNPs from both public and Celera databases.

Step Two

Proprietary software algorithms generate probe and primer design for the locations identified above. These algorithms include optimal design parameters, such as % GC content, Tm, amplicon length, and low secondary structure to ensure high amplification efficiency. Where possible, designs span an exon-exon junction, eliminating the possibility of detecting genomic DNA.

Step Three

In silico QC ensures each assay is specific to the gene for which it was designed (i.e., the assay will not detect sequences from other genes, or pseudo-genes). Each assay design is processed through a quality scoring system and one high scoring, gene-specific assay design is sent to our state-of-the-art manufacturing facility. All designs meeting our scoring criteria are also displayed in our online catalog and are available on a made-to-order basis. Our graphical map viewer shows each assay's location on the gene to help determine which assay is most appropriate.

Choice of Delivery Formats

Applied Biosystems delivers the assays in either a tube-format or TaqMan® Low Density Array-format (using inventoried assays only). The TaqMan® Low Density Array is a 384-well micro fluidic card that streamlines reaction set-up time, eliminates the need for liquid-handling robotics, and provides standardization across multiple users and/or multiple labs. This format is ideal for analyzing many samples across fixed number of targets, such as for biomarker screening. TaqMan® Arrays arrive ready to use, with your selected TaqMan® Gene Expression Assays pre-loaded into each of the 384 reaction wells. Simply add 100 nL sample mix (sample cDNA and TaqMan Universal PCR Master Mix) to each of the eight sample ports and run on an Applied Biosystems 7900HT Fast Real-Time PCR System. For more information, see the "TaqMan Low Density Array" section on page 9.

Custom TaqMan® Gene Expression Assays

Custom TaqMan® Gene Expression Assays are delivered ready-to-use, along with the probe and primer sequences you designed. Features include: any species or organism; target sequence of your choice; convenient single-tube format; and available in small, medium, and large scales.

Custom TaqMan® Gene Expression Assays are available for any species, any splice variant or any novel gene. Simply download our free File Builder Software to format and submit your target sequence, File Builder Software can be downloaded at www.appliedbiosystems.com/filebuilder. The software easily guides you through the ordering process of selecting the assay size, formatting your target sequence to identify the location of the probe, and submitting your order via e-mail.

File submissions are done in a secure format. Your target sequences and the associated assays that are designed are kept confidential. With Custom TaqMan Gene Expression Assays, you benefit from Applied Biosystems proprietary software algorithms for probe and primer design, which enable you to obtain optimal assays for each target sequence. Assays are delivered in a single-tube, ready-to-use format, along with the probe and primer sequences designed from your submitted sequence.

Automation-Compatible to Accelerate High-Throughput Applications

Both TaqMan® Gene Expression Assays and Custom TaqMan® Gene Expression Assays come pre-formulated in a single, 2D-barcoded tube with an easy-to-read label. The single-tube format requires fewer set-up and pipetting steps to assemble reactions, assisting you to easily scale your throughput. Assay tubes are shipped in a 1D-barcoded 96-position rack designed to accommodate standard liquid-handling robotics and fit seamlessly into automated, high-throughput laboratory processes. Each order of assays also includes a compact disc with an assay information file that includes the assay ID numbers, detector names, reporter dye, and quencher information for easy uploading into a LIMS or sequence detection system software.

A Simple, Standardized Solution for Quantitative Gene Expression

TaqMan Gene Expression Assays and Custom TaqMan Gene Expression Assays are built on our 5' nuclease chemistry and consist of a FAM™ dye-labeled TaqMan® MGB probe (250 nM, final concentration), and two unlabeled PCR primers (900 nM each, final concentration). All components are QC tested and formulated into a single 20× mix. Designed to run under universal conditions for two-step RT-PCR, TaqMan Gene Expression Assays are simple to use. Just add TaqMan® Universal PCR Master Mix (with or without AmpErase® UNG) and your cDNA sample to generate sensitive, reproducible, and truly quantitative gene expression data on any Applied Biosystems Real-Time PCR System.

Compared to do-it-yourself methods, TaqMan Gene Expression Assays and Custom TaqMan Gene Expression Assays eliminate weeks or even months of probe and primer design, formulation, and testing.

TaqMan® Endogenous Controls

Features include: optimized, pre-formulated, ready-to-use control assays; cost-effective gene expression quantitation in human, mouse, rat, and eukaryotes (18S rRNA); Choice of FAM™ or VIC® dye labels.

Applied Biosystems TaqMan® Endogenous Controls are a collection of pre-designed probe and primer sets that can be used to normalize the amount of sample RNA or DNA added to a reaction. For the quantitation of gene expression, deciding upon a specific control can be difficult, even when detailed information about the biological system is available. This can result in trial and error to identify an appropriate control, leading to project delays and increased costs. Applied Biosystems offers endogenous controls for the most commonly used control genes in human, mouse, rat and any eukaryotic (18S rRNA) species. The assays are designed to help researchers quickly and easily identify and run the best possible endogenous control for their gene expression study.

A Simple, Standardized Solution for Quantitative Gene Expression

Each endogenous control is built on our 5' nuclease chemistry and is offered in a choice of two different reporter dyes and two quenchers: a FAM™ dye-labeled TaqMan® MGB probe (250 nM, final concentration) and two unlabeled PCR primers (900 nM each); a VIC® dye-labeled TaqMan® MGB probe (250 nM, final concentration) and two unlabeled PCR primers (150 nM each—primer limited); and a VIC dye-labeled TAMRA™ dye-labeled probe (250 nM, final concentration) and two unlabeled PCR primers (150 nM each—primer limited).

All components are QC tested, formulated into a single 20× mix, and functionally tested. Designed to run under universal conditions for two-step RT-PCR, our TaqMan Endogenous Controls are simple to use. Just add TaqMan® Universal PCR Master Mix (with or without AmpErase® UNG) and your cDNA sample to generate sensitive, reproducible, and truly quantitative gene expression data on ABI Prism® 7000 and 7700 Sequence Detection Systems, Applied Biosystems 7300 and 7500 Real-Time PCR Systems, and Applied Biosystems 7500 and 7900HT Fast Real-Time PCR Systems. Compared to do-it-yourself methods, our TaqMan Endogenous Controls deliver a complete quantitation solution and eliminate weeks or even months of assay design, formulation, and testing.

Choosing the Right Endogenous Control

Endogenous controls can normalize the expression levels of target genes by correcting differences in the amount of cDNA that is loaded into PCR reaction wells. For best results, verify that the endogenous control is consistently expressed in the sample set to be tested. Endogenous control expression must be uniform across all samples in the study. For multiplexing, ensure that the gene expression level of the endogenous control is greater than that of the target.

Multiplex vs. Singleplex PCR

All TaqMan® Endogenous Controls that contain probes labeled with the VIC reporter dye are primer limited. This allows multiplexing of TaqMan Endogenous Controls with target gene expression assays, provided that the control gene is more abundantly expressed than the target gene. All TaqMan Endogenous Controls the contain probes labeled with the FAM reporter dye are not primer limited and are not intended for multiplexing.

Complementary Products

TaqMan® Endogenous Controls are intended to be used with: TaqMan® Gene Expression Assays; custom TaqMan® Gene Expression Assays; TaqMan® Pre-Developed Assay Reagents (PDARs); and Custom TaqMan® Probes and Primers.

| TaqMan ® Endogenous Controls |
|---|
| Eukaryotic 18S rRNA |
| Human ACTB (beta actin) |
| Human B2M (beta-2-microglobulin) |
| Human GAPD (GAPDH) |
| Human GUSB (beta glucuronioase) |
| Human HPHT1 |
| Human PGK1 (phosphoglyceratekinase 1) |
| Human PPIA (cydophilin A) |
| Human RPLO (large ribosomal protein) |
| Human TBP (TATA-box binoing protein) |
| Human TFRC (CD71) (transferring receptor) |
| MouseGAPD (GAPDH) |
| Mouse ACTB (beta actin) |
| Rat GAPD (GAPDH) |
| Rat ACTB (beta actin) |

TaqMan® Low Density Array

Features include: validate microarray hits quickly and economically; standardize screening of gene panels across many samples and laboratories; create the perfect card by designing a custom array that meets your specific need; and load 384 wells in less than five minutes without robotics or multi-channel pipettors.

The TagMan® Low Density Array is a 384-well micro fluidic card that enables you to perform 384 simultaneous real-time PCR reactions without the need for liquid-handling robots or multi-channel pipettors to load samples. This low- to medium-throughput array enables 1 to 8 samples to be run in parallel against 12 to 384 TaqMan® Gene Expression Assay targets that are pre-loaded into each of the wells in the array. The TaqMan Low Density Array is completely customizable—choose from over 47,000 inventoried TaqMan Gene Expression Assays designed for human, mouse, and rat genes to have loaded into a TaqMan® Array. The TaqMan Array is designed for use on the flexible Applied Biosystems 7900HT Fast Reel-Time PCR System with a 7900HT TaqMan® Array Upgrade.

The Ultimate Microarray Validation Tool

TaqMan Arrays are exactly the right tool for validating the tens or hundreds of hits that come from microarrays because they can be customized to include up to 384 of those hits in one easy-to-use card. Using individual assays, or even SYBR®-based assays, to look at 12, 48, or 96 targets can quickly become unmanageable and expensive. TaqMan Low Density Arrays enable researchers to accomplish the validation necessary to arrive at the right answer easily and affordably.

Ideal Screening Technology

TaqMan Low Density Arrays are ideal for screening biomarkers and toxicology panels, and for analyzing pathways, target classes, and complete disease sets. Because TaqMan Arrays don't require liquid-handling robotics for loading, you get standardized results with low variability across many users and laboratories. Plus, TaqMan Gene Expression Assays—the benchmark of specificity and sensitivity in real-time PCR—are pre-loaded into the TaqMan Array, ensuring reliable performance and results you can trust.

Create the Perfect Card

You select TaqMan Gene Expression Assays and the optimal TaqMan Array format for your experiment, and we deliver TaqMan Low Density Arrays pre-loaded with your selected assays in each reaction well. Choose 12 to 384 target assays from our collection of inventoried TaqMan Gene Expression Assays covering human, mouse, and rat genes. Ordering is easy with the new online TaqMan Low Density Array configuration tool to help you search and select genes and assays. Custom TaqMan Arrays are available in nine different formats, covering 12, 16, 24, 32, 48, 64, 96 (2 choices), and 384 assays per Low Density Array.

Designing a TaqMan Low Density Array

Customizing a TaqMan Low Density Array can be done through the Applied Biosystems Web site. Choose your ideal format and TaqMan Gene Expression Assays, select a quantity, and place your order—it's as easy as 1, 2, 3. Or, download our list of customizable gene panels to define a particular target class or pathway using public databases and published articles. The gene lists include a TaqMan Gene Expression Assay to represent each gene in the list that can be used to configure a custom TaqMan Array.

Taqman Low Density Array Format Specifications
TaqMan® Low Density Array (384-well micro fluidic card):

| | | # of Samples per Card | | | |
|---|---|---|---|---|---|
| Description | # of Assays | 1 Replicate | 2 Replicates | 3 Replicates | 4 Replicates |
| Format 12 | 11 + 1 Control | | | | 8 |
| Format 16 | 15 + 1 control | | | 8 | |
| Format 24 | 23 + 1 control | | 8 | | 4 |
| Format 32 | 31 + 1 control | | | 4 | |
| Format 48 | 47 + 1 control | | 4 | | 2 |
| Format 64 | 63 + 1 control | | | 2 | |
| Format 96a | 95 + 1 control | | 2 | | 1 |
| Format 96b | 95 + 1 control | | 2 | | 1 |
| Format 384 | 380 + 1 control | 1 | | | |

TaqMan® Low Density Array Gene Signature Panels

Features include: pre-formatted and inventoried for quick delivery; economical two- or four-card packages simplifies your workflow; TaqMan Gene Expression Assay performance without expensive robotics; and consistent, reliable data across samples, studios, and labs.

TaqMan® Gene Signature Panels are pre-designed, focused gene panels for many important target classes and pathways. Gene sets in each panel have been culled from pathway analysis tools, published review papers, and collaborator and customer input. Select from a variety of TaqMan Gene Signature Panels based on your research needs covering such areas as GPCRs, immune response, or protein kinases. Endogenous Control Panels are also available to assess which housekeeping genes are best for your specific study. TaqMan Gene Signature Panels provide a faster delivery times than our custom TaqMan Arrays because they are already inventoried. TaqMan Gene Signature Panels are packaged in two or four cards per pack, making them more cost effective.

TaqMan® Low Density Array

TaqMan® Arrays can be ordered in any of the following format options: Format 12 (P/N 4342247)–11 unique assays+1 mandatory control, and 8 unique samples; Format 16 (P/N 4346798)–15 unique assays+1 mandatory control, and 8 unique samples; Format 24 (P/N 4342249)–23 unique assays+1 mandatory control, and 8 unique samples; Format 32 (P/N 4346799)–31 unique assays+1 mandatory control, and 4 unique samples; Format 48 (P/N 4342241)–47 unique assays+1 mandatory control, and 8 unique samples; Format 64 (P/N 4346800)–63 unique assays+1 mandatory control, and 2 unique samples; Format 96 (P/N 4342259)–95 unique assays+1 mandatory control, and 4 unique samples; Format 96 (P/N 4342261)–95 unique assays+1 mandatory control, and 2 unique samples; and Format 384 (P/N 4342265)–380 unique assays+4 mandatory controls, and 1 unique sample.

Custom TaqMan® Probes and Primers

Features include: choice of dye labels, quenchers, and synthesis scales; available for any species or organism; and for use in quantitative gene expression, SNP genotyping, other allelic discrimination applications, and pathogen detection When you know the exact sequences you need for your TaqMan® probes and primers, Applied Biosystems can synthesize them for you. As the market leader in real-time PCR, our high-quality custom products can be used in all of your real-time and end-point PCR applications. These products offer you the ideal in flexibility, whether you prefer to optimize your own reaction formulation, or if you simply require large quantities Our Custom TaqMan® Probes and Primers are manufactured at three sites around the world—the United States, the United Kingdom, and Japan—to provide excellent delivery time. Order by fax e-mail, or online and send your sequences to our synthesizers electronically, reducing delivery time.

Choice of Quenchers

Applied Biosystems Custom TaqMan® Probes incorporate a 5' reporter dye and a 3' quencher. Our most popular quencher is a non-fluorescent quencher (NFQ) combined with an MGB (minor groove binder) moiety. The NFQ offers the advantage of lower background signal, which results in better precision in quantitation. The MGB moiety stabilizes the hybridized probe and effectively raises the melting temperature ($T_m$). This means that MGB probes can be shorter than traditional dual-labeled probes, which make them better suited for allelic discrimination applications. The shorter probe lengths mean that single base mismatches (e.g., SNPs) will have a greater destabilizing effect on an MGB probe, resulting in better discrimination. The shorter length also offers greater design flexibility for all real-time PCR applications.

Applied Biosystems offers the traditional dual-labeled Custom TaqMan Probes with a TAMRA™ dye fluorescent quencher as well. All TAMRA dye TaqMan probes are HPLC purified.

A Selection of Reporter Dyes

Applied Biosystems Custom TaqMan Probes can be ordered with variety of different reporter dyes to facilitate your multiplexing applications.

Synthesis Scales

TaqMan Custom Probes and Primers are available in a choice of three standard sizes. Each includes a pre-defined quantity of probe or primer to ensure that you get the same amount each time you order and aren't subject to variations in synthesis yield. For larger synthesis scales on these products, please contact your local Applied Biosystems Sales Representative.

Primer Express® Design Software

Applied Biosystems Primer Express® software is available to simplify the probe and primer design process. Primer Express is available for individual users and in multi-user packs.

Other Fluorescent Dye-Labeled Oligos

Applied Biosystems also offers a host of other custom oligo products for use in many applications, including microsatellite-based linkage mapping, mutation detection, and more.

| CUSTOM TAQMAN PROBES AND PRIMERS | | | |
|---|---|---|---|
| Probe Type (3' Quencher) | Reporter Dye (5') Label | Quantity | Probe Length |
| TaqMan® TAMRA™ Dye Probes | 6-FAM ™ VIC ®, or TET ™ | 6,000 µmol | Up to 35 bases |
| | 6-FAM, VIC, or TET | 20,000 µmol | Up to 35 bases |
| | 6-FAM, VIC, or TET | 50,000 µmol | Up to 35 bases |
| TaqMan® MGB Probes | 6-FAM, VIC, TET, or NED'" | 6,000 µmol | 13-25 bases |
| | 6-FAM, VIC, TET, or NED | 20,000 µmol | 13-25 bases |
| | 6-FAM, VIC, TET, or NED | 50,000 µmol | 13-25 bases |
| Real-Time PCR Primers sequence detection primers) | N/A | 10,000 µmol | N/A |
| | N/A | 80,000 µmol | N/A |
| | N/A | 130,000 µmol | N/A |

Please note that NED dye can give lower signal intensity than FAM, VIC or TET dye or most Real-Time PCR Systems. The Applied Biosystems 7500 Real-Time PCR System has been optimized to yield higher signal intensity for NED dye.

TaqMan® MicroRNA Assays

| | |
|---|---|
| Highly specific-quantitate only the biologically active mature miRNAs | Fast, simple, and scalable-two-step qRT-PCR assay provides high-quality results in less than three hours |
| Sensitive-conserves limited samples, requires only 1-10 nanograms of total RNA or equivalent | Broad coverage-choose from human, mouse, rat, *Arabidopsis*, *C. elegans*, and *Drosophila* genes |
| Wide dynamic range-up to seven logs-detect high and low expressors in a single experiment | |

By making novel adaptation in assay design, Applied Biosystems is able to bring our gold standard specificity, sensitivity, and simplicity of TaqMan® Assays and real-time PCR to miRNA detection and quantitation.

The basis of TaqMan® MicroRNA Assays is a target-specific stem-loop structure, reverse-transcriptase primer. Its innovative design overcomes a fundamental problem in miRNA quantitation: the short length of mature miRNAs (~22 nt) prohibits conventional design of a random-primed RT step followed by a specific real-time assay. The stem-loop accomplishes two goals: 1) specificity for only the mature miRNA target, and 2) formation of a RT primer/mature miRNA-chimera, extending the 5' end of the miRNA. The resulting longer RT amplicon presents a template amenable to standard real-time PCR, using TaqMan Assays.

To ensure accurate results, every individual TaqMan MicroRNA Assay design has been functionally validated under laboratory conditions.

Distinguish Between Highly Homologous Mature miRNAs

TaqMan MicroRNA Assays are not only specific for mature miRNAs, they can also successfully distinguish between highly homologous targets. As many miRNA family members (i.e. the let-7 miRNA family) differ in sequence by as little as one base, real-time PCR using TaqMan Assays gives the specificity needed for differentiation.

Requires Only Minimal Starting Materials

TaqMan MicroRNA Assays are extremely sensitive—researchers need only 1-10 nanograms of purified total RNA or equivalent to reliably quantify their miRNAs of interest, not the several micrograms typically required for hybridization-based methods.

Unparalleled Dynamic Range

TaqMan MicroRNA Assays deliver the wide linear, dynamic range TaqMan Assays are known for—up to seven logs. This means that researchers can accurately quantitate miRNA targets varying from a few copies to millions of copies in the same experiment. This is an important factor given the wide range of miRNA concentrations within and across different cells, tissue types, and disease states.

Fast Time-to-Results

By taking advantage of gold-standard TaqMan reagent-based technology with universal thermal cycling conditions, TaqMan MicroRNA Assays are familiar, fast, and easy to set up. Just start with your total RNA sample, and get results in less than three hours using any Applied Biosystems Real-Time PCR System.

Convenient and Scalable Solution

TaqMan MicroRNA Assays are pre-designed, functionally validated, and available off-the-shelf from Applied Biosystems, making them extremely convenient.

Broad Range of Species

TaqMan MicroRNA Assays are available for a range of species, including human, mouse, rat, *Drosophila, C. elegans*, and *Arabidopsis*. Endogenous controls for human and mouse assays are also available. Applied Biosystems will continue to increase the number of TaqMan® MicroRNA Assays for these species, with the goal of keeping aligned with the Sanger miRBase Registry.

TaqMan® MicroRNA Reverse Transcription (RT) Kit

The TaqMan® MicroRNA RT Kit provides the necessary components for optimal performance of TaqMan MicroRNA Assays. Components of this kit are used with the RT primer provided with the MicroRNA Assay to convert miRNA to cDNA. This kit is available In 200 or 1,000-reaction sizes.

Figure 35B:
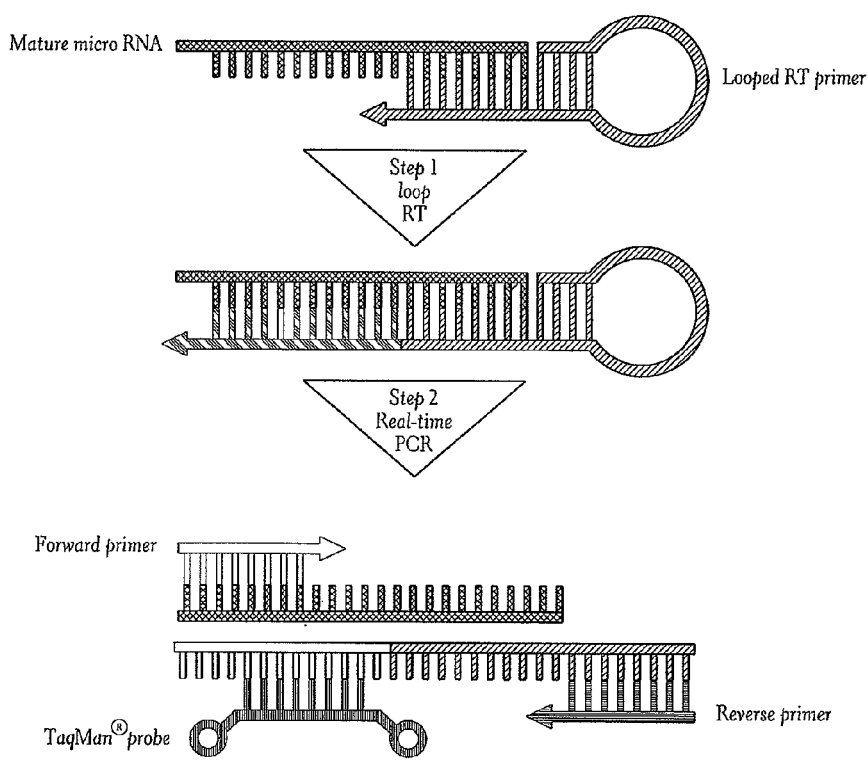
FIG. 35B is a simplified view of TaqMan® PCR assaying mechanism illustrating features and advantages in accordance with certain embodiments of the invention.

FIG. 35B illustrates the use of TaqMan® MicroRNA Assays and shows a simple, two-step mechanism that provides the advantages of real-time PCR to miRNA quantitation.

TaqMan® PreAmp Master Mix Kit

| | |
|---|---|
| Amplifies cDNA targets equally without introducing bias | Stretches 1 ng of cDNA into 200 real-time PCH reactions for gene expression analysis using TaqMan ® Gene Expression Assays |
| Multiplex up to 100 gene expression targets with minimal hands-on time | Ideal for laser capture microdissections, needle biopsies, and paraffin-embedded tissues |

New TaqMan® PreAmp Master Mix (Early Access) from Applied Biosysterns preamplifies small amounts of cDNA without introducing amplification bias to the sample. Gene expression analysis of scarce cDNA is no longer inaccurate and labor-intensive. The TaqMan PreAmp Master Mix Kit uniformly enriches 1 to 250 ng of starting cDNA material for up to 100 gene targets using a pool of TaqMan Gene Expression Assays as a source of primers. The PreAmp kit provides a simple, easy workflow and quantitative, reproducible results.

The standard real-time PCR reaction for gene expression analysis starts with the reverse transcription of total RNA to cDNA using random primers, followed by real-time PCR using a probe and gene-specific primers. With the TaqMan PreAmp Master Mix, an intermediate multiplex step between reverse transcription and real-time PCR is performed in which the cDNA is enriched for up to 100 gene targets using a pool of TaqMan® Gene Expression Assays. The preamplification reaction is cycled for 10 or 14 cycles to generate approximately 1,000 to 16,000-fold amplification of each gene-specific target. The resulting preamplified reaction is diluted and serves as the starting material for the subsequent singleplex real-time PCR with each of the individual TaqMan® Gene Expression Assays represented in the assay pool.

Uniform, Unbiased Amplification

TaqMan® PreAmp Master Mix has been shown to provide virtually no difference in the $\Delta\Delta C_t$ between preamplified cDNA from 1 ng to 250 ng of starting material and control cDNA. For these preamplified targets, TaqMan PreAmp Master Mix provides extremely high correlation between the CT values for cDNA and control cDNA for 1 ng and 25 ng of starting material (data above).

Reliable and uniform preamplification enables researchers to analyze gene expression for limited quantities of cDNA samples from needle biopsies, laser capture microdissections (LCMs), and formalin-fixed paraffin-embedded (FFPE) samples.

Complete Product Suite for Seamless Workflow

The TaqMan PreAmp Master Mix Kit comes with the new TaqMan PreAmp Master Mix and our TaqMan Universal PCR Master Mix. Both reagents work in tandem to provide optimal preamplifcation of cDNA. In addition to the TaqMan PreAmp Master Mix Kit, other Applied Biosystems products required for successful preamplification of cDNA include: TaqMan Gene Expression Assays; High Capacity cDNA Reverse Transcription Kit; GeneAmp® PCR System 9700; and Applied Biosystems 7300, 7500, 7500 Fast or 7900HT Fast Real-Time PCR System.

Figure 35C:
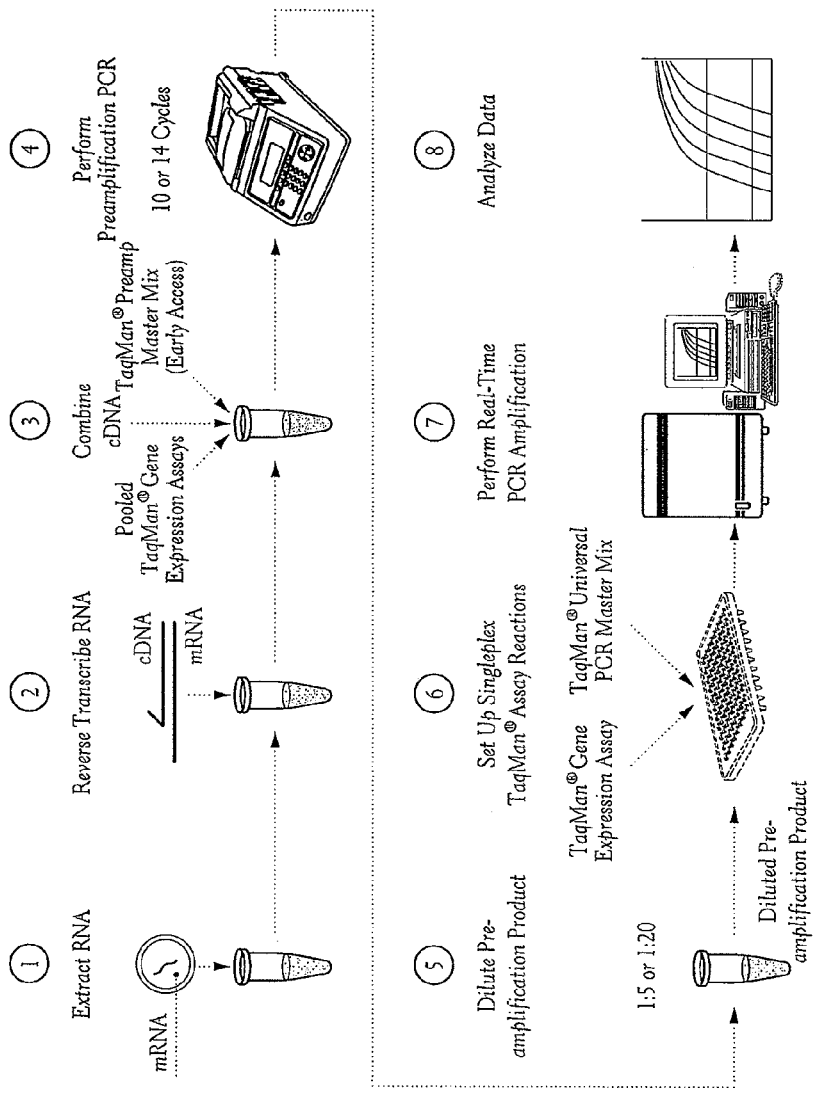
FIG. 35C is a simplified schematic view of a gene expression analysis workflow or flowchart illustrating features and advantages in accordance with certain embodiments of the invention.

FIG. 35C shows an example of a complete workflow for analyzing gene expression using TaqMan® PreAmp Master Mix. In this example, the preamplification step takes only about 15 additional minutes of hands-on time and about 1.5 hours of cycling time.

Product Specification Comparison

|  | Fill Volumes | Number of Reactions | Available Reporter Dye Labels | Universal Formulation |
|---|---|---|---|---|
| TaqMan ® Gene Expression Assays | | | | |
| Inventoried | 250 μL, 20X | 250 (@20 μL) | FAM ™ | Yes |
| Made to Order | 360 μL, 20X | 360 (@20 μL) | FAM | Yes |
| Custom TaqMan ® Gene Expression Assays | | | | |
| Small-scale | 360 μL, 20X | 360 (@20 μL) | FAM | Yes |
| Medium-scale | 750 μL, 20X | 750 (@20 μL) | FAM | Yes |
| Large-scale | 967 μL, 60X | 2,900 (@20 μL) | FAM | Yes |
| TaqMan ® Endogenous Controls | | | | |
| Primer limited |  |  | VIC | Yes |
| Not primer limited |  |  | FAM | Yes |
| Custom TaqMan ® Probes and Primers |  |  | FAM | No |
|  |  |  | VIC | No |
|  |  |  | TET | No |
|  |  |  | NED | No |
| TaqMan ® PreAmp Master Mix | 1 mL | 40 (@50 μL) |  |  |
| TaqMan ® MicroRNA Assays |  | 150 (@20 μL) | FAM | Yes |
| Custom TaqMan ® Low Density Arrays† |  | 384 (@1 μL) |  |  |
| TaqMan ® Low Density Array Gene Signature Panels‡ |  | 384 (@1 μL) |  |  |

TaqMan® Low Density Array Gene Signature Panels

| Gene Signature Panel Name | Number of Targets/Controls | Format | Pack Size |
|---|---|---|---|
| Human Immune Panel. | 90/6 | Formal 96a | 4 cards/pack |
| Mouse Immune Panel | 90/6 | Formal 96a | 4cards/pack |
| Human Protein Kinase Panel | 94/2 | Formal 96a | 4 cards/pack |
| Human GPCR Panel | 367/14 | Formal 384 | 4 cards/pack |
| Mouse GPCR Panel | 365/16 | Formal 384 | 4 cards/pack |
| Human ABC Transporter Panel | 50/14 | Formal 64 | 4 cards/pack |
| Human Apoptosis Panel | 93/3 | Formal 96a | 4 cards/pack |
| Human Endogenous Control Panel | 16 | Formal 16 | 2 cards/pack |
| Mouse Endogenous Control Panel | 16 | Formal 16 | 2 cards/pack |
| Rat Endogenous Control Panel | 16 | Formal 16 | 2 cards/pack |

Some Novel Features of Certain Embodiments

The array printing, hybridization, quantitative development and assaying systems and methods of embodiments of the invention provide several advantages some of which relate to high throughput abilities and conservation of valuable liquids or reagents. The following represent some, but not limited to, novel and/or unique features, aspects and advantages in accordance with certain embodiments:

(1) Some embodiments provide bulk dispenser configurations and software/motion transformations that allow the use of dispensers in arrays with large spacing to configure dense packed arrays on the substrate at high speeds with controlled drop volumes. In some of these embodiments, one dispense line is always connected to a specific reagent or liquid. In some of these cases, no aspiration steps are performed.

(2) In some embodiments, the arrayed dispensers can be used to manufacture not only fixed arrays but also desirably any possible array that consists of or comprises a sub-segment of these dispensers.

(3) Certain embodiments have the capability of dispensing drops having volumes ranging from about 1 microliter (4) down to about 100 picoliters (pL) or less with spot sizes greater than about 1 mm down into the range of 50 microns (μm) or less, including all values and sub-ranges therebetween. In some embodiments, the drop size or volume is in the range from about 20 picoliters (pL) to about 1 microliter (μL), including all values and sub-ranges therebetween.

(4) Some embodiments advantageously provide array designs and web designs that allow for high speed processing and tracking.

(5) In some embodiments, any optical detection technology may be efficaciously utilized. These include, without limitation, chemoluminescence, fluorescence, and absorption, among others, as needed or desired.

(6) Certain embodiments desirably utilize a drop on drop methodology for hybridization and/or other assaying processes. In some embodiments, an inert substrate is employed. In some other embodiments, an active substrate is used. Certain related embodiments advantageously include the use of the drop kinetic energy to assist in good mixing to efficaciously enhance the reaction kinetics.

(7) Some embodiments advantageously use tandem motion systems on or in conjunction with hybridization and/or other assaying systems to desirably achieve a high throughput process by putting or dispensing sample drops on the array spots using otherwise inherently slow processes such as the aspirate/dispense process.

(8) Certain embodiments desirably utilize the web format for arrays which provides for simple blocking, drying and washing of active array formats to achieve the ability for high throughput processing.

(9) In some embodiments, belts of a substrate are utilized which can desirably provide the capability to carry thousands (and in some cases even more) of arrays. This advantageously allows for a continuous incubation and readout system.

The methods which are described and illustrated herein are not limited to the sequence of acts described, nor are they necessarily limited to the practice of all of the acts set forth. Other sequences of acts, or less than all of the acts, or simultaneous occurrence of the acts, may be utilized in practicing embodiments of the invention.

It is to be understood that any range of values disclosed, taught or suggested herein comprises all values and subranges therebetween. For example, a range from 5 to 10 will comprise all numerical values between 5 and 10 and all subranges between 5 and 10.

From the foregoing description, it will be appreciated that a novel approach for diagnostic arraying and/or assaying has been disclosed. While the components, techniques and aspects of the invention have been described with a certain degree of particularity, it is manifest that many changes may be made in the specific designs, constructions and methodology herein above described without departing from the spirit and scope of this disclosure.

While a number of preferred embodiments of the invention and variations thereof have been described in detail, other modifications and methods of using and diagnostic applications for the same will be apparent to those of skill in the art. Accordingly, it should be understood that various applications, modifications, and substitutions may be made of equivalents without departing from the spirit of the invention or the scope of the claims.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the claims, including the full range of equivalency to which each element thereof is entitled.

What is claimed is:

1. A high speed array manufacturing system, comprising:
   a series of dispense heads with each comprising a plurality of dispense channels with each dispense channel comprising a dispense tip to form a set of dispense tips, the dispense tips of each dispense channel being arranged in a predetermined configuration and having a predetermined spacing therebetween;
   a motion controls means that is configured to provide substantially continuous relative motion between a web-based substrate structure, having a plurality of fiducials and a longitudinal axis, and the dispense tips at a predetermined high speed in a direction generally parallel to the longitudinal axis;
   each set of the dispense tips being arranged in a staggered arrangement such that the predetermined configurations of the dispense tips are angled, diagonal or non-linear relative to said relative motion;
   a controller configured to selectively trigger each of the dispense channels based on a timing sequence and positioning of each fiducial relative to each dispense tip to dispense reagent droplets onto the substrate structure;
   wherein when the system is in use said drops comprise a part of the system;
   wherein said web-based substrate structure comprises a part of the system; and
   wherein the controller is further configured to control the operation and movement between the dispense tips and the substrate structure based on at least one control signal to control dispensing from the dispense channels relative to the substrate fiducials to form at least one array of reagent dots or spots, in a predetermined pattern, with the reagent dots or spots arranged at a predetermined location on the substrate structure to form a plurality of independent arrays on the substrate structure.

2. The system of claim 1, wherein the system is configured such that said drops have a volume in the range from about 100 picoliters or less to about 1 microliter.

3. The system of claim 2, wherein said drops have a volume in the range from about 20 picoliters to about 1 microliter.

4. The system of claim 1, wherein the system is configured such that at least said reagent drops and said substrate structure have properties such that said spots have a size in the range from about 50 microns to about 1 mm or greater.

5. The system of claim 1, wherein said dispense channels comprise solenoid actuated dispensers.

6. The system of claim 1, wherein said substrate structure comprises an inert or passive substrate.

7. The system of claim 1, wherein said substrate structure comprises an interactive or active substrate.

8. The system of claim 1, wherein said substrate structure comprises a film and a carrier arranged in a web format.

9. The system of claim 1, wherein said system further comprises a membrane handling system.

10. The system of claim 1, wherein said dispensers comprise piezo dispensers.

11. The system of claim 1, wherein at least one of the arrays has a density defined by about forty of said spots formed on a predetermined area on the substrate structure, and wherein said predetermined area is generally rectangular and is defined by a size of about 14 mm multiplied by about 8 mm in area.

12. The system of claim 11, wherein said controller is configured to provide said relative motion with a speed of about 60 mm per second.

13. The system of claim 12, wherein said system is configured to produce at least one said array substrate per second.

14. The system of claim 4, wherein the system is configured to form an array substrate which has at least about three thousand of said reagent spots formed thereon in an array arrangement with center to center spacings of about 2 mm between adjacent spots.

15. The system of claim 14, wherein said array substrate has a density defined by about three thousand of said spots formed on a predetermined area on the substrate structure, and wherein said predetermined area is generally rectangular and is defined by a size of about 99 mm multiplied by about 29 mm in area.

16. The system of claim 3, wherein the system is configured to produce at least about six million array substrates per year.

17. The system of claim 16, wherein the system is configured to produce at least about eighteen million array substrates per year.

18. The system of claim 17, wherein the system is configured to produce at least about one billion array substrates per year.

19. The system of claim 1, wherein said controller is configured to use dispensing data from a text file in cooperation with a software program which is interfaced to said controller to precisely control and coordinate dispensing of said reagent drops, and wherein the text file comprises a part of the system.

20. The system of claim 19, wherein said text file is a user-defined text file created from a spreadsheet of values or template with lists of numbers of user-defined dispense volumes of one or more reagents and corresponding coordinates of the dispense locations.

21. The system of claim 20, wherein the system further comprises a tandem fluid source system which comprises two reagent sources correspondingly coupled to each dispense head, and wherein the tandem fluid source system is configured to sequentially fill and dispense reagent from each dispense head so that high throughput and substantially continuous operation of each of the dispense head is achieved.

22. The system of claim 1, wherein the motion control means is configured to move the substrate structure.

23. The system of claim 1, wherein the motion control means is configured to move at least one of the dispense heads.

24. The system of claim 1, wherein the system is configured to adjust the angled, diagonal or non-linear arrangement of the dispense tips.

25. The system of claim 1, wherein the system further comprises a camera for monition system operation.

26. A high speed array manufacturing method, comprising:
providing a series of dispense heads with each comprising a plurality of dispense channels with each dispense channel having a dispense tip to form a set of dispense tips, the dispense tips being arranged in a predetermined configuration and having a predetermined spacing therebetween;
providing substantially continuous relative motion between a web-based substrate structure, having a plurality of fiducials and a longitudinal axis, and the dispense tips at a predetermined high speed in a direction generally parallel to the longitudinal axis;
further arranging each set of the dispense tips in a staggered arrangement such that the predetermined configurations of the dispense tips are angled, diagonal or non-linear relative to the longitudinal axis of said relative motion;
selectively triggering each of the dispense channels based on a timing sequence and positioning of each fiducial relative to each dispense tip to dispense reagent droplets onto the substrate structure;
controlling the operation and movement of the dispense tips and the substrate structure based on at least one control signal to control dispensing from the dispense channels relative to the substrate fiducials to form at least one array of reagent dots or spots, in a predetermined pattern, with the reagent dots or spots arranged at a predetermined location on the substrate structure to form a plurality of independent arrays on the substrate structure.

27. The method of claim 26, wherein the controlling involves controlling the dispensing of said drops from the dispense channels such that they deposit at least 50 drops or at least 500 drops per second per dispense channel onto the substrate structure.

28. The method of claim 26, wherein the method further comprises forming said drops to have a volume in the range from about 100 picoliters or less to about 1 microliter.

29. The method of claim 26, wherein the method further comprises forming spots to have a size in the range from about 50 microns to about 1 mm or greater.

30. The method of claim 26, wherein the method further comprises providing the dispense channels as solenoid actuated or piezo dispensers.

31. The method of claim 26, wherein the method further comprises substantially continuous in-line web based manufacturing of a plurality of said substrate structures.

32. The method of claim 26, wherein the method further comprises providing the substrate structure as a film and a carrier arranged in a web format.

33. The method of claim 26, wherein the method further comprises manufacturing at least one million substrate structures per year.

34. The method of claim 26, wherein providing substantially continuous relative motion comprises moving the substrate structure.

35. The method of claim 26, wherein providing substantially continuous relative motion comprises moving the dispense heads.

36. The method of claim 26, wherein the method further comprises adjusting the angled, diagonal or non-linear arrangement of the dispense tips.

37. The method of claim 26, wherein the method further comprises using a camera to monitor system operation.

* * * * *